US010808264B2

(12) United States Patent
Takakura et al.

(10) Patent No.: US 10,808,264 B2
(45) Date of Patent: Oct. 20, 2020

(54) METHOD FOR PRODUCING BENZALDEHYDE

(71) Applicant: AJINOMOTO CO., INC., Tokyo (JP)

(72) Inventors: Yasuaki Takakura, Kanagawa (JP); Keiko Danjo, Kanagawa (JP); Keita Fukui, Kanagawa (JP); Sayaka Asari, Kanagawa (JP); Takuto Ono, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 16/032,206

(22) Filed: Jul. 11, 2018

(65) Prior Publication Data

US 2018/0312881 A1 Nov. 1, 2018

Related U.S. Application Data

(63) Continuation of application No. PCT/JP2017/000887, filed on Jan. 12, 2017.

(30) Foreign Application Priority Data

Jan. 12, 2016 (JP) ................................ 2016-003878

(51) Int. Cl.
*C12P 7/24* (2006.01)

(52) U.S. Cl.
CPC ......... *C12P 7/24* (2013.01); *C12Y 101/99031* (2013.01); *C12Y 104/03002* (2013.01); *C12Y 113/11046* (2013.01); *C12Y 401/01007* (2013.01)

(58) Field of Classification Search
CPC .... C12Y 104/03002; C12Y 401/01007; C12Y 101/99031; C12Y 113/11046; C12P 7/24
See application file for complete search history.

(56) References Cited

U.S. PATENT DOCUMENTS 5,151,353 A 9/1992 Geusz et al.

OTHER PUBLICATIONS

Mandelstam et al., Induction and multi-sensitive end-product repression in the enzymatic pathway degrading mandelate in Pseudomonas fluorescens. Biochem. J., 1965, vol. 94: 569-577. (Year: 1965).*
Tsou et al., Mandelate pathway of Pseudomonas putida: sequence relationships involving mandelate racemase, (S)-mandelate dehydrogenase, and benzoylformate decarboxylase and expression of benzoylformate decarboxylase in *Escherichia coli*. Biochemistry, 1990, vol. 29: 9856-9862. (Year: 1990).*
International Search Report for PCT Patent App. No. PCT/JP2017/000887 (dated Apr. 3, 2017).
Written Opinion for PCT Patent App. No. PCT/JP2017/000887 (dated Apr. 3, 2017).
Pugh, S., et al., "Engineering *Escherichia coli* for renewable benzyl alcohol production," Metabolic Eng. Commun. 2015;2:39-45.
Müller, U., et al., "Metabolic engineering of the *E. coli* L-phenylalanine pathway for the production of D-phenylglycine (D-Phg)," Metabolic Eng. 2006;8:196-208.
Lomascolo, A., et al., "Shifting the biotransformation pathways of L-phenylalanine into benzaldehyde by Trametes suaveolens CBS 334.85 using HP20 resin," Lett. Appl. Microbiol. 2001;32:262-267.
Chu, F. L., et al., "Model Studies on the Oxygen-Induced Formation of Benzaldehyde from Phenylacetaldehyde Using Pyrolysis GC-MS and FTIR," J. Agric. Food Chem. 2008;56:10697-10704.
Massad, G., et al., "Proteus mirabilis Amino Acid Deaminase: Cloning, Nucleotide Sequence, and Characterization of aad," J. Bacteriol. 1995;177(20):5878-5883.
Sun, Z., et al., "Metabolic engineering of the L-phenylalanine pathway in *Escherichia coli* for the production of S- or R-mandelic acid," Microbial Cell Factories 2011;10:71, 13 pp.
Liu, S. P., et al., "Heterologous pathway for the production of L-phenylglycine from glucose by *E. coli*," J. Biotechnol. 2014;186:91-97.
Wang, P., et al., "Immobilization of (S)-mandelate dehydrogenase and its catalytic performance on stereoselective transformation of mandelic acid," J. Taiwan Inst. Chem. Engineers 2014;45:744-748.
Park, J. K., et al., "Production of benzaldehyde by encapsulated whole-cell benzoylformate decarboxylase," Enzyme and Microbial Technol. 2002;30:726-733.

* cited by examiner

*Primary Examiner* — Ganapathirama Raghu
(74) *Attorney, Agent, or Firm* — Cermak Nakajima & McGowan LLP; Shelly Guest Cermak

(57) ABSTRACT

A method for producing benzaldehyde is provided. Benzaldehyde is produced from L-phenylalanine or a carbon source by using microorganism(s) having amino acid deaminase, 4-hydroxymandelate synthase, (S)-mandelate dehydrogenase, and benzoylformate decarboxylase.

26 Claims, No Drawings

Specification includes a Sequence Listing.

SEQUENCE LISTING

```
<160> NUMBER OF SEQ ID NOS: 68

<210> SEQ ID NO 1
<211> LENGTH: 50
<212> TYPE: DNA
<213> ORGANISM: Artificial Sequence
<220> FEATURE:
<223> OTHER INFORMATION: primer

<400> SEQUENCE: 1

gggaattcca tatgaaaatc tcgcgtcgta agctgttatt aggggttggt              50


<210> SEQ ID NO 2
<211> LENGTH: 33
<212> TYPE: DNA
<213> ORGANISM: Artificial Sequence
<220> FEATURE:
<223> OTHER INFORMATION: primer

<400> SEQUENCE: 2

cccaagcttt tagctaaaac gggaaagttt ata                                33


<210> SEQ ID NO 3
```

<211> LENGTH: 30
<212> TYPE: DNA
<213> ORGANISM: Artificial Sequence
<220> FEATURE:
<223> OTHER INFORMATION: primer

<400> SEQUENCE: 3
ggaattccat atgcagaact ttgaaatcga 30

<210> SEQ ID NO 4
<211> LENGTH: 30
<212> TYPE: DNA
<213> ORGANISM: Artificial Sequence
<220> FEATURE:
<223> OTHER INFORMATION: primer

<400> SEQUENCE: 4
accgctcgag tcaacgaccg gcaacttcgc 30

<210> SEQ ID NO 5
<211> LENGTH: 30
<212> TYPE: DNA
<213> ORGANISM: Artificial Sequence
<220> FEATURE:
<223> OTHER INFORMATION: primer

<400> SEQUENCE: 5
ggaattcatt aatgctgcct ccgtttccgt 30

<210> SEQ ID NO 6
<211> LENGTH: 30
<212> TYPE: DNA
<213> ORGANISM: Artificial Sequence
<220> FEATURE:
<223> OTHER INFORMATION: primer

<400> SEQUENCE: 6
accgctcgag tcaacgacgt gccggaccca 30

<210> SEQ ID NO 7
<211> LENGTH: 30
<212> TYPE: DNA
<213> ORGANISM: Artificial Sequence
<220> FEATURE:
<223> OTHER INFORMATION: primer

<400> SEQUENCE: 7
ggaattccat atgagccgca acctgtttaa 30

<210> SEQ ID NO 8
<211> LENGTH: 30
<212> TYPE: DNA
<213> ORGANISM: Artificial Sequence
<220> FEATURE:
<223> OTHER INFORMATION: primer

<400> SEQUENCE: 8
accgctcgag tcatgcatgg gtgcctttac 30

<210> SEQ ID NO 9
<211> LENGTH: 30
<212> TYPE: DNA
<213> ORGANISM: Artificial Sequence
<220> FEATURE:
<223> OTHER INFORMATION: primer

<400> SEQUENCE: 9
ggaattcatt aatggcaagc gttcatggca 30

<210> SEQ ID NO 10
<211> LENGTH: 30
<212> TYPE: DNA
<213> ORGANISM: Artificial Sequence
<220> FEATURE:
<223> OTHER INFORMATION: primer

<400> SEQUENCE: 10
accgctcgag tcatttaacc ggactaacgg 30

<210> SEQ ID NO 11
<211> LENGTH: 1419
<212> TYPE: DNA
<213> ORGANISM: Providencia rettgeri

<400> SEQUENCE: 11
atgaaaatct cgcgtcgtaa gctgttatta ggggttggtg ctgctggtgt tttagcaggg 60
ggtgctgcgg ttgttcctat gatcaatcgt gaaggtcgtt ttgaatcgac taaatcacgt 120
gtaccagctg ttgctggcac agaaggcaaa ttaccagagt ctgcagatgc agtcatcatc 180
ggtgccggcc ttcaagggat catgactgca attaaccttg ctgaaaaagg tcttaatgtt 240
gttatctgtg aaaaaggtgt tgtcggtggt gagcaatcag gccgtgcata tagccaaatt 300
atcagttata agacttcccc agctattttc cctttacacc attacggaaa aattcaatgg 360
cttggcatga acgaaaaaat cggtgctgat accagctacc gtgttcaagg ccgtgttgaa 420
gtaccttcaa gcgaagaaga tttagaaatt tcaagagcct ggattaaatc tgcatctgaa 480
aacccaggtt tcgatacacc tttacgtacc cgtatgattg aaggaactga actggcgaat 540
cgtctggttg atgcacaaac tccatggaaa atcggtggat ttgaagaaga ctcaggtagc 600
cttgaccctg aagttgtcac accaaccatg gcaaactacg caaaatcaat cggtattcgc 660
atctacacca attgcgcagt acgtggtatt gaaacggcgg gcggcaaaat ttctgatgtt 720
gtcacagaaa aaggtgcaat caaaacttct cgtgttgttc tgacgggcgg tatttggtcg 780
cgtctgttca tgggtaactt aggcattgat gttccaacac tgaacgttta cctatcacaa 840
cagcgtatta ctggcgtacc aggcgcacca aaaggtaacg tccacttacc taacggtatt 900
cacttccgtg aacaagctga tggtacctac gccgttgcgc cacgtatctt tactagctct 960
atcgtaaaag acagcttcct gttaggacca agattcctac acgtattagg cggcggggaa 1020
ttaccattag agttctctct tggtaaagat ttattcaact ccttcatgat ggcaacgtct 1080
tggaacttag acgagaaaac accttttgaa gagttccgta ccgcaactaa tacaccaaac 1140
aacgaacact tagatggcgt tctggaaaga ctgagaaaag aattcccagt atttaaagag 1200
tctaaagtgg ttgaacgttg gggtggtacc gttgcaccaa cggatgatga aattccaatt 1260
atttcaacaa tcgagcagta tccaggacta gtcatcaaca ccgccacagg ctggggtatg 1320
acggaaagcc ctgcatctgg tcgattaacg gcagaattgt taatgggcga aacaccattt 1380
attgatccta cgccgtataa actttcccgt tttagctaa 1419

<210> SEQ ID NO 12
<211> LENGTH: 472
<212> TYPE: PRT
<213> ORGANISM: Providencia rettgeri

<400> SEQUENCE: 12

```
Met Lys Ile Ser Arg Arg Lys Leu Leu Leu Gly Val Gly Ala Ala Gly
1               5                   10                  15

Val Leu Ala Gly Gly Ala Ala Val Val Pro Met Ile Asn Arg Glu Gly
            20                  25                  30

Arg Phe Glu Ser Thr Lys Ser Arg Val Pro Ala Val Ala Gly Thr Glu
        35                  40                  45

Gly Lys Leu Pro Glu Ser Ala Asp Ala Val Ile Ile Gly Ala Gly Leu
    50                  55                  60

Gln Gly Ile Met Thr Ala Ile Asn Leu Ala Glu Lys Gly Leu Asn Val
65                  70                  75                  80

Val Ile Cys Glu Lys Gly Val Val Gly Gly Glu Gln Ser Gly Arg Ala
                85                  90                  95

Tyr Ser Gln Ile Ile Ser Tyr Lys Thr Ser Pro Ala Ile Phe Pro Leu
            100                 105                 110

His His Tyr Gly Lys Ile Gln Trp Leu Gly Met Asn Glu Lys Ile Gly
        115                 120                 125

Ala Asp Thr Ser Tyr Arg Val Gln Gly Arg Val Glu Val Pro Ser Ser
    130                 135                 140

Glu Glu Asp Leu Glu Ile Ser Arg Ala Trp Ile Lys Ser Ala Ser Glu
145                 150                 155                 160

Asn Pro Gly Phe Asp Thr Pro Leu Arg Thr Arg Met Ile Glu Gly Thr
                165                 170                 175

Glu Leu Ala Asn Arg Leu Val Asp Ala Gln Thr Pro Trp Lys Ile Gly
            180                 185                 190

Gly Phe Glu Glu Asp Ser Gly Ser Leu Asp Pro Glu Val Val Thr Pro
        195                 200                 205

Thr Met Ala Asn Tyr Ala Lys Ser Ile Gly Ile Arg Ile Tyr Thr Asn
    210                 215                 220

Cys Ala Val Arg Gly Ile Glu Thr Ala Gly Gly Lys Ile Ser Asp Val
225                 230                 235                 240

Val Thr Glu Lys Gly Ala Ile Lys Thr Ser Arg Val Val Leu Thr Gly
                245                 250                 255

Gly Ile Trp Ser Arg Leu Phe Met Gly Asn Leu Gly Ile Asp Val Pro
            260                 265                 270

Thr Leu Asn Val Tyr Leu Ser Gln Gln Arg Ile Thr Gly Val Pro Gly
        275                 280                 285

Ala Pro Lys Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Arg Phe Leu His Val Leu
                325                 330                 335

Gly Gly Gly Glu Leu Pro Leu Glu Phe Ser Leu Gly Lys Asp Leu Phe
            340                 345                 350

Asn Ser Phe Met Met Ala Thr Ser Trp Asn Leu Asp Glu Lys Thr Pro
        355                 360                 365

Phe Glu Glu Phe Arg Thr Ala Thr Asn Thr Pro Asn Asn Glu His Leu
    370                 375                 380

Asp Gly Val Leu Glu Arg Leu Arg Lys Glu Phe Pro Val Phe Lys Glu
385                 390                 395                 400

Ser Lys Val Val Glu Arg Trp Gly Gly Thr Val Ala Pro Thr Asp Asp
                405                 410                 415

Glu Ile Pro Ile Ile Ser Thr Ile Glu Gln Tyr Pro Gly Leu Val Ile
```

```
            420                 425                 430

Asn Thr Ala Thr Gly Trp Gly Met Thr Glu Ser Pro Ala Ser Gly Arg
        435                 440                 445

Leu Thr Ala Glu Leu Leu Met Gly Glu Thr Pro Phe Ile Asp Pro Thr
    450                 455                 460

Pro Tyr Lys Leu Ser Arg Phe Ser
465                 470


<210> SEQ ID NO 13
<211> LENGTH: 1041
<212> TYPE: DNA
<213> ORGANISM: Amycolatopsis orientalis

<400> SEQUENCE: 13

atgcagaact ttgaaatcga ccaggtggaa atgtatgttg cagatctgga agcagcagca      60

agcggttgga tggataaata tggttttagc gttgcaagca ccgatcgtag cgcagatcat     120

cgtagcgtta ccctgcgtca gggtccgatt gcactggttc tgaccgaacc gaccagcgat     180

cgtcatccgg cagcaaccta tctgcagacc catggtgatg gtgttgccga tattgcactg     240

cgtaccagtg atgttgcagc agcatttgaa gcagccgttc gtgccggtgc acagccgatt     300

ctggaaccgg gtgaacgtgc agaaggtgtt attaccgcaa ccgttggtgg ttttggtgat     360

gttgttcata ccctgattca gcgtgatacc gttgaaagtc cggaagcatt tcgtggtcgt     420

ggtggtattg atctgctggc aattgatcat tttgccgttt gtctgaatgc cggtgatctg     480

ggtccgaccg ttgattatta tgaacgtgcc ctgggtttca aacaaatctt tgaagaacat     540

attgttgttg gtgcccaggc aatgaatagc accgttgttc agagcgcaag cggtgaagtt     600

accctgaccc tgattgaacc ggataaaacc gcagatccgg gtcagattga tgattttatc     660

aaagaacatc atggtgccgg tgttcagcat attgcattta ccagcgcaga tgcagttcgt     720

gcagttaaag aactgagcgc acgtggtgtt gaatttctga aaacaccgga tacctattat     780

gacctgctgg gtgaacgcat tcagctggaa acccatagcc tggatgacct gcgtgaaacc     840

aaactgctgg cagatgaaga tcatggtggt cagctgtttc agatttttac cgcaagcacc     900

catccgcgta aaaccatctt ttttgaaatt attgaacgtc agggtgcagg cacctttggt     960

agcagcaaca ttaaagcact gtatgaagca gttgaactgg aacgtaccgg tcagagcaaa    1020

ctgggtccgg cacgtcgttg a                                              1041


<210> SEQ ID NO 14
<211> LENGTH: 346
<212> TYPE: PRT
<213> ORGANISM: Amycolatopsis orientalis

<400> SEQUENCE: 14

Met Gln Asn Phe Glu Ile Asp Gln Val Glu Met Tyr Val Ala Asp Leu
1               5                   10                  15

Glu Ala Ala Ala Ser Gly Trp Met Asp Lys Tyr Gly Phe Ser Val Ala
            20                  25                  30

Ser Thr Asp Arg Ser Ala Asp His Arg Ser Val Thr Leu Arg Gln Gly
        35                  40                  45

Pro Ile Ala Leu Val Leu Thr Glu Pro Thr Ser Asp Arg His Pro Ala
    50                  55                  60

Ala Thr Tyr Leu Gln Thr His Gly Asp Gly Val Ala Asp Ile Ala Leu
65                  70                  75                  80

Arg Thr Ser Asp Val Ala Ala Ala Phe Glu Ala Ala Val Arg Ala Gly
```

```
                85                  90                  95

Ala Gln Pro Ile Leu Glu Pro Gly Glu Arg Ala Glu Gly Val Ile Thr
            100                 105                 110

Ala Thr Val Gly Gly Phe Gly Asp Val Val His Thr Leu Ile Gln Arg
        115                 120                 125

Asp Thr Val Glu Ser Pro Glu Ala Phe Arg Gly Arg Gly Gly Ile Asp
    130                 135                 140

Leu Leu Ala Ile Asp His Phe Ala Val Cys Leu Asn Ala Gly Asp Leu
145                 150                 155                 160

Gly Pro Thr Val Asp Tyr Tyr Glu Arg Ala Leu Gly Phe Lys Gln Ile
                165                 170                 175

Phe Glu Glu His Ile Val Val Gly Ala Gln Ala Met Asn Ser Thr Val
            180                 185                 190

Val Gln Ser Ala Ser Gly Glu Val Thr Leu Thr Leu Ile Glu Pro Asp
        195                 200                 205

Lys Thr Ala Asp Pro Gly Gln Ile Asp Asp Phe Ile Lys Glu His His
    210                 215                 220

Gly Ala Gly Val Gln His Ile Ala Phe Thr Ser Ala Asp Ala Val Arg
225                 230                 235                 240

Ala Val Lys Glu Leu Ser Ala Arg Gly Val Glu Phe Leu Lys Thr Pro
                245                 250                 255

Asp Thr Tyr Tyr Asp Leu Leu Gly Glu Arg Ile Gln Leu Glu Thr His
            260                 265                 270

Ser Leu Asp Asp Leu Arg Glu Thr Lys Leu Leu Ala Asp Glu Asp His
        275                 280                 285

Gly Gly Gln Leu Phe Gln Ile Phe Thr Ala Ser Thr His Pro Arg Lys
    290                 295                 300

Thr Ile Phe Phe Glu Ile Ile Glu Arg Gln Gly Ala Gly Thr Phe Gly
305                 310                 315                 320

Ser Ser Asn Ile Lys Ala Leu Tyr Glu Ala Val Glu Leu Glu Arg Thr
                325                 330                 335

Gly Gln Ser Lys Leu Gly Pro Ala Arg Arg
            340                 345
```

<210> SEQ ID NO 15
<211> LENGTH: 1116
<212> TYPE: DNA
<213> ORGANISM: Streptomyces coelicolor

<400> SEQUENCE: 15

```
atgctgcctc cgtttccgtt tctgcattgg cgtgcagcaa tgcctccgag cgatattgca     60

tatgccgaac tgtatgttgc agatgatcgt gaagcaagcg gttttctggt tgatagcctg    120

ggttttgttc cgctggcagt tgcaggtccg gcaaccggca cccatgatcg tcgtagcacc    180

gttctgcgta gcggtgaagt taccctggtt gttacccagg cactggcacc ggatacaccg    240

gttgcacgtt atgttgaacg tcatggtgat agcattgcag atctggcatt tggttgtgat    300

gatgttcgta gctgttttga tcgtgcagtt ctggcaggcg cagaagcact gcaggcaccg    360

accccgagcc atcgtgcagg tcaggatgca tggtttgcaa ccgttagcgg ttttggtgat    420

attcgtcata cactggttcc ggcagcagat ggtgatggtg caggtctgct gccaccggat    480

cgtgattggg cactgctgcc tgcagcaacc ggtcgcacag gtccgcgtcc gctgctggat    540

catgttgcag tttgtctgga aagcggcacc ctgcgtagta ccgcagaatt ttatgaagca    600

gcatttgata tgccgtatta cagcagcgaa tatattgaag ttggtgaaca ggcaatggat    660
```

```
agtattgttg ttcgtaatgc cggtggtggt attaccttta ccctgattga accggatgat    720

acccgtgttc cgggtcagat tgatcagttt ctgagcgcac atgatggtcc gggtgttcag    780

catctggcct ttctggtgga tgatattgtt ggtagcgttc gtagtctggg tgatcgtggt    840

gttgcatttc tgcgtacacc gggtgcatat tatgatctgc tgaccgaacg tgttggtgca    900

atggcagatg caattgaaga tctgcgtgaa accaatgttc tggccgatcg tgatgaatgg    960

ggttatctgc tgcagatttt tacccgtagc ccgtatccgc gtggcaccct gttttatgaa   1020

tatatccagc gtaatggtgc acgtggtttt ggtagcagca acattaaagc actgtatgaa   1080

gccgttgaac gtgaacgcga agttgccggt cgttga                             1116


<210> SEQ ID NO 16
<211> LENGTH: 371
<212> TYPE: PRT
<213> ORGANISM: Streptomyces coelicolor

<400> SEQUENCE: 16

Met Leu Pro Pro Phe Pro Phe Leu His Trp Arg Ala Ala Met Pro Pro
1               5                   10                  15

Ser Asp Ile Ala Tyr Ala Glu Leu Tyr Val Ala Asp Asp Arg Glu Ala
            20                  25                  30

Ser Gly Phe Leu Val Asp Ser Leu Gly Phe Val Pro Leu Ala Val Ala
        35                  40                  45

Gly Pro Ala Thr Gly Thr His Asp Arg Arg Ser Thr Val Leu Arg Ser
    50                  55                  60

Gly Glu Val Thr Leu Val Val Thr Gln Ala Leu Ala Pro Asp Thr Pro
65                  70                  75                  80

Val Ala Arg Tyr Val Glu Arg His Gly Asp Ser Ile Ala Asp Leu Ala
                85                  90                  95

Phe Gly Cys Asp Asp Val Arg Ser Cys Phe Asp Arg Ala Val Leu Ala
            100                 105                 110

Gly Ala Glu Ala Leu Gln Ala Pro Thr Pro Ser His Arg Ala Gly Gln
        115                 120                 125

Asp Ala Trp Phe Ala Thr Val Ser Gly Phe Gly Asp Ile Arg His Thr
    130                 135                 140

Leu Val Pro Ala Ala Asp Gly Asp Gly Ala Gly Leu Leu Pro Pro Asp
145                 150                 155                 160

Arg Asp Trp Ala Leu Leu Pro Ala Ala Thr Gly Arg Thr Gly Pro Arg
                165                 170                 175

Pro Leu Leu Asp His Val Ala Val Cys Leu Glu Ser Gly Thr Leu Arg
            180                 185                 190

Ser Thr Ala Glu Phe Tyr Glu Ala Ala Phe Asp Met Pro Tyr Tyr Ser
        195                 200                 205

Ser Glu Tyr Ile Glu Val Gly Glu Gln Ala Met Asp Ser Ile Val Val
    210                 215                 220

Arg Asn Ala Gly Gly Gly Ile Thr Phe Thr Leu Ile Glu Pro Asp Asp
225                 230                 235                 240

Thr Arg Val Pro Gly Gln Ile Asp Gln Phe Leu Ser Ala His Asp Gly
                245                 250                 255

Pro Gly Val Gln His Leu Ala Phe Leu Val Asp Asp Ile Val Gly Ser
            260                 265                 270

Val Arg Ser Leu Gly Asp Arg Gly Val Ala Phe Leu Arg Thr Pro Gly
        275                 280                 285
```

```
Ala Tyr Tyr Asp Leu Leu Thr Glu Arg Val Gly Ala Met Ala Asp Ala
    290                 295                 300

Ile Glu Asp Leu Arg Glu Thr Asn Val Leu Ala Asp Arg Asp Glu Trp
305                 310                 315                 320

Gly Tyr Leu Leu Gln Ile Phe Thr Arg Ser Pro Tyr Pro Arg Gly Thr
                325                 330                 335

Leu Phe Tyr Glu Tyr Ile Gln Arg Asn Gly Ala Arg Gly Phe Gly Ser
            340                 345                 350

Ser Asn Ile Lys Ala Leu Tyr Glu Ala Val Glu Arg Glu Arg Glu Val
        355                 360                 365

Ala Gly Arg
    370


<210> SEQ ID NO 17
<211> LENGTH: 1110
<212> TYPE: DNA
<213> ORGANISM: Streptomyces toyocaensis

<400> SEQUENCE: 17

atgggtaccg tgatgagcga actggccatg gcggccgatc cgctggccga tctgtcggtg      60

gactatgtgg agatgtatgt ggaaaacctt gaggcggcag ccctgacgtg ggtggacaag     120

tatgcgttca ccgttgttgg ctccggcgat tttgcggatc atcgcagcac agcgcttcgg     180

catgggcgca ttactctggt actcacggaa gctacctccg atgaacacgt cgctagcaca     240

tacgttgcct cgcatggtga cggagttgct gacattgcgc tgcgcactgc tgatgttacg     300

gcggcatttg acgcagcagt agccaatggt gcgcgtgtgc atcggcctcc gaccccgcat     360

ggtggcgacg gtccggcggt cacagcagtt ctgcatggct tcggtgacgt cgtgcacacg     420

ctggtacaac gtgcacctgg agaagaaccg ggttaccag cagggttttc tccgattagt      480

cgtaccggcg atgggccagc tggtgtggat ctgctggatc tcgaccacat cgccgtgtgc     540

ttgaacactg gcgatttaga cccgacagtc gatcactatt tgacggcatt cggctttcgt     600

cgcattttcg aggaacgcat tgtggtcggt cgccaggcca tggaatccgc ggtagttcag     660

agtccgagtg gaagcgtgac cttgactctc atccaacccg atccttctgc cgatccgggt     720

cagatcgacg agtttctgaa agcgcatcag ggtgccggcg ttcagcattt ggcgttttca     780

tcacccgatg cagtccgctc agtccgcgcg ttagcagatc gtggcgttac ctttcttacg     840

actccgcagg cttactacga tcttctgggt gagcgcattg ccctgtcgga atctcgcgta     900

gacgatctgc gcgctaccaa tgtgctggtc gatgaggatc atggcgggca gctgtttcag     960

atctttaccg ccagcaccca cttacgccac accctgttct tcgaagtgat tgaacgtcaa    1020

ggcgcggaaa cgttcggaag cgcgaacatc aaagcgctgt atgaggccgt agaactcgaa    1080

cgtaccggcc aacgtggccc acgtcaataa                                     1110


<210> SEQ ID NO 18
<211> LENGTH: 369
<212> TYPE: PRT
<213> ORGANISM: Streptomyces toyocaensis

<400> SEQUENCE: 18

Met Gly Thr Val Met Ser Glu Leu Ala Met Ala Ala Asp Pro Leu Ala
1               5                   10                  15

Asp Leu Ser Val Asp Tyr Val Glu Met Tyr Val Glu Asn Leu Glu Ala
            20                  25                  30

Ala Ala Leu Thr Trp Val Asp Lys Tyr Ala Phe Thr Val Val Gly Ser
```

```
        35                  40                  45

Gly Asp Phe Ala Asp His Arg Ser Thr Ala Leu Arg His Gly Arg Ile
    50                  55                  60

Thr Leu Val Leu Thr Glu Ala Thr Ser Asp Glu His Val Ala Ser Thr
65                  70                  75                  80

Tyr Val Ala Ser His Gly Asp Gly Val Ala Asp Ile Ala Leu Arg Thr
                85                  90                  95

Ala Asp Val Thr Ala Ala Phe Asp Ala Ala Val Ala Asn Gly Ala Arg
            100                 105                 110

Val His Arg Pro Pro Thr Pro His Gly Gly Asp Gly Pro Ala Val Thr
        115                 120                 125

Ala Val Leu His Gly Phe Gly Asp Val Val His Thr Leu Val Gln Arg
    130                 135                 140

Ala Pro Gly Glu Glu Pro Gly Leu Pro Ala Gly Phe Ser Pro Ile Ser
145                 150                 155                 160

Arg Thr Gly Asp Gly Pro Ala Gly Val Asp Leu Leu Asp Leu Asp His
                165                 170                 175

Ile Ala Val Cys Leu Asn Thr Gly Asp Leu Asp Pro Thr Val Asp His
            180                 185                 190

Tyr Leu Thr Ala Phe Gly Phe Arg Arg Ile Phe Glu Glu Arg Ile Val
        195                 200                 205

Val Gly Arg Gln Ala Met Glu Ser Ala Val Val Gln Ser Pro Ser Gly
    210                 215                 220

Ser Val Thr Leu Thr Leu Ile Gln Pro Asp Pro Ser Ala Asp Pro Gly
225                 230                 235                 240

Gln Ile Asp Glu Phe Leu Lys Ala His Gln Gly Ala Gly Val Gln His
                245                 250                 255

Leu Ala Phe Ser Ser Pro Asp Ala Val Arg Ser Val Arg Ala Leu Ala
            260                 265                 270

Asp Arg Gly Val Thr Phe Leu Thr Thr Pro Gln Ala Tyr Tyr Asp Leu
        275                 280                 285

Leu Gly Glu Arg Ile Ala Leu Ser Glu Ser Arg Val Asp Asp Leu Arg
    290                 295                 300

Ala Thr Asn Val Leu Val Asp Glu Asp His Gly Gly Gln Leu Phe Gln
305                 310                 315                 320

Ile Phe Thr Ala Ser Thr His Leu Arg His Thr Leu Phe Phe Glu Val
                325                 330                 335

Ile Glu Arg Gln Gly Ala Glu Thr Phe Gly Ser Ala Asn Ile Lys Ala
            340                 345                 350

Leu Tyr Glu Ala Val Glu Leu Glu Arg Thr Gly Gln Arg Gly Pro Arg
        355                 360                 365

Gln
```

<210> SEQ ID NO 19
<211> LENGTH: 1074
<212> TYPE: DNA
<213> ORGANISM: Rhodococcus rhodnii

<400> SEQUENCE: 19

```
atgcagaact tcgaaatcga ctatgtggag atgtacgttg aaaaccttga agtagcagca      60

ttttcttggg tggataagta tgcctttgca gttgctggca cgagtcgttc cgccgatcac     120

cgcagcattg cacttcgtca gggtcaagtg accctggtgc tgacagaacc gacttcggat     180

cgccatccgg cagctgcgta tttacagacg catggcgatg gtgtggcgga tattgccatg     240
```

```
gcgacctcag atgtcgcggc ggcgtatgaa gcagccgttc gtgctggtgc cgaagctgtc    300

cgtgctcctg gacagcactc agaagccgct gtcacgaccg cgacaattgg cggctttggg    360

gacgttgtgc acactctgat tcaacgcgac ggtacatctg cggaactgcc acccggtttt    420

accggctcca tggatgtaac gaaccatggc aaaggggatg tcgatttgct gggtatcgac    480

cactttgcga tttgcctgaa tgcgggcgat ttaggcccga ctgtggagta ctatgaacgt    540

gcgctgggtt ttcgccagat cttcgacgaa cacatcgtag ttggcgccca agcgatgaac    600

agcaccgtcg ttcagagcgc ctctggtgcg gtgacgttaa ccctgattga acctgatcgc    660

aatgccgatc cagggcagat tgacgagttc ctgaaagatc atcaaggtgc cggagtgcag    720

cacattgcgt tcaatagcaa cgatgcagta cgcgccgtta aagccctgag tgagcgtggc    780

gtggaatttc tgaaaacacc gggagcgtat tacgacttgc tgggtgagcg cattacgctc    840

cagacccata gcctcgatga ccttcgtgcg accaatgtct tggcagatga ggaccatgga    900

ggccaactgt ttcagatctt cactgcgtcg acccatccgc ggcataccat cttcttcgaa    960

gtgattgagc gccaaggggc cgggacgttt ggctcgtcca acatcaaagc tctctacgaa   1020

gctgttgaac tggaacgcac cggtcagagt gaatttggcg cagcacgccg gtaa         1074
```

```
<210> SEQ ID NO 20
<211> LENGTH: 357
<212> TYPE: PRT
<213> ORGANISM: Rhodococcus rhodnii

<400> SEQUENCE: 20

Met Gln Asn Phe Glu Ile Asp Tyr Val Glu Met Tyr Val Glu Asn Leu
1               5                   10                  15

Glu Val Ala Ala Phe Ser Trp Val Asp Lys Tyr Ala Phe Ala Val Ala
            20                  25                  30

Gly Thr Ser Arg Ser Ala Asp His Arg Ser Ile Ala Leu Arg Gln Gly
        35                  40                  45

Gln Val Thr Leu Val Leu Thr Glu Pro Thr Ser Asp Arg His Pro Ala
    50                  55                  60

Ala Ala Tyr Leu Gln Thr His Gly Asp Gly Val Ala Asp Ile Ala Met
65                  70                  75                  80

Ala Thr Ser Asp Val Ala Ala Ala Tyr Glu Ala Ala Val Arg Ala Gly
                85                  90                  95

Ala Glu Ala Val Arg Ala Pro Gly Gln His Ser Glu Ala Ala Val Thr
            100                 105                 110

Thr Ala Thr Ile Gly Gly Phe Gly Asp Val Val His Thr Leu Ile Gln
        115                 120                 125

Arg Asp Gly Thr Ser Ala Glu Leu Pro Pro Gly Phe Thr Gly Ser Met
    130                 135                 140

Asp Val Thr Asn His Gly Lys Gly Asp Val Asp Leu Leu Gly Ile Asp
145                 150                 155                 160

His Phe Ala Ile Cys Leu Asn Ala Gly Asp Leu Gly Pro Thr Val Glu
                165                 170                 175

Tyr Tyr Glu Arg Ala Leu Gly Phe Arg Gln Ile Phe Asp Glu His Ile
            180                 185                 190

Val Val Gly Ala Gln Ala Met Asn Ser Thr Val Val Gln Ser Ala Ser
        195                 200                 205

Gly Ala Val Thr Leu Thr Leu Ile Glu Pro Asp Arg Asn Ala Asp Pro
    210                 215                 220
```

```
Gly Gln Ile Asp Glu Phe Leu Lys Asp His Gln Gly Ala Gly Val Gln
225                 230                 235                 240

His Ile Ala Phe Asn Ser Asn Asp Ala Val Arg Ala Val Lys Ala Leu
                245                 250                 255

Ser Glu Arg Gly Val Glu Phe Leu Lys Thr Pro Gly Ala Tyr Tyr Asp
            260                 265                 270

Leu Leu Gly Glu Arg Ile Thr Leu Gln Thr His Ser Leu Asp Asp Leu
        275                 280                 285

Arg Ala Thr Asn Val Leu Ala Asp Glu Asp His Gly Gly Gln Leu Phe
    290                 295                 300

Gln Ile Phe Thr Ala Ser Thr His Pro Arg His Thr Ile Phe Phe Glu
305                 310                 315                 320

Val Ile Glu Arg Gln Gly Ala Gly Thr Phe Gly Ser Ser Asn Ile Lys
                325                 330                 335

Ala Leu Tyr Glu Ala Val Glu Leu Glu Arg Thr Gly Gln Ser Glu Phe
            340                 345                 350

Gly Ala Ala Arg Arg
        355
```

<210> SEQ ID NO 21
<211> LENGTH: 1062
<212> TYPE: DNA
<213> ORGANISM: Actinoplanes teichomyceticus

<400> SEQUENCE: 21

```
atgaccatga cgggccactt tcaggacctg acagtggatc atgtccgcat ttactgcgca      60

gacctggacc ccttgattgc acagtttggc tcctatggtc tggatgtccg tgccgaaggt     120

gtaggcccgg gagcagagca tagcgtggtc ttgggccatg gggacattcg cctggttctg     180

acacggccgg gtactggcga tcaccctggt ggcatgtata ccgcccaaca tggctacgga     240

gtttcggaca ttgcattagg cacagcggat gctgcgggcg cttttcacga ggcggtacgt     300

cgtggggcac gtccgattgc ggcgccagag cgtaccgccg gtgtggttac ggccagtgtt     360

gcgggttttg gcgatgtgat ccatacettt gtacagcgtg aaccaggagg cccttggtcg     420

ctcccgggtc tgaatccggt gcatcgcccg ggtactccgg ggattggact gcgcctggtg     480

gatcactttg ccgtttgtgt cgaagcaggg cgcttaaccg aagtggtgga acactacgaa     540

cgcgttttcg gcttttctgc catcttcacc gaacgcatcg tggttggaga acaagcgatg     600

gattcccagg tggttcaaag tgccggtggg gctgtgacct taacggtcat tgcgccggat     660

accacacgcc gtccgggtca gatcgatacc ttcctgaagg atcatggcgg tcccggtgtc     720

cagcacattg cgtttgaaac ggatgatgtc acccgttcag ttggcgccat gtctgacgct     780

ggtattgagt tccttacgac tccagcagcg tactatgagc ggcttcgcga tcgccttcaa     840

ctcacgcgcc atagcgtgac cgaactgagc cgcctgaacg tattggctga cgaagatcac     900

gacggccaac tctatcagat tttcacgaaa agcactcatc ctcgcgggac cctgttcttt     960

gagatcatcg aacgtgtagg tgcccgcact ttcggttcag gcaacatcaa agcgctgtat    1020

gaagcggtgg aactggacca ggctgccgcg gatggccgtt aa                       1062
```

<210> SEQ ID NO 22
<211> LENGTH: 353
<212> TYPE: PRT
<213> ORGANISM: Actinoplanes teichomyceticus

<400> SEQUENCE: 22

```
Met Thr Met Thr Gly His Phe Gln Asp Leu Thr Val Asp His Val Arg
1               5                   10                  15

Ile Tyr Cys Ala Asp Leu Asp Pro Leu Ile Ala Gln Phe Gly Ser Tyr
            20                  25                  30

Gly Leu Asp Val Arg Ala Glu Gly Val Gly Pro Gly Ala Glu His Ser
        35                  40                  45

Val Val Leu Gly His Gly Asp Ile Arg Leu Val Leu Thr Arg Pro Gly
    50                  55                  60

Thr Gly Asp His Pro Gly Gly Met Tyr Thr Ala Gln His Gly Tyr Gly
65                  70                  75                  80

Val Ser Asp Ile Ala Leu Gly Thr Ala Asp Ala Ala Gly Ala Phe His
                85                  90                  95

Glu Ala Val Arg Arg Gly Ala Arg Pro Ile Ala Ala Pro Glu Arg Thr
            100                 105                 110

Ala Gly Val Val Thr Ala Ser Val Ala Gly Phe Gly Asp Val Ile His
        115                 120                 125

Thr Phe Val Gln Arg Glu Pro Gly Gly Pro Trp Ser Leu Pro Gly Leu
    130                 135                 140

Asn Pro Val His Arg Pro Gly Thr Pro Gly Ile Gly Leu Arg Leu Val
145                 150                 155                 160

Asp His Phe Ala Val Cys Val Glu Ala Gly Arg Leu Thr Glu Val Val
                165                 170                 175

Glu His Tyr Glu Arg Val Phe Gly Phe Ser Ala Ile Phe Thr Glu Arg
            180                 185                 190

Ile Val Val Gly Glu Gln Ala Met Asp Ser Gln Val Val Gln Ser Ala
        195                 200                 205

Gly Gly Ala Val Thr Leu Thr Val Ile Ala Pro Asp Thr Thr Arg Arg
    210                 215                 220

Pro Gly Gln Ile Asp Thr Phe Leu Lys Asp His Gly Gly Pro Gly Val
225                 230                 235                 240

Gln His Ile Ala Phe Glu Thr Asp Asp Val Thr Arg Ser Val Gly Ala
                245                 250                 255

Met Ser Asp Ala Gly Ile Glu Phe Leu Thr Thr Pro Ala Ala Tyr Tyr
            260                 265                 270

Glu Arg Leu Arg Asp Arg Leu Gln Leu Thr Arg His Ser Val Thr Glu
        275                 280                 285

Leu Ser Arg Leu Asn Val Leu Ala Asp Glu Asp His Asp Gly Gln Leu
    290                 295                 300

Tyr Gln Ile Phe Thr Lys Ser Thr His Pro Arg Gly Thr Leu Phe Phe
305                 310                 315                 320

Glu Ile Ile Glu Arg Val Gly Ala Arg Thr Phe Gly Ser Gly Asn Ile
                325                 330                 335

Lys Ala Leu Tyr Glu Ala Val Glu Leu Asp Gln Ala Ala Ala Asp Gly
            340                 345                 350

Arg
```

<210> SEQ ID NO 23
<211> LENGTH: 1146
<212> TYPE: DNA
<213> ORGANISM: Streptomyces avermitilis

<400> SEQUENCE: 23

```
atgacacaaa ccacccatca cacgcctgat actgcgcgtc aagcggatcc gtttccggtg     60

aaagggatgg acgcggttgt ctttgccgtt gggaatgcga aacaagcggc tcactattat    120
```

```
agcactgcct ttggtatgca gttagtcgcg tatagtggcc cggaaaacgg ctctcgtgaa    180

accgcgagct atgtgctgac aaatggtagt gctcgctttg tactcacttc cgtgattaag    240

ccggccacac catggggtca ctttctggct gaccatgtgg ctgagcatgg tgatggcgtg    300

gttgatctgg ccattgaggt acctgatgcc cgtgccgctc acgcgtatgc gattgaacat    360

ggcgcgcgct ccgttgcaga gccgtatgaa ctgaaagacg aacatgggac ggtcgtactt    420

gcggcgatcg caacctacgg gaaaacccgc catactctgg ttgatcgcac gggctatgat    480

ggtccgtact tgccaggcta tgtcgcagca gcaccgatcg tagaaccgcc agcccatcgt    540

acctttcagg cgattgatca ctgcgtgggg aatgttgaac tgggtcgcat gaacgaatgg    600

gtgggtttct acaacaaagt gatgggattc accaacatga aagagtttgt tggtgacgac    660

attgccaccg agtactcagc actgatgtcg aaagtggtag ctgacggcac tctgaaagtg    720

aaattcccca ttaacgaacc cgctttagcc aagaagaaaa gccaaatcga cgaatatctg    780

gagttctacg gtggagcggg cgttcagcat attgcgctca ataccggcga tattgtcgaa    840

accgttcgca cgatgcgtgc agcaggcgtc cagtttctgg ataccccgga ttcgtactac    900

gatacattgg gtgaatgggt cggtgatacg cgtgtgcctg tggatacgct gcgggagttg    960

aaaatcttag cagatcgcga cgaagatggc tatctgcttc agatctttac caaaccagtc   1020

caggaccgtc cgacggtgtt cttcgaaatc atcgaacgcc acggctctat gggcttcgga   1080

aagggcaact tcaaagccct ctttgaagcc attgaacgcg aacaggagaa acggggaaat   1140

ctgtaa                                                              1146
```

<210> SEQ ID NO 24
<211> LENGTH: 381
<212> TYPE: PRT
<213> ORGANISM: Streptomyces avermitilis

<400> SEQUENCE: 24

```
Met Thr Gln Thr Thr His His Thr Pro Asp Thr Ala Arg Gln Ala Asp
1               5                   10                  15

Pro Phe Pro Val Lys Gly Met Asp Ala Val Val Phe Ala Val Gly Asn
            20                  25                  30

Ala Lys Gln Ala Ala His Tyr Tyr Ser Thr Ala Phe Gly Met Gln Leu
        35                  40                  45

Val Ala Tyr Ser Gly Pro Glu Asn Gly Ser Arg Glu Thr Ala Ser Tyr
    50                  55                  60

Val Leu Thr Asn Gly Ser Ala Arg Phe Val Leu Thr Ser Val Ile Lys
65                  70                  75                  80

Pro Ala Thr Pro Trp Gly His Phe Leu Ala Asp His Val Ala Glu His
                85                  90                  95

Gly Asp Gly Val Val Asp Leu Ala Ile Glu Val Pro Asp Ala Arg Ala
            100                 105                 110

Ala His Ala Tyr Ala Ile Glu His Gly Ala Arg Ser Val Ala Glu Pro
        115                 120                 125

Tyr Glu Leu Lys Asp Glu His Gly Thr Val Val Leu Ala Ala Ile Ala
    130                 135                 140

Thr Tyr Gly Lys Thr Arg His Thr Leu Val Asp Arg Thr Gly Tyr Asp
145                 150                 155                 160

Gly Pro Tyr Leu Pro Gly Tyr Val Ala Ala Ala Pro Ile Val Glu Pro
                165                 170                 175

Pro Ala His Arg Thr Phe Gln Ala Ile Asp His Cys Val Gly Asn Val
```

```
            180                 185                 190

Glu Leu Gly Arg Met Asn Glu Trp Val Gly Phe Tyr Asn Lys Val Met
        195                 200                 205

Gly Phe Thr Asn Met Lys Glu Phe Val Gly Asp Asp Ile Ala Thr Glu
    210                 215                 220

Tyr Ser Ala Leu Met Ser Lys Val Val Ala Asp Gly Thr Leu Lys Val
225                 230                 235                 240

Lys Phe Pro Ile Asn Glu Pro Ala Leu Ala Lys Lys Lys Ser Gln Ile
                245                 250                 255

Asp Glu Tyr Leu Glu Phe Tyr Gly Gly Ala Gly Val Gln His Ile Ala
            260                 265                 270

Leu Asn Thr Gly Asp Ile Val Glu Thr Val Arg Thr Met Arg Ala Ala
        275                 280                 285

Gly Val Gln Phe Leu Asp Thr Pro Asp Ser Tyr Tyr Asp Thr Leu Gly
    290                 295                 300

Glu Trp Val Gly Asp Thr Arg Val Pro Val Asp Thr Leu Arg Glu Leu
305                 310                 315                 320

Lys Ile Leu Ala Asp Arg Asp Glu Asp Gly Tyr Leu Leu Gln Ile Phe
                325                 330                 335

Thr Lys Pro Val Gln Asp Arg Pro Thr Val Phe Phe Glu Ile Ile Glu
            340                 345                 350

Arg His Gly Ser Met Gly Phe Gly Lys Gly Asn Phe Lys Ala Leu Phe
        355                 360                 365

Glu Ala Ile Glu Arg Glu Gln Glu Lys Arg Gly Asn Leu
    370                 375                 380


<210> SEQ ID NO 25
<211> LENGTH: 1077
<212> TYPE: DNA
<213> ORGANISM: Pseudomonas putida

<400> SEQUENCE: 25

atggcggatc tgtacgaaaa tccgatgggc ctgatggggt ttgagttcat tgaactcgct     60

tcaccaaccc cgaataccct tgaacccatc ttcgagatta tggggtttac caaggtggct    120

acccatcgtt ccaaagatgt gcacctgtat cgccaaggcg cgatcaatct gatcctgaac    180

aatgaaccgc attctgttgc ctcgtacttt gccgccgaac acggaccctc tgtatgcggc    240

atggcgtttc gtgtcaaaga tagccagaaa gcctataaac gtgctctcga actgggtgca    300

caaccgattc acatcgagac aggtccgatg gaattgaacc ttccggcgat caaaggaatc    360

ggcggtgcgc cgttatacct gattgaccgc tttggcgaag ggagttccat ttacgatatt    420

gactttgtct ttcttgaagg cgtagaccgt catccggttg gtgcaggcct gaagattatt    480

gaccatctga cgcataacgt ctatcgcggc cgtatggcgt attgggcgaa cttttacgag    540

aagttgttca actttcgtga aattcggtac ttcgatatca agggagaata taccggtctg    600

acgagtaaag cgatgacagc ccctgatggc atgattcgca tcccactgaa tgaagaaagc    660

agcaaagggg ctggtcagat tgaggagttc ctcatgcagt ttaacggtga ggggattcag    720

cacgtggcat tcttatcaga tgacctgatc aaaacttggg accatctcaa atcgatcggc    780

atgcgcttta tgacggcacc tccagacacg tattatgaaa tgctggaagg tcgccttccg    840

aatcacggag aacctgttgg tgaactgcaa gcacgcggga ttctgttaga tggcagtagc    900

gagtccggtg ataaacgctt gctgttacag attttcagcg aaactctgat gggtccggtg    960

ttcttcgaat ttatccagcg caaaggcgat gatggcttcg gtgaaggcaa ctttaaagcc   1020
```

```
ttgtttgaat cgattgagcg cgatcaggtt cggcgtggcg tgctgtctac cgattaa      1077


<210> SEQ ID NO 26
<211> LENGTH: 358
<212> TYPE: PRT
<213> ORGANISM: Pseudomonas putida

<400> SEQUENCE: 26

Met Ala Asp Leu Tyr Glu Asn Pro Met Gly Leu Met Gly Phe Glu Phe
1               5                   10                  15

Ile Glu Leu Ala Ser Pro Thr Pro Asn Thr Leu Glu Pro Ile Phe Glu
            20                  25                  30

Ile Met Gly Phe Thr Lys Val Ala Thr His Arg Ser Lys Asp Val His
        35                  40                  45

Leu Tyr Arg Gln Gly Ala Ile Asn Leu Ile Leu Asn Asn Glu Pro His
    50                  55                  60

Ser Val Ala Ser Tyr Phe Ala Ala Glu His Gly Pro Ser Val Cys Gly
65                  70                  75                  80

Met Ala Phe Arg Val Lys Asp Ser Gln Lys Ala Tyr Lys Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Phe
    130                 135                 140

Leu Glu Gly Val Asp Arg His Pro Val Gly Ala Gly Leu Lys Ile Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ile Arg Tyr Phe Asp
            180                 185                 190

Ile Lys Gly Glu Tyr Thr Gly Leu Thr Ser Lys Ala Met Thr Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Ser Asp Asp Leu Ile Lys Thr Trp Asp His Leu
                245                 250                 255

Lys Ser Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Gly Glu
        275                 280                 285

Leu Gln Ala Arg Gly Ile Leu Leu Asp Gly Ser Ser Glu Ser Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Ser Thr Asp
        355
```

<210> SEQ ID NO 27
<211> LENGTH: 1182
<212> TYPE: DNA
<213> ORGANISM: Pseudomonas putida

<400> SEQUENCE: 27

```
atgagccgca acctgtttaa cgttgaagat tatcgtaaac tggcacagaa acgtctgccg      60

aaaatggttt atgattatct ggaaggtggt gccgaagatg aatatggtgt taaacataac     120

cgtgatgtgt ttcagcagtg gcgttttaaa ccgaaacgcc tggttgatgt tagccgtcgt     180

agtctgcagg cagaagttct gggtaaacgt cagagcatgc cgctgctgat tggtccgacc     240

ggtctgaatg gtgcactgtg gccgaaaggt gatctggcac tggcccaggc agcaaccaaa     300

gcaggtattc cgtttgttct gagcaccgca agcaatatga gcattgagga cctggcacgt     360

cagtgtgatg gtgatctgtg gtttcagctg tatgttattc atcgtgaaat tgcccagggt     420

atggttctga aagcactgca tagcggttat accaccctgg ttctgaccac cgatgttgca     480

gttaatggtt atcgtgaacg tgatctgcat aaccgcttta aaatgccgat gagctatacc     540

ccgaaagtta tgctggatgg ttgtctgcat ccgcgttgga gcctggatct ggttcgtcat     600

ggtatgccgc agctggcaaa ttttgttagc agccagacca gcagcctgga aatgcaggca     660

gcactgatga gccgtcagat ggatgcaagc tttaattggg aagcactgcg ttggctgcgc     720

gatctgtggc ctcataaact gctggttaaa ggtctgctga gcgcagaaga tgcagatcgt     780

tgtattgccg aaggtgccga tggtgttatt ctgagcaatc atggtggtcg tcagctggat     840

tgtgcagtta gcccgatgga agtgctggcc cagagcgttg caaaaaccgg taaaccggtt     900

ctgattgata gcggttttcg tcgtggtagc gatattgtta aagcactggc gctgggtgca     960

gaagcagttc tgctgggtcg tgcaaccctg tatggtctgg cagcacgtgg tgaaaccggt    1020

gttggtgaag ttctgaccct gctgaaagca gatattgatc gtaccctggc gcagattggt    1080

tgtccggata ttaccagcct gagtccggat tatctgcaga gcgaaggtgt taccaatacc    1140

gcaccggttg atcatctgat tggtaaaggc acccatgcat ga                       1182
```

<210> SEQ ID NO 28
<211> LENGTH: 393
<212> TYPE: PRT
<213> ORGANISM: Pseudomonas putida

<400> SEQUENCE: 28

```
Met Ser Arg Asn Leu Phe Asn Val Glu Asp Tyr Arg Lys Leu Ala Gln
1               5                   10                  15

Lys Arg Leu Pro Lys Met Val Tyr Asp Tyr Leu Glu Gly Gly Ala Glu
            20                  25                  30

Asp Glu Tyr Gly Val Lys His Asn Arg Asp Val Phe Gln Gln Trp Arg
        35                  40                  45

Phe Lys Pro Lys Arg Leu Val Asp Val Ser Arg Arg Ser Leu Gln Ala
    50                  55                  60

Glu Val Leu Gly Lys Arg Gln Ser Met Pro Leu Leu Ile Gly Pro Thr
65                  70                  75                  80

Gly Leu Asn Gly Ala Leu Trp Pro Lys Gly Asp Leu Ala Leu Ala Gln
                85                  90                  95

Ala Ala Thr Lys Ala Gly Ile Pro Phe Val Leu Ser Thr Ala Ser Asn
            100                 105                 110

Met Ser Ile Glu Asp Leu Ala Arg Gln Cys Asp Gly Asp Leu Trp Phe
```

```
        115                 120                 125

Gln Leu Tyr Val Ile His Arg Glu Ile Ala Gln Gly Met Val Leu Lys
    130                 135                 140

Ala Leu His Ser Gly Tyr Thr Thr Leu Val Leu Thr Thr Asp Val Ala
145                 150                 155                 160

Val Asn Gly Tyr Arg Glu Arg Asp Leu His Asn Arg Phe Lys Met Pro
                165                 170                 175

Met Ser Tyr Thr Pro Lys Val Met Leu Asp Gly Cys Leu His Pro Arg
            180                 185                 190

Trp Ser Leu Asp Leu Val Arg His Gly Met Pro Gln Leu Ala Asn Phe
        195                 200                 205

Val Ser Ser Gln Thr Ser Ser Leu Glu Met Gln Ala Ala Leu Met Ser
    210                 215                 220

Arg Gln Met Asp Ala Ser Phe Asn Trp Glu Ala Leu Arg Trp Leu Arg
225                 230                 235                 240

Asp Leu Trp Pro His Lys Leu Leu Val Lys Gly Leu Leu Ser Ala Glu
                245                 250                 255

Asp Ala Asp Arg Cys Ile Ala Glu Gly Ala Asp Gly Val Ile Leu Ser
            260                 265                 270

Asn His Gly Gly Arg Gln Leu Asp Cys Ala Val Ser Pro Met Glu Val
        275                 280                 285

Leu Ala Gln Ser Val Ala Lys Thr Gly Lys Pro Val Leu Ile Asp Ser
    290                 295                 300

Gly Phe Arg Arg Gly Ser Asp Ile Val Lys Ala Leu Ala Leu Gly Ala
305                 310                 315                 320

Glu Ala Val Leu Leu Gly Arg Ala Thr Leu Tyr Gly Leu Ala Ala Arg
                325                 330                 335

Gly Glu Thr Gly Val Gly Glu Val Leu Thr Leu Leu Lys Ala Asp Ile
            340                 345                 350

Asp Arg Thr Leu Ala Gln Ile Gly Cys Pro Asp Ile Thr Ser Leu Ser
        355                 360                 365

Pro Asp Tyr Leu Gln Ser Glu Gly Val Thr Asn Thr Ala Pro Val Asp
    370                 375                 380

His Leu Ile Gly Lys Gly Thr His Ala
385                 390


<210> SEQ ID NO 29
<211> LENGTH: 1587
<212> TYPE: DNA
<213> ORGANISM: Pseudomonas putida

<400> SEQUENCE: 29

atggcaagcg ttcatggcac cacctatgaa ctgctgcgtc gtcagggtat tgataccgtt      60

tttggtaatc cgggtagcaa tgaactgccg tttctgaaag attttccgga agattttcgt     120

tatattctgg cactgcaaga agcatgcgtt gttggtattg cagatggtta tgcacaggca     180

agccgtaaac cggcatttat caatctgcat agcgcagcag gcaccggtaa tgcaatgggt     240

gcactgagca atgcatggaa tagccatagt ccgctgattg ttaccgcagg tcagcagacc     300

cgtgcaatga ttggtgttga agcactgctg accaatgttg atgcagcaaa tctgcctcgt     360

ccgctggtta aatggtcata tgaaccggca agcgcagccg aagttccgca tgcaatgagc     420

cgtgcaattc atatggcaag catggcaccg cagggtccgg tttatctgag cgttccgtat     480

gatgattggg ataaagatgc agatccgcag agccatcacc tgtttgatcg tcatgttagc     540
```

```
agcgcagttc gtctgaatga tcaggatctg gaaattctgg ttaaagcact gaatagcgca    600

agcaatccgg caattgttct gggtccggat gtggatgcag ccaatgcaaa tgccgattgt    660

gttcagctgg cagaacgtct gaaagcaccg gtttgggttg caccgagcgc accgcgttgt    720

ccgtttccga cccgtcatcc gtgttttcgt ggtctgatgc ctgcaggtat tgccgcaatt    780

agccagctgc tggaaggtca tgatctggtt ctggttattg gtgcaccggt gtttcgttat    840

catcagtatg atccgggtca gtatctgaaa ccgggtacac gtctgattag cgttacctgt    900

gatccgctgg aagcagcacg tgcaccgatg ggtgatgcaa ttgttgcaga tatcggtgca    960

atggccagcg cactggcaaa tagcgttgaa gaatgtagcc gtccgctgcc gaccgcagca   1020

ccggaacctg caaaagtgga tcaggatgca ggtcgtctgc atccggaaac cgtgtttgat   1080

accctgaatg atatggcacc ggaaaatgcc atttatctga atgaaagtac cagcaccacc   1140

gcacagatgt ggcagcgtct gaatatgcgt aatcctggta gttattactt ttgtgcagcc   1200

ggtggtctgg gttttgcact gcctgcagca attggtgtgc agctggccga gccggaacgt   1260

caggttattg ccgtgattgg tgatggtagc gcaaattata gcattagcgc actgtggacc   1320

gcagcccagt ataacattcc gaccattttt gtgattatga acaatggcac ctatggtgca   1380

ctgcgttggt ttgccggtgt tctggaagcc gaaaacgttc cgggtctgga tgttccgggt   1440

atcgattttt gtgcactggc caaaggttat ggtgttcagg cactgaaagc aaataatctg   1500

gaacagctga aggtagcct gcaagaggca ctgagcgcaa aaggtccggt tctgattgaa   1560

gttagcaccg ttagtccggt taaatga                                        1587
```

<210> SEQ ID NO 30
<211> LENGTH: 528
<212> TYPE: PRT
<213> ORGANISM: Pseudomonas putida

<400> SEQUENCE: 30

```
Met Ala Ser Val His Gly Thr Thr Tyr Glu Leu Leu Arg Arg Gln Gly
1               5                   10                  15

Ile Asp Thr Val Phe Gly Asn Pro Gly Ser Asn Glu Leu Pro Phe Leu
            20                  25                  30

Lys Asp Phe Pro Glu Asp Phe Arg Tyr Ile Leu Ala Leu Gln Glu Ala
        35                  40                  45

Cys Val Val Gly Ile Ala Asp Gly Tyr Ala Gln Ala Ser Arg Lys Pro
    50                  55                  60

Ala Phe Ile Asn Leu His Ser Ala Ala Gly Thr Gly Asn Ala Met Gly
65                  70                  75                  80

Ala Leu Ser Asn Ala Trp Asn Ser His Ser Pro Leu Ile Val Thr Ala
                85                  90                  95

Gly Gln Gln Thr Arg Ala Met Ile Gly Val Glu Ala Leu Leu Thr Asn
            100                 105                 110

Val Asp Ala Ala Asn Leu Pro Arg Pro Leu Val Lys Trp Ser Tyr Glu
        115                 120                 125

Pro Ala Ser Ala Ala Glu Val Pro His Ala Met Ser Arg Ala Ile His
    130                 135                 140

Met Ala Ser Met Ala Pro Gln Gly Pro Val Tyr Leu Ser Val Pro Tyr
145                 150                 155                 160

Asp Asp Trp Asp Lys Asp Ala Asp Pro Gln Ser His His Leu Phe Asp
                165                 170                 175

Arg His Val Ser Ser Ala Val Arg Leu Asn Asp Gln Asp Leu Glu Ile
            180                 185                 190
```

```
Leu Val Lys Ala Leu Asn Ser Ala Ser Asn Pro Ala Ile Val Leu Gly
        195                 200                 205

Pro Asp Val Asp Ala Ala Asn Ala Asn Ala Asp Cys Val Gln Leu Ala
    210                 215                 220

Glu Arg Leu Lys Ala Pro Val Trp Val Ala Pro Ser Ala Pro Arg Cys
225                 230                 235                 240

Pro Phe Pro Thr Arg His Pro Cys Phe Arg Gly Leu Met Pro Ala Gly
                245                 250                 255

Ile Ala Ala Ile Ser Gln Leu Leu Glu Gly His Asp Leu Val Leu Val
            260                 265                 270

Ile Gly Ala Pro Val Phe Arg Tyr His Gln Tyr Asp Pro Gly Gln Tyr
        275                 280                 285

Leu Lys Pro Gly Thr Arg Leu Ile Ser Val Thr Cys Asp Pro Leu Glu
    290                 295                 300

Ala Ala Arg Ala Pro Met Gly Asp Ala Ile Val Ala Asp Ile Gly Ala
305                 310                 315                 320

Met Ala Ser Ala Leu Ala Asn Ser Val Glu Glu Cys Ser Arg Pro Leu
                325                 330                 335

Pro Thr Ala Ala Pro Glu Pro Ala Lys Val Asp Gln Asp Ala Gly Arg
            340                 345                 350

Leu His Pro Glu Thr Val Phe Asp Thr Leu Asn Asp Met Ala Pro Glu
        355                 360                 365

Asn Ala Ile Tyr Leu Asn Glu Ser Thr Ser Thr Thr Ala Gln Met Trp
    370                 375                 380

Gln Arg Leu Asn Met Arg Asn Pro Gly Ser Tyr Tyr Phe Cys Ala Ala
385                 390                 395                 400

Gly Gly Leu Gly Phe Ala Leu Pro Ala Ala Ile Gly Val Gln Leu Ala
                405                 410                 415

Glu Pro Glu Arg Gln Val Ile Ala Val Ile Gly Asp Gly Ser Ala Asn
            420                 425                 430

Tyr Ser Ile Ser Ala Leu Trp Thr Ala Ala Gln Tyr Asn Ile Pro Thr
        435                 440                 445

Ile Phe Val Ile Met Asn Asn Gly Thr Tyr Gly Ala Leu Arg Trp Phe
    450                 455                 460

Ala Gly Val Leu Glu Ala Glu Asn Val Pro Gly Leu Asp Val Pro Gly
465                 470                 475                 480

Ile Asp Phe Cys Ala Leu Ala Lys Gly Tyr Gly Val Gln Ala Leu Lys
                485                 490                 495

Ala Asn Asn Leu Glu Gln Leu Lys Gly Ser Leu Gln Glu Ala Leu Ser
            500                 505                 510

Ala Lys Gly Pro Val Leu Ile Glu Val Ser Thr Val Ser Pro Val Lys
        515                 520                 525
```

<210> SEQ ID NO 31
<211> LENGTH: 1419
<212> TYPE: DNA
<213> ORGANISM: Providencia rettgeri

<400> SEQUENCE: 31

```
atgaaaatct cgagaagaaa gctattatta ggggttggtg ctgctggtgt tttagcaggg      60

ggtgctgcgg ttgttcctat gatcaatcgt gaaggtcgtt ttgaatcgac taaatcacgt     120

gtaccagctg ttgctggcac agaaggcaaa ttaccagagt ctgcagatgc agtcatcatc     180

ggtgccggcc ttcaagggat catgactgca attaaccttg ctgaaaaagg tcttaatgtt     240
```

```
gttatctgtg aaaaaggtgt tgtcggtggt gagcaatcag gccgtgcata tagccaaatt    300
atcagttata agacttcccc agctattttc cctttacacc attacggaaa aattcaatgg    360
cttggcatga acgaaaaaat cggtgctgat accagctacc gtgttcaagg ccgtgttgaa    420
gtaccttcaa gcgaagaaga tttagaaatt tcaagagcct ggattaaatc tgcatctgaa    480
aacccaggtt tcgatacacc tttacgtacc cgtatgattg aaggaactga actggcgaat    540
cgtctggttg atgcacaaac tccatggaaa atcggtggat ttgaagaaga ctcaggtagc    600
cttgaccctg aagttgtcac accaaccatg gcaaactacg caaaatcaat cggtattcgc    660
atctacacca attgcgcagt acgtggtatt gaaacggcgg gcggcaaaat ttctgatgtt    720
gtcacagaaa aaggtgcaat caaaacttct cgtgttgttc tgacgggcgg tatttggtcg    780
cgtctgttca tgggtaactt aggcattgat gttccaacac tgaacgttta cctatcacaa    840
cagcgtatta ctggcgtacc aggcgcacca aaaggtaacg tccacttacc taacggtatt    900
cacttccgtg aacaagctga tggtacctac gccgttgcgc cacgtatctt tactagctct    960
atcgtaaaag acagcttcct gttaggacca agattcctac acgtattagg cggcggggaa   1020
ttaccattag agttctctct tggtaaagat ttattcaact ccttcatgat ggcaacgtct   1080
tggaacttag acgagaaaac accttttgaa gagttccgta ccgcaactaa tacaccaaac   1140
aacgaacact tagatggcgt tctggaaaga ctgagaaaag aattcccagt atttaaagag   1200
tctaaagtgg ttgaacgttg ggtggtaccc gttgcaccaa cggatgatga aattccaatt   1260
atttcaacaa tcgagcagta tccaggacta gtcatcaaca ccgccacagg ctggggtatg   1320
acggaaagcc ctgcatctgg tcgattaacg gcagaattgt taatgggcga aacaccattt   1380
attgatccta cgccgtataa actttcccgt tttagctaa                           1419
```

```
<210> SEQ ID NO 32
<211> LENGTH: 1071
<212> TYPE: DNA
<213> ORGANISM: Amycolatopsis balhimycina

<400> SEQUENCE: 32
```

```
atgacgagcg atagcactgt gcagaatttc gagatcgatt acgttgaaat gtacgtggaa     60
aacctcgaag cagctacctt cacctgggtg gacaaatatg cctttgccgt tgcgggtact    120
gatcgctcgg cagaccatcg ctcggtgacc ttacgtcagg gcccgatcaa actggtcttg    180
accgaaccga cctcagaccg tcatccagcc gcggcgtatt tgcagagcca tggggatgga    240
gtagccgata ttgctcttcg cacaccggat gtcacggcgg cttttgaagc ggcggtgcgt    300
ggtggagccg cagcagtgcg cgaaccagtt cgtctggcag gcgggccgat tgtcacggca    360
acgattggcg ggtttggcga tgtcgtgcat accctgattc agtccggtga agcgacagcc    420
gctgcgcctg aaaccaccgg tcaaggtggc ggcgatgtga acctgttggg tctggaccac    480
ttcgccgttt gcctgaacag tggcgatctg ggtccgactg tcgcgttcta tgagcgggca    540
tttggctttc gccagatctt tgaagaacac atcgtcgttg gccgtcaggc catgaacagc    600
acagtagtgc aatctgcaag tggcgaagtt actctgaccc ttatcgaacc cgattcgaat    660
gccgatcccg gccaaatcga tgagtttctg aaagcgcacc agggcgctgg agtgcaacac    720
attgcgttca atgcagacga cgctgtacgt gcagtacgcg ctctttccgg acgtggcgtt    780
gagttcctca aaacgccggg tacctattac gacatgctgg gtgagcgcat tacattagaa    840
acgcatacgc tcgacgattt acggtctacc aatgtgctgg cggatgagga ccatggtggc    900
```

```
cagctgtttc agattttcgc ggcctcaacg catcctcgcc acaccatttt ctttgagatt    960

atcgaacgcc aaggtgcggg gacctttggg tccagcaaca ttaaggcgct gtatgaagcc   1020

gttgagctgg aacgcactgg ccagagtgaa tttggtgcgg cccgtcgcta a            1071


<210> SEQ ID NO 33
<211> LENGTH: 356
<212> TYPE: PRT
<213> ORGANISM: Amycolatopsis balhimycina

<400> SEQUENCE: 33

Met Thr Ser Asp Ser Thr Val Gln Asn Phe Glu Ile Asp Tyr Val Glu
1               5                   10                  15

Met Tyr Val Glu Asn Leu Glu Ala Ala Thr Phe Thr Trp Val Asp Lys
            20                  25                  30

Tyr Ala Phe Ala Val Ala Gly Thr Asp Arg Ser Ala Asp His Arg Ser
        35                  40                  45

Val Thr Leu Arg Gln Gly Pro Ile Lys Leu Val Leu Thr Glu Pro Thr
    50                  55                  60

Ser Asp Arg His Pro Ala Ala Ala Tyr Leu Gln Ser His Gly Asp Gly
65                  70                  75                  80

Val Ala Asp Ile Ala Leu Arg Thr Pro Asp Val Thr Ala Ala Phe Glu
                85                  90                  95

Ala Ala Val Arg Gly Gly Ala Ala Ala Val Arg Glu Pro Val Arg Leu
            100                 105                 110

Ala Gly Gly Pro Ile Val Thr Ala Thr Ile Gly Gly Phe Gly Asp Val
        115                 120                 125

Val His Thr Leu Ile Gln Ser Gly Glu Ala Thr Ala Ala Ala Pro Glu
    130                 135                 140

Thr Thr Gly Gln Gly Gly Gly Asp Val Asn Leu Leu Gly Leu Asp His
145                 150                 155                 160

Phe Ala Val Cys Leu Asn Ser Gly Asp Leu Gly Pro Thr Val Ala Phe
                165                 170                 175

Tyr Glu Arg Ala Phe Gly Phe Arg Gln Ile Phe Glu Glu His Ile Val
            180                 185                 190

Val Gly Arg Gln Ala Met Asn Ser Thr Val Val Gln Ser Ala Ser Gly
        195                 200                 205

Glu Val Thr Leu Thr Leu Ile Glu Pro Asp Ser Asn Ala Asp Pro Gly
    210                 215                 220

Gln Ile Asp Glu Phe Leu Lys Ala His Gln Gly Ala Gly Val Gln His
225                 230                 235                 240

Ile Ala Phe Asn Ala Asp Asp Ala Val Arg Ala Val Arg Ala Leu Ser
                245                 250                 255

Gly Arg Gly Val Glu Phe Leu Lys Thr Pro Gly Thr Tyr Tyr Asp Met
            260                 265                 270

Leu Gly Glu Arg Ile Thr Leu Glu Thr His Thr Leu Asp Asp Leu Arg
        275                 280                 285

Ser Thr Asn Val Leu Ala Asp Glu Asp His Gly Gly Gln Leu Phe Gln
    290                 295                 300

Ile Phe Ala Ala Ser Thr His Pro Arg His Thr Ile Phe Phe Glu Ile
305                 310                 315                 320

Ile Glu Arg Gln Gly Ala Gly Thr Phe Gly Ser Ser Asn Ile Lys Ala
                325                 330                 335

Leu Tyr Glu Ala Val Glu Leu Glu Arg Thr Gly Gln Ser Glu Phe Gly
            340                 345                 350
```

```
Ala Ala Arg Arg
        355


<210> SEQ ID NO 34
<211> LENGTH: 1044
<212> TYPE: DNA
<213> ORGANISM: Kibdelosporangium aridum

<400> SEQUENCE: 34

atgtacgtgg agaacctcga agtcgcggcc ttctcgtggg tggacaagta tgcatttgcg     60

gttgctggta cctcacgctc agcagaccat cgcagtattg cattacgtca gggacaggtt    120

acgttagtgc tgaccgaacc gactagcgac cgtcatcccg ccgcagcgta cttgcagacc    180

catggcgatg gtgttgccga tattgcgtta gccacatcgg atgtcgctgc cgtctatcaa    240

gccgcagtac gtgccggagc ggaagcggtt cgtgctcccg gtcgccatac cgatgcggaa    300

gtcgttactg ccacgattgg tggctttggc gatgtggtac acaccctgat tcagcgtgat    360

ggcgctactc cggcgttgcc accgggcttt acaggctcct tggacgtcac gcattatggc    420

cgtggggatg tcgatctgct tggcattgat cactttgcca tctgcttacc ggctggtgat    480

ctgggcccta ccgttgagta ctatgaacgc gcgctgggct ttcggcagat tttcgaggag    540

cacattgtag tgggtgcgca agcgatgaac agcaccgttg tgcagtctgc gagtgcagcg    600

gtaacgctga ctctgatcga accggataag aatgcggacc cagggcagat tgacgagttt    660

ctgaaagacc accaaggagc aggcgtgcaa catgtggcgt tcagcagcaa tgatgccgtc    720

ggagcagtta aagctctgag tcaacgtggg gtggaatttc tgaaaacccc ggggacctat    780

tacgacatgc tgggtgagcg catcaaactc cagacacact ctcttgacga tctgcgcgca    840

accaatgtgc ttgcggatga agatcacggt gggcagctgt tccagatttt caccgcctcc    900

acacatcctc gccatacgat cttcttcgaa gtgatcgaac gccaaggtgc gggcaccttt    960

ggtagcgcaa acatcaaagc tctctatgaa gccgtagaac tggaacggac gggccagtcg   1020

gaatttggtg ccacgcgccg ctaa                                          1044


<210> SEQ ID NO 35
<211> LENGTH: 347
<212> TYPE: PRT
<213> ORGANISM: Kibdelosporangium aridum

<400> SEQUENCE: 35

Met Tyr Val Glu Asn Leu Glu Val Ala Ala Phe Ser Trp Val Asp Lys
1               5                   10                  15

Tyr Ala Phe Ala Val Ala Gly Thr Ser Arg Ser Ala Asp His Arg Ser
            20                  25                  30

Ile Ala Leu Arg Gln Gly Gln Val Thr Leu Val Leu Thr Glu Pro Thr
        35                  40                  45

Ser Asp Arg His Pro Ala Ala Ala Tyr Leu Gln Thr His Gly Asp Gly
    50                  55                  60

Val Ala Asp Ile Ala Leu Ala Thr Ser Asp Val Ala Ala Val Tyr Gln
65                  70                  75                  80

Ala Ala Val Arg Ala Gly Ala Glu Ala Val Arg Ala Pro Gly Arg His
                85                  90                  95

Thr Asp Ala Glu Val Val Thr Ala Thr Ile Gly Gly Phe Gly Asp Val
            100                 105                 110

Val His Thr Leu Ile Gln Arg Asp Gly Ala Thr Pro Ala Leu Pro Pro
        115                 120                 125
```

```
Gly Phe Thr Gly Ser Leu Asp Val Thr His Tyr Gly Arg Gly Asp Val
    130                 135                 140

Asp Leu Leu Gly Ile Asp His Phe Ala Ile Cys Leu Pro Ala Gly Asp
145                 150                 155                 160

Leu Gly Pro Thr Val Glu Tyr Tyr Glu Arg Ala Leu Gly Phe Arg Gln
                165                 170                 175

Ile Phe Glu Glu His Ile Val Val Gly Ala Gln Ala Met Asn Ser Thr
            180                 185                 190

Val Val Gln Ser Ala Ser Ala Ala Val Thr Leu Thr Leu Ile Glu Pro
        195                 200                 205

Asp Lys Asn Ala Asp Pro Gly Gln Ile Asp Glu Phe Leu Lys Asp His
    210                 215                 220

Gln Gly Ala Gly Val Gln His Val Ala Phe Ser Ser Asn Asp Ala Val
225                 230                 235                 240

Gly Ala Val Lys Ala Leu Ser Gln Arg Gly Val Glu Phe Leu Lys Thr
                245                 250                 255

Pro Gly Thr Tyr Tyr Asp Met Leu Gly Glu Arg Ile Lys Leu Gln Thr
            260                 265                 270

His Ser Leu Asp Asp Leu Arg Ala Thr Asn Val Leu Ala Asp Glu Asp
        275                 280                 285

His Gly Gly Gln Leu Phe Gln Ile Phe Thr Ala Ser Thr His Pro Arg
    290                 295                 300

His Thr Ile Phe Phe Glu Val Ile Glu Arg Gln Gly Ala Gly Thr Phe
305                 310                 315                 320

Gly Ser Ala Asn Ile Lys Ala Leu Tyr Glu Ala Val Glu Leu Glu Arg
                325                 330                 335

Thr Gly Gln Ser Glu Phe Gly Ala Thr Arg Arg
            340                 345
```

<210> SEQ ID NO 36
<211> LENGTH: 1071
<212> TYPE: DNA
<213> ORGANISM: Nonomuraea coxensis

<400> SEQUENCE: 36

```
atggaatcac tgccgaccct tgccgttgat tatgtggaga tgtatgtagc cgatctccaa      60

gtcgcaacgt taccgtggac cgaacagtat ggcttcgccg tcgtaggcac agcggatacg     120

gcgggtcgcc gctcagtcgc actgcgtcaa ggtcgcatca cccttgtctt aacacaggcc     180

acaagcgacc gtcatccggc gtcagcgtat gtgcggaccc atggcgatgg tgtggctgat     240

attgcgttgc gtaccccgga tgtagacgct gtctttacgc acgctgttgc tgcgggtgca     300

cggccggttc gcagtccgag ccgtcatcca ggtcccggac cagcttgctc ggcagcgatt     360

ggtggttttg gtgacctcct gcataccctg gtacaacgcg aaccaggcgc gggcccggga     420

cttcctgtgg gtttctctga tgcccctcct gccgggacct ctggcgcgga tgccggggaa     480

ctcctggata ttgaccactt tgcagtgtgt ctgccgactg gagaactgga catcatcacc     540

gacttctaca tcgccaccct gggctttagc gaaacgttca aagaacgcat tgaagttggg     600

actcaggcga tggagtccaa agtggttcag agtgctagtg gcgacgtcac cctgacgctc     660

attgagcccg atccgttagc cgatagtggg cagattgaca tgttcctgga acgtcatgca     720

ggagcgggcg tgcagcacgt ggcgttttcc tcggcagatg ccgtgcgtgc cgtatcgacc     780

ctgagcggcc gtggcgttcg ctttctgtcg actccggaca gctactacga tttgctggaa     840
```

```
agccgcattc tgatccgtga tcacacggtt gatgaactgc gcgcgacagg cttgttagcc    900

gacgaagatc atgctggtca actgtttcag atcttcaccg cgtccactca cccacgtgaa    960

acgctgttct ttgaggtgat tgagcgccgt ggggcccgca cttttggcgg tgcaaacatt   1020

aaggcgttgt atgaggcagt tgaagtggca cgctctcagc aacgcgcgta a            1071


<210> SEQ ID NO 37
<211> LENGTH: 356
<212> TYPE: PRT
<213> ORGANISM: Nonomuraea coxensis

<400> SEQUENCE: 37

Met Glu Ser Leu Pro Thr Leu Ala Val Asp Tyr Val Glu Met Tyr Val
1               5                   10                  15

Ala Asp Leu Gln Val Ala Thr Leu Pro Trp Thr Glu Gln Tyr Gly Phe
            20                  25                  30

Ala Val Val Gly Thr Ala Asp Thr Ala Gly Arg Arg Ser Val Ala Leu
        35                  40                  45

Arg Gln Gly Arg Ile Thr Leu Val Leu Thr Gln Ala Thr Ser Asp Arg
    50                  55                  60

His Pro Ala Ser Ala Tyr Val Arg Thr His Gly Asp Gly Val Ala Asp
65                  70                  75                  80

Ile Ala Leu Arg Thr Pro Asp Val Asp Ala Val Phe Thr His Ala Val
                85                  90                  95

Ala Ala Gly Ala Arg Pro Val Arg Ser Pro Ser Arg His Pro Gly Pro
            100                 105                 110

Gly Pro Ala Cys Ser Ala Ala Ile Gly Gly Phe Gly Asp Leu Leu His
        115                 120                 125

Thr Leu Val Gln Arg Glu Pro Gly Ala Gly Pro Gly Leu Pro Val Gly
    130                 135                 140

Phe Ser Asp Ala Pro Pro Ala Gly Thr Ser Gly Ala Asp Ala Gly Glu
145                 150                 155                 160

Leu Leu Asp Ile Asp His Phe Ala Val Cys Leu Pro Thr Gly Glu Leu
                165                 170                 175

Asp Ile Ile Thr Asp Phe Tyr Ile Ala Thr Leu Gly Phe Ser Glu Thr
            180                 185                 190

Phe Lys Glu Arg Ile Glu Val Gly Thr Gln Ala Met Glu Ser Lys Val
        195                 200                 205

Val Gln Ser Ala Ser Gly Asp Val Thr Leu Thr Leu Ile Glu Pro Asp
    210                 215                 220

Pro Leu Ala Asp Ser Gly Gln Ile Asp Met Phe Leu Glu Arg His Ala
225                 230                 235                 240

Gly Ala Gly Val Gln His Val Ala Phe Ser Ser Ala Asp Ala Val Arg
                245                 250                 255

Ala Val Ser Thr Leu Ser Gly Arg Gly Val Arg Phe Leu Ser Thr Pro
            260                 265                 270

Asp Ser Tyr Tyr Asp Leu Leu Glu Ser Arg Ile Leu Ile Arg Asp His
        275                 280                 285

Thr Val Asp Glu Leu Arg Ala Thr Gly Leu Leu Ala Asp Glu Asp His
    290                 295                 300

Ala Gly Gln Leu Phe Gln Ile Phe Thr Ala Ser Thr His Pro Arg Glu
305                 310                 315                 320

Thr Leu Phe Phe Glu Val Ile Glu Arg Arg Gly Ala Arg Thr Phe Gly
                325                 330                 335
```

```
Gly Ala Asn Ile Lys Ala Leu Tyr Glu Ala Val Glu Val Ala Arg Ser
            340                 345                 350

Gln Gln Arg Ala
        355


<210> SEQ ID NO 38
<211> LENGTH: 963
<212> TYPE: DNA
<213> ORGANISM: Actinoplanes rectilineatus

<400> SEQUENCE: 38

atggacacgc gtgcggaagg tgcgggtccg ggtgctgagc actctgtggt tctcggtcac      60

gacgatatcc gcctcgttct gactcgccca ggcactggcg atcatccggg agaaatgtat     120

gcgacccaac atgggtatgg cgtttccgac attgcgttag gcaccgcgga tgctgctggt     180

gcgtttcacg aagcggttcg tcgcggcgca cgtcccattg ccgcaccgca acgggatggc     240

gcagtagtga ccgcgtctgt tggcgggttt ggggatgtca ttcacacctt tgtccaacgc     300

gatccgggag gtgaatggtc actgccaggt ctgaccccgg ttcatcgtag cggcacaccg     360

ggtattgggc tgcggttggt agaccatttt gccgtatgcg tggaagcggg ccgtttagac     420

gaagttgtcg aacactacga gcgtgtgttc gatttcgcca tggtgtttac tgagcgcatt     480

gtcgtgggcg aacaagcgat ggattcccag gtggttcaga gtgcgggtgg tgcagtgacc     540

ctgaccctga ttgcacccga cacgacacgc cgtcctgggc agatcgacac gtttctgaag     600

gagcatggcg gagctggtgt acagcacatt gcattcgaaa cgggcgacat tattcgtagc     660

gtgggagcca tgagcgatgc tggcgtggag tttctgagta ccccggatgc ctactatggc     720

cgcatgggcg atcgcttaac gctgacccgc catacagtag ccgaactgcg tgggttgaat     780

gtcctggcag atgaggatca tgacggtcag ctttaccaga tcttcaccaa atcgacccat     840

ccacgcggaa cgctgttctt cgagatcatc gaacgcgtcg gtgcccgcac ttttggctcg     900

ggtaacatca aagccttgta tgaagccgtg gaacttgatc aggcggaacc tgatggccgc     960

taa                                                                   963


<210> SEQ ID NO 39
<211> LENGTH: 320
<212> TYPE: PRT
<213> ORGANISM: Actinoplanes rectilineatus

<400> SEQUENCE: 39

Met Asp Thr Arg Ala Glu Gly Ala Gly Pro Gly Ala Glu His Ser Val
1               5                   10                  15

Val Leu Gly His Asp Asp Ile Arg Leu Val Leu Thr Arg Pro Gly Thr
            20                  25                  30

Gly Asp His Pro Gly Glu Met Tyr Ala Thr Gln His Gly Tyr Gly Val
        35                  40                  45

Ser Asp Ile Ala Leu Gly Thr Ala Asp Ala Ala Gly Ala Phe His Glu
    50                  55                  60

Ala Val Arg Arg Gly Ala Arg Pro Ile Ala Ala Pro Gln Arg Asp Gly
65                  70                  75                  80

Ala Val Val Thr Ala Ser Val Gly Gly Phe Gly Asp Val Ile His Thr
                85                  90                  95

Phe Val Gln Arg Asp Pro Gly Gly Glu Trp Ser Leu Pro Gly Leu Thr
            100                 105                 110

Pro Val His Arg Ser Gly Thr Pro Gly Ile Gly Leu Arg Leu Val Asp
        115                 120                 125
```

```
His Phe Ala Val Cys Val Glu Ala Gly Arg Leu Asp Glu Val Val Glu
    130                 135                 140

His Tyr Glu Arg Val Phe Asp Phe Ala Met Val Phe Thr Glu Arg Ile
145                 150                 155                 160

Val Val Gly Glu Gln Ala Met Asp Ser Gln Val Val Gln Ser Ala Gly
                165                 170                 175

Gly Ala Val Thr Leu Thr Leu Ile Ala Pro Asp Thr Thr Arg Arg Pro
            180                 185                 190

Gly Gln Ile Asp Thr Phe Leu Lys Glu His Gly Gly Ala Gly Val Gln
        195                 200                 205

His Ile Ala Phe Glu Thr Gly Asp Ile Ile Arg Ser Val Gly Ala Met
    210                 215                 220

Ser Asp Ala Gly Val Glu Phe Leu Ser Thr Pro Asp Ala Tyr Tyr Gly
225                 230                 235                 240

Arg Met Gly Asp Arg Leu Thr Leu Thr Arg His Thr Val Ala Glu Leu
                245                 250                 255

Arg Gly Leu Asn Val Leu Ala Asp Glu Asp His Asp Gly Gln Leu Tyr
            260                 265                 270

Gln Ile Phe Thr Lys Ser Thr His Pro Arg Gly Thr Leu Phe Phe Glu
        275                 280                 285

Ile Ile Glu Arg Val Gly Ala Arg Thr Phe Gly Ser Gly Asn Ile Lys
    290                 295                 300

Ala Leu Tyr Glu Ala Val Glu Leu Asp Gln Ala Glu Pro Asp Gly Arg
305                 310                 315                 320


<210> SEQ ID NO 40
<211> LENGTH: 1056
<212> TYPE: DNA
<213> ORGANISM: Actinoplanes subtropicus

<400> SEQUENCE: 40

atgacagggc actttcagaa tctgaccgtg gatcacgtgc gcatctattg cgaggagctg     60

gacccgttga tcgcgcagtt tgggtgctat ggtctggatg tgcgcgcaga aggcgctggc    120

ccaggtgccg aacaatccat cgttttaggt catggtgaca ttcgcctggt gttgacccaa    180

ccaggcactg gcgatcatcc cggtgccatg tacaccagtc agcatgggca cggcgtatca    240

gacattgcgc tcggcaccga tgatgcagcc ggtgcgttcc atgaagccgt gcgtcgtggt    300

gcacgtccaa ttgtagctcc cgaacgcaat gcgggactcg taacggccag cgtaggtggc    360

tttggggacg tgattcacac gtttgtggaa cgggaaccgg gtggttcgtg gtcattaccg    420

ggtttagtcc cggttcaacg ccctggtaca cctggggtga acttgcgcct gattgatcat    480

tttgcggtgt gtgtagagcc gggacgtctt gaagaggtcg ttgagcatta tgagcgtgtc    540

tttgatttct cgatgatctt tactgaacgc atcgtggttg gcgaacaagc aatggacagc    600

caggtcgtcc aatctgctgg aggagccgtt acgctgacgg tgattgcgcc ggataccact    660

cgtcgtccgg ggcagattga caccttcctg aaggatcatg gcggcgcggg tgtccagcac    720

gttgcgttcg aaacggatga tgcgattcgc tctgtgggcg tcatgtcgga agccggcatt    780

ggctttctcc acaccccggc aagctattac gaactgatgc ggcatcgcct gcaactgact    840

cgccacagtg ttgcggaact tagctcctta aacgttcttg cagatcagga ccatgacggt    900

cagctgtatc agatcttcac caaatccacg catcctcgtg gcaccctgtt cttcgagatt    960

atcgaacgcg ttggagcacg tacatttggc agcggcaaca tcaaagccct gtacgaagct   1020
```

```
gtggaactgg atcagagtgc ggctgatggc cgctaa                          1056


<210> SEQ ID NO 41
<211> LENGTH: 351
<212> TYPE: PRT
<213> ORGANISM: Actinoplanes subtropicus

<400> SEQUENCE: 41

Met Thr Gly His Phe Gln Asn Leu Thr Val Asp His Val Arg Ile Tyr
1               5                   10                  15

Cys Glu Glu Leu Asp Pro Leu Ile Ala Gln Phe Gly Cys Tyr Gly Leu
            20                  25                  30

Asp Val Arg Ala Glu Gly Ala Gly Pro Gly Ala Glu Gln Ser Ile Val
        35                  40                  45

Leu Gly His Gly Asp Ile Arg Leu Val Leu Thr Gln Pro Gly Thr Gly
    50                  55                  60

Asp His Pro Gly Ala Met Tyr Thr Ser Gln His Gly His Gly Val Ser
65                  70                  75                  80

Asp Ile Ala Leu Gly Thr Asp Asp Ala Ala Gly Ala Phe His Glu Ala
                85                  90                  95

Val Arg Arg Gly Ala Arg Pro Ile Val Ala Pro Glu Arg Asn Ala Gly
            100                 105                 110

Leu Val Thr Ala Ser Val Gly Gly Phe Gly Asp Val Ile His Thr Phe
        115                 120                 125

Val Glu Arg Glu Pro Gly Gly Ser Trp Ser Leu Pro Gly Leu Val Pro
    130                 135                 140

Val Gln Arg Pro Gly Thr Pro Gly Val Asn Leu Arg Leu Ile Asp His
145                 150                 155                 160

Phe Ala Val Cys Val Glu Pro Gly Arg Leu Glu Glu Val Val Glu His
                165                 170                 175

Tyr Glu Arg Val Phe Asp Phe Ser Met Ile Phe Thr Glu Arg Ile Val
            180                 185                 190

Val Gly Glu Gln Ala Met Asp Ser Gln Val Val Gln Ser Ala Gly Gly
        195                 200                 205

Ala Val Thr Leu Thr Val Ile Ala Pro Asp Thr Thr Arg Arg Pro Gly
    210                 215                 220

Gln Ile Asp Thr Phe Leu Lys Asp His Gly Gly Ala Gly Val Gln His
225                 230                 235                 240

Val Ala Phe Glu Thr Asp Asp Ala Ile Arg Ser Val Gly Val Met Ser
                245                 250                 255

Glu Ala Gly Ile Gly Phe Leu His Thr Pro Ala Ser Tyr Tyr Glu Leu
            260                 265                 270

Met Arg His Arg Leu Gln Leu Thr Arg His Ser Val Ala Glu Leu Ser
        275                 280                 285

Ser Leu Asn Val Leu Ala Asp Gln Asp His Asp Gly Gln Leu Tyr Gln
    290                 295                 300

Ile Phe Thr Lys Ser Thr His Pro Arg Gly Thr Leu Phe Phe Glu Ile
305                 310                 315                 320

Ile Glu Arg Val Gly Ala Arg Thr Phe Gly Ser Gly Asn Ile Lys Ala
                325                 330                 335

Leu Tyr Glu Ala Val Glu Leu Asp Gln Ser Ala Ala Asp Gly Arg
            340                 345                 350


<210> SEQ ID NO 42
<211> LENGTH: 1098
```

<212> TYPE: DNA
<213> ORGANISM: Streptomyces rimosus

<400> SEQUENCE: 42

```
atgacggttt cagatagtgc tgccgccacg gcagcggttg gggatctggc aattgattac     60

atcgagatgt atgttgccga tcttgacgcc gcggcatttg catgggtcga caaatacgct    120

tttaccgtcg tcggcactgg tggctctgcc gatcaccgca gcattgcgtt acgccatggc    180

acgattaccc tggtgctcac gaccgctaca tccgatcgcc atccggcgtc tgtgtatgtg    240

gtagatcacg gcgatggggt tgcggacatt gcactgcgta ccgcggacgt tgaaggcgct    300

ttcgctcatg ccgtcgcaaa tggtgcggaa ccgctgcgcc gtccagcccg tcatggtgga    360

gctggtgcag ccgtgaccgc gaccgtgagt ggctttgggg atgtcgtgca tacccttgtc    420

cagcgtggtc cggaagaagg accgggtttg cctgtggggt ttgtggcgac cctgcaatca    480

cgtcagcccg ttccgtcgga agccgggttg ctggaacttg atcacattgc cgtatgcctg    540

aacaatggcg acttagacgg tacagttgcc tattatcgcc gcgctttggg ctttcaggag    600

atctttgagg aacacattgt agtgggtgcg caagcgatgg actcgaaagt ggtgcagtcg    660

cctacaggac gggtgacgtt aactctgatt gaaccggata caaccgctga tcccggtcag    720

atcgacgact tcctcaaatc acaccaagga gcgggcgtac agcatctggc gttttcgtgt    780

gatgacgcag ttcatgcggt ccgcacgtta actggccgtg gtgtggagtt tctgagcagt    840

ccaagcgcgt attatgatct cctgggcgca cgcatccagt tgtctcaaca cagcctggaa    900

gatctgcgct ccaccagcct cctggcggat caggatcatg gcggccaact gttccagatt    960

ttcaccgcca gtacgcatcc gcgccgtacc atcttctacg agattatcga acgtcaaggt   1020

gcggaaactt tcggtagctc caacatcaaa gcactgtacg aagccgtaga actggagaag   1080

aaaggccagc gggtttaa                                                 1098
```

<210> SEQ ID NO 43
<211> LENGTH: 365
<212> TYPE: PRT
<213> ORGANISM: Streptomyces rimosus

<400> SEQUENCE: 43

```
Met Thr Val Ser Asp Ser Ala Ala Ala Thr Ala Ala Val Gly Asp Leu
1               5                   10                  15

Ala Ile Asp Tyr Ile Glu Met Tyr Val Ala Asp Leu Asp Ala Ala Ala
            20                  25                  30

Phe Ala Trp Val Asp Lys Tyr Ala Phe Thr Val Val Gly Thr Gly Gly
        35                  40                  45

Ser Ala Asp His Arg Ser Ile Ala Leu Arg His Gly Thr Ile Thr Leu
    50                  55                  60

Val Leu Thr Thr Ala Thr Ser Asp Arg His Pro Ala Ser Val Tyr Val
65                  70                  75                  80

Val Asp His Gly Asp Gly Val Ala Asp Ile Ala Leu Arg Thr Ala Asp
                85                  90                  95

Val Glu Gly Ala Phe Ala His Ala Val Ala Asn Gly Ala Glu Pro Leu
            100                 105                 110

Arg Arg Pro Ala Arg His Gly Gly Ala Gly Ala Ala Val Thr Ala Thr
        115                 120                 125

Val Ser Gly Phe Gly Asp Val Val His Thr Leu Val Gln Arg Gly Pro
    130                 135                 140

Glu Glu Gly Pro Gly Leu Pro Val Gly Phe Val Ala Thr Leu Gln Ser
```

```
145                 150                 155                 160

Arg Gln Pro Val Pro Ser Glu Ala Gly Leu Leu Glu Leu Asp His Ile
                165                 170                 175

Ala Val Cys Leu Asn Asn Gly Asp Leu Asp Gly Thr Val Ala Tyr Tyr
            180                 185                 190

Arg Arg Ala Leu Gly Phe Gln Glu Ile Phe Glu Glu His Ile Val Val
        195                 200                 205

Gly Ala Gln Ala Met Asp Ser Lys Val Val Gln Ser Pro Thr Gly Arg
    210                 215                 220

Val Thr Leu Thr Leu Ile Glu Pro Asp Thr Thr Ala Asp Pro Gly Gln
225                 230                 235                 240

Ile Asp Asp Phe Leu Lys Ser His Gln Gly Ala Gly Val Gln His Leu
                245                 250                 255

Ala Phe Ser Cys Asp Asp Ala Val His Ala Val Arg Thr Leu Thr Gly
            260                 265                 270

Arg Gly Val Glu Phe Leu Ser Ser Pro Ser Ala Tyr Tyr Asp Leu Leu
        275                 280                 285

Gly Ala Arg Ile Gln Leu Ser Gln His Ser Leu Glu Asp Leu Arg Ser
    290                 295                 300

Thr Ser Leu Leu Ala Asp Gln Asp His Gly Gly Gln Leu Phe Gln Ile
305                 310                 315                 320

Phe Thr Ala Ser Thr His Pro Arg Arg Thr Ile Phe Tyr Glu Ile Ile
                325                 330                 335

Glu Arg Gln Gly Ala Glu Thr Phe Gly Ser Ser Asn Ile Lys Ala Leu
            340                 345                 350

Tyr Glu Ala Val Glu Leu Glu Lys Lys Gly Gln Arg Val
        355                 360                 365
```

<210> SEQ ID NO 44
<211> LENGTH: 1101
<212> TYPE: DNA
<213> ORGANISM: Herpetosiphon aurantiacus

<400> SEQUENCE: 44

```
atgaccagtc cgacttcgct ggataccacc cctcagctgg atgacttcga ttatgttgag      60

ttctatgtgg gtaatgcccg tcaaaccgcc cactttctgc gcacagcgtt cggttttaaa     120

ccgattgcgt atgcgggctt agaaacagga gtacgtgatc gcgcaagcat tctgttgcag     180

caaggtgcca ttcgcctgat cattacggaa gcactcgatc cggaatcccc gattgccgat     240

catgtgaaac tgcatggtga ctccattaag gatatcgcgt ttaccgtggc caacgtgcat     300

agcgcttttg aagccgcagt taaacgggga gctcgtccca tcttagaacc agtaacgatt     360

gaaagtccgc aaggcagcat tatcaaagct accattggga cttatgggga cacgacacac     420

agcctgattc agcgcgtaga tctggcggac aatgcctttc cgcagtttca gccgatcgag     480

aatccagcac acgtcattga tggtggcttt agcgttgtcg atcatgttgc gatctccttg     540

gagccgggtc gcctggctga atgggtggac ttttacatta acgtccttgg cttccaccag     600

tctcacgaag aaaacattgt gactgaatac tctgggatga actcacgtgt ggtgcagaat     660

catgccggta cgatcaaatt ccccatgcag gagccaattc agggcaaacg ccgctcacag     720

gtggaagagt tcttgacctt tcatcatggt gcgggcgctc agcatctggc aatcctcact     780

gacgacatta tccattcgat tcaaacctta cgcgcgaatg gaatcgaatt tgtccgtacc     840

cctgcgacgt actacgaaaa ccttcaagag cgtgttggcc tgattgatga ggacattgcg     900
```

```
atgctccgtg atctgcacat cttggtcgat cgcgatagca gtggttatct gcttcagatc    960

tttaccaaac cgttacagtc gcgtcctacg atgttcttcg aaattatcca acggaagaac   1020

gccattggct tcggctctgg gaacatcaaa gcgctgtttg cagcagttga acgcgaacaa   1080

gcgctgcgcg gcaatctgta a                                             1101


<210> SEQ ID NO 45
<211> LENGTH: 366
<212> TYPE: PRT
<213> ORGANISM: Herpetosiphon aurantiacus

<400> SEQUENCE: 45

Met Thr Ser Pro Thr Ser Leu Asp Thr Thr Pro Gln Leu Asp Asp Phe
1               5                   10                  15

Asp Tyr Val Glu Phe Tyr Val Gly Asn Ala Arg Gln Thr Ala His Phe
            20                  25                  30

Leu Arg Thr Ala Phe Gly Phe Lys Pro Ile Ala Tyr Ala Gly Leu Glu
        35                  40                  45

Thr Gly Val Arg Asp Arg Ala Ser Ile Leu Leu Gln Gln Gly Ala Ile
    50                  55                  60

Arg Leu Ile Ile Thr Glu Ala Leu Asp Pro Glu Ser Pro Ile Ala Asp
65                  70                  75                  80

His Val Lys Leu His Gly Asp Ser Ile Lys Asp Ile Ala Phe Thr Val
                85                  90                  95

Ala Asn Val His Ser Ala Phe Glu Ala Ala Val Lys Arg Gly Ala Arg
            100                 105                 110

Pro Ile Leu Glu Pro Val Thr Ile Glu Ser Pro Gln Gly Ser Ile Ile
        115                 120                 125

Lys Ala Thr Ile Gly Thr Tyr Gly Asp Thr Thr His Ser Leu Ile Gln
    130                 135                 140

Arg Val Asp Leu Ala Asp Asn Ala Phe Pro Gln Phe Gln Pro Ile Glu
145                 150                 155                 160

Asn Pro Ala His Val Ile Asp Gly Gly Phe Ser Val Val Asp His Val
                165                 170                 175

Ala Ile Ser Leu Glu Pro Gly Arg Leu Ala Glu Trp Val Asp Phe Tyr
            180                 185                 190

Ile Asn Val Leu Gly Phe His Gln Ser His Glu Glu Asn Ile Val Thr
        195                 200                 205

Glu Tyr Ser Gly Met Asn Ser Arg Val Val Gln Asn His Ala Gly Thr
    210                 215                 220

Ile Lys Phe Pro Met Gln Glu Pro Ile Gln Gly Lys Arg Arg Ser Gln
225                 230                 235                 240

Val Glu Glu Phe Leu Thr Phe His His Gly Ala Gly Ala Gln His Leu
                245                 250                 255

Ala Ile Leu Thr Asp Asp Ile Ile His Ser Ile Gln Thr Leu Arg Ala
            260                 265                 270

Asn Gly Ile Glu Phe Val Arg Thr Pro Ala Thr Tyr Tyr Glu Asn Leu
        275                 280                 285

Gln Glu Arg Val Gly Leu Ile Asp Glu Asp Ile Ala Met Leu Arg Asp
    290                 295                 300

Leu His Ile Leu Val Asp Arg Asp Ser Ser Gly Tyr Leu Leu Gln Ile
305                 310                 315                 320

Phe Thr Lys Pro Leu Gln Ser Arg Pro Thr Met Phe Phe Glu Ile Ile
                325                 330                 335
```

```
Gln Arg Lys Asn Ala Ile Gly Phe Gly Ser Gly Asn Ile Lys Ala Leu
            340                 345                 350

Phe Ala Ala Val Glu Arg Glu Gln Ala Leu Arg Gly Asn Leu
        355                 360                 365


<210> SEQ ID NO 46
<211> LENGTH: 30
<212> TYPE: DNA
<213> ORGANISM: Artificial Sequence
<220> FEATURE:
<223> OTHER INFORMATION: primer

<400> SEQUENCE: 46

accggaattc taaggaggaa tgcatatgaa                                      30


<210> SEQ ID NO 47
<211> LENGTH: 30
<212> TYPE: DNA
<213> ORGANISM: Artificial Sequence
<220> FEATURE:
<223> OTHER INFORMATION: primer

<400> SEQUENCE: 47

accggagctc ttagctaaaa cgggaaagtt                                      30


<210> SEQ ID NO 48
<211> LENGTH: 30
<212> TYPE: DNA
<213> ORGANISM: Artificial Sequence
<220> FEATURE:
<223> OTHER INFORMATION: primer

<400> SEQUENCE: 48

ctgagaaaag aatttccagt atttaaagag                                      30


<210> SEQ ID NO 49
<211> LENGTH: 30
<212> TYPE: DNA
<213> ORGANISM: Artificial Sequence
<220> FEATURE:
<223> OTHER INFORMATION: primer

<400> SEQUENCE: 49

ctctttaaat actggaaatt cttttctcag                                      30


<210> SEQ ID NO 50
<211> LENGTH: 25
<212> TYPE: DNA
<213> ORGANISM: Artificial Sequence
<220> FEATURE:
<223> OTHER INFORMATION: primer

<400> SEQUENCE: 50

aagcggcagg gtcggaacag gagag                                           25


<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51

catatgcatt cctccttacg gtgttatatg                                      30
```

<210> SEQ ID NO 52
<211> LENGTH: 40
<212> TYPE: DNA
<213> ORGANISM: Artificial Sequence
<220> FEATURE:
<223> OTHER INFORMATION: primer

<400> SEQUENCE: 52
ccgtaaggag gaatgcatat gaccatgacg ggccactttc 40

<210> SEQ ID NO 53
<211> LENGTH: 19
<212> TYPE: DNA
<213> ORGANISM: Artificial Sequence
<220> FEATURE:
<223> OTHER INFORMATION: primer

<400> SEQUENCE: 53
gctagttatt gctcagcgg 19

<210> SEQ ID NO 54
<211> LENGTH: 30
<212> TYPE: DNA
<213> ORGANISM: Artificial Sequence
<220> FEATURE:
<223> OTHER INFORMATION: primer

<400> SEQUENCE: 54
accggagctc attttttcaa tgtgatttta 30

<210> SEQ ID NO 55
<211> LENGTH: 40
<212> TYPE: DNA
<213> ORGANISM: Artificial Sequence
<220> FEATURE:
<223> OTHER INFORMATION: primer

<400> SEQUENCE: 55
ccgtaaggag gaatgcatat gagccgcaac ctgtttaacg 40

<210> SEQ ID NO 56
<211> LENGTH: 30
<212> TYPE: DNA
<213> ORGANISM: Artificial Sequence
<220> FEATURE:
<223> OTHER INFORMATION: primer

<400> SEQUENCE: 56
accgggatcc tcatgcatgg gtgcctttac 30

<210> SEQ ID NO 57
<211> LENGTH: 30
<212> TYPE: DNA
<213> ORGANISM: Artificial Sequence
<220> FEATURE:
<223> OTHER INFORMATION: primer

<400> SEQUENCE: 57
accgctcgag atttttcaa tgtgatttta 30

<210> SEQ ID NO 58
<211> LENGTH: 20
<212> TYPE: DNA
<213> ORGANISM: Artificial Sequence
<220> FEATURE:
<223> OTHER INFORMATION: primer

<400> SEQUENCE: 58
taatacgact cactataggg 20

<210> SEQ ID NO 59
<211> LENGTH: 30
<212> TYPE: DNA
<213> ORGANISM: Artificial Sequence
<220> FEATURE:
<223> OTHER INFORMATION: primer

<400> SEQUENCE: 59
accgctcgag acggccatcc gcggcagcct 30

<210> SEQ ID NO 60
<211> LENGTH: 27
<212> TYPE: DNA
<213> ORGANISM: Artificial Sequence
<220> FEATURE:
<223> OTHER INFORMATION: primer

<400> SEQUENCE: 60
acggtcttag cgccggatac cacacgc 27

<210> SEQ ID NO 61
<211> LENGTH: 27
<212> TYPE: DNA
<213> ORGANISM: Artificial Sequence
<220> FEATURE:
<223> OTHER INFORMATION: primer

<400> SEQUENCE: 61
cggcgctaag accgttaagg tcacagc 27

<210> SEQ ID NO 62
<211> LENGTH: 27
<212> TYPE: DNA
<213> ORGANISM: Artificial Sequence
<220> FEATURE:
<223> OTHER INFORMATION: primer

<400> SEQUENCE: 62
ggcaacgtta aagcgctgta tgaagcg 27

<210> SEQ ID NO 63
<211> LENGTH: 27
<212> TYPE: DNA
<213> ORGANISM: Artificial Sequence
<220> FEATURE:
<223> OTHER INFORMATION: primer

<400> SEQUENCE: 63
cgctttaacg ttgcctgaac cgaaagt 27

<210> SEQ ID NO 64
<211> LENGTH: 29
<212> TYPE: DNA
<213> ORGANISM: Artificial Sequence
<220> FEATURE:
<223> OTHER INFORMATION: primer

<400> SEQUENCE: 64
accggagctc agtggtggtg gtggtggtg 29

<210> SEQ ID NO 65
<211> LENGTH: 32

-continued

```
<212> TYPE: DNA
<213> ORGANISM: Artificial Sequence
<220> FEATURE:
<223> OTHER INFORMATION: primer

<400> SEQUENCE: 65

gaaccggaat tcattttttc aatgtgattt ta                                32


<210> SEQ ID NO 66
<211> LENGTH: 30
<212> TYPE: DNA
<213> ORGANISM: Artificial Sequence
<220> FEATURE:
<223> OTHER INFORMATION: primer

<400> SEQUENCE: 66

atggtcatat ggattcctcc ttacggtgtt                                   30


<210> SEQ ID NO 67
<211> LENGTH: 17
<212> TYPE: DNA
<213> ORGANISM: Artificial Sequence
<220> FEATURE:
<223> OTHER INFORMATION: primer

<400> SEQUENCE: 67

gttttcccag tcacgac                                                 17


<210> SEQ ID NO 68
<211> LENGTH: 17
<212> TYPE: DNA
<213> ORGANISM: Artificial Sequence
<220> FEATURE:
<223> OTHER INFORMATION: primer

<400> SEQUENCE: 68

caggaaacag ctatgac                                                 17
```

METHOD FOR PRODUCING BENZALDEHYDE

This application is a Continuation of, and claims priority under 35 U.S.C. § 120 to International Application PCT/JP2017/000887, filed Jan. 12, 2017, and claims priority therethrough under 35 U.S.C. § 119 to Japanese Patent Application No. 2016-003878, filed Jan. 12, 2016, the entireties of which are both incorporated by reference herein. Also, the Sequence Listing filed electronically herewith is hereby incorporated by reference (File name: 2018-07-11T_US-582_Seq_List; File size: 88 KB; Date recorded: Jul. 11, 2018).

BACKGROUND OF THE INVENTION

Field of the Invention

The present invention relates to a method for producing benzaldehyde by using a microorganism.

BRIEF DESCRIPTION OF THE RELATED ART

Benzaldehyde is an ingredient that has the smell of almond and apricot kernels, and is used as an aromatic by being blended into foods, drinks, perfumes, and so forth. Benzaldehyde is mainly produced by chemical synthesis.

Furthermore, enzymes involved in biosynthesis of benzaldehyde are also known.

Amino acid deaminase (AAD) is known as an enzyme that catalyzes the reaction of oxidatively deaminating an amino acid (EC 1.4.3.2). AAD of *Proteus mirabilis* is known to be able to convert L-phenylalanine into phenylpyruvate (Massad G et al., *Proteus mirabilis* amino acid deaminase: cloning, nucleotide sequence, and characterization of aad. J Bacteriol. 1995 Oct.; 177(20):5878-83). Furthermore, it has been reported that phenylpyruvate can be generated by cultivating *Proteus mirabilis* having AAD in the presence of L-phenylalanine (Massad G et al., *Proteus mirabilis* amino acid deaminase: cloning, nucleotide sequence, and characterization of aad. J Bacteriol. 1995 Oct.; 177(20):5878-83).

4-hydroxymandelate synthase (HMAS) is known as an enzyme that catalyzes the reaction of oxidatively decarboxylating an alpha-keto acid such as 4-hydroxyphenylpyruvate (EC 1.13.11.46). HMAS of *Streptomyces coelicolor* and HMAS of *Streptomyces toyocaensis* have been reported to be able to convert phenylpyruvate into (S)-mandelate (Sun Z et al., Metabolic engineering of the L-phenylalanine pathway in *Escherichia coli* for the production of S- or R-mandelic acid. Microb Cell Fact. 2011 Sep. 13; 10:71; Liu S P et al., Heterologous pathway for the production of L-phenylglycine from glucose by *E. coli*. J Biotechnol. 2014 Sep. 30; 186:91-7). Furthermore, it has been reported that (S)-mandelate can be generated by cultivating *Escherichia coli* introduced with HMAS of *Amycolatopsis orientalis* in the presence of glucose (Sun Z et al., Metabolic engineering of the L-phenylalanine pathway in *Escherichia coli* for the production of S- or R-mandelic acid. Microb Cell Fact. 2011 Sep. 13; 10:71).

(S)-mandelate dehydrogenase (SMDH) is an enzyme that catalyzes the reaction of oxidizing (S)-mandelate to generate benzoylformate. It has been reported that benzoylformate can be generated from (S)-mandelate by using SMDH of *Pseudomonas putida* heterologously-expressed in *E. coli* (Peng Wang et al., Immobilization of (S)-mandelate dehydrogenase and its catalytic performance on stereoselective transformation of mandelic acid. Journal of the Taiwan Institute of Chemical Engineers Volume 45, Issue 3, May 2014, Pages 744-748).

Benzoylformate decarboxylase (BFDC) is an enzyme that catalyzes the reaction of decarboxylating benzoylformate to generate benzaldehyde. It has been reported that benzaldehyde can be generated from benzoylformate by using cells of *Pseudomonas putida* having BFDC (Park, J. K. and Jung, J. Y, Production of benzaldehyde by encapsulated whole-cell benzoylformate decarboxylase, Enzyme Microb Technol, 30, 726-733, 2002).

SUMMARY OF THE INVENTION

It is an aspect of the present invention is to develop a novel technique for producing benzaldehyde by using a microorganism, and thereby provide a method for efficiently producing benzaldehyde.

As a result, it has been found that benzaldehyde can be produced from L-phenylalanine or glucose by using one or more microorganisms having amino acid deaminase, 4-hydroxymandelate synthase, (S)-mandelate dehydrogenase, and benzoylformate decarboxylase.

It is an aspect of the present invention to provide a method for producing benzaldehyde, the method comprising: (A) producing benzaldehyde by using one or more microorganism having one or more benzaldehyde generation enzymes, wherein said benzaldehyde generation enzymes consist of amino acid deaminase, 4-hydroxymandelate synthase, (S)-mandelate dehydrogenase, and benzoylformate decarboxylase, wherein the said one or more microorganisms is one microorganism which has all four of said benzaldehyde generation enzymes, or a plurality of microorganisms comprising all four of said benzaldehyde generation enzymes among said plurality of microorganisms.

It is a further aspect of the present invention to provide the method as described above, wherein said producing is carried out by a method selected from the group consisting of: (a) cultivating the one or more microorganism so that benzaldehyde is produced from a carbon source via fermentation; (b) producing an intermediate of benzaldehyde from a carbon source and then converting said intermediate into benzaldehyde using the one or more microorganisms, and (c) combinations thereof.

It is a further aspect of the present invention to provide the method as described above, wherein benzaldehyde is produced from a carbon source.

It is a further aspect of the present invention to provide the method as described above, wherein benzaldehyde is produced from L-phenylalanine.

It is a further aspect of the present invention to provide the method as described above, wherein said producing comprises: (B) producing benzaldehyde from a carbon source by using the one or more microorganisms, wherein the one or more microorganisms have L-phenylalanine-producing ability; or (C) converting L-phenylalanine into benzaldehyde by using the one or microorganism.

It is a further aspect of the present invention to provide the method as described above, wherein said producing comprises: (B1) cultivating the one or more microorganisms in a culture medium containing a carbon source to generate and accumulate benzaldehyde in the culture medium, wherein the one or more microorganisms have L-phenylalanine-producing ability; (C1) cultivating the one or more microorganisms in a culture medium containing L-phenylalanine to generate and accumulate benzaldehyde in the culture medium; or (C2) allowing cells of the one or more microorganisms to coexist with L-phenylalanine in a reaction mixture to generate and accumulate benzaldehyde in the reaction mixture.

It is a further aspect of the present invention to provide the method as described above, wherein said producing comprises: (D1) a method selected from the group consisting of: (D1a) generating phenylpyruvate, (S)-mandelate, and/or benzoylformate from a carbon source by using a first of said one or more microorganisms, wherein said first of said one or more microorganism is able to catalyze the conversion of L-phenylalanine into phenylpyruvate, (S)-mandelate, and/or benzoylformate, and has L-phenylalanine-producing ability; (D1b) converting L-phenylalanine into phenylpyruvate, (S)-mandelate, and/or benzoylformate by using a first of said one or more microorganisms, wherein said first of said one or more microorganisms is able to catalyze the conversion of L-phenylalanine into phenylpyruvate, (S)-mandelate, and/or benzoylformate; and (D2) converting said phenylpyruvate, (S)-mandelate, and/or benzoylformate generated or converted in the step (D1) into benzaldehyde by using a second of said one or more microorganisms, wherein said second of said one or more microorganisms is able to catalyze the conversion of phenylpyruvate, (S)-mandelate, and/or benzoylformate into benzaldehyde.

It is a further aspect of the present invention to provide the method as described above, wherein said generating of (D1a) is carried out by cultivating said first of said one or more microorganism recited in (D1a), wherein said converting of (D1b) is carried out by using cells of said first of said one or more microorganisms recited in (D1b) or by cultivating said first of said one or more microorganisms used in the steps (D1b), and wherein said converting of (D2) is carried out by using cells of said second of said one or more microorganisms or by cultivating said second of said one or more microorganisms.

It is a further aspect of the present invention to provide the method as described above, wherein said producing comprises: (E1) the method selected from the group consisting of: (E1a) generating benzoylformate from a carbon source by using a first of said one or more microorganism having amino acid deaminase, 4-hydroxymandelate synthase, and (S)-mandelate dehydrogenase, and having L-phenylalanine-producing ability; (E1b) converting L-phenylalanine into benzoylformate by using a first of said one or more microorganism having amino acid deaminase, 4-hydroxymandelate synthase, and (S)-mandelate dehydrogenase; and (E2) converting benzoylformate generated or converted in (E1) into benzaldehyde by using a second microorganism having benzoylformate decarboxylase.

It is a further aspect of the present invention to provide the method as described above, wherein said generating of (E1a) is carried out by cultivating said first of said one or more microorganism recited in (E1a), and wherein said converting of (E1b) is carried out by using cells of said first of said one or more microorganisms recited in (E1b) or by cultivating said first of said one or more microorganisms recited in (E1b), and wherein said converting of (E2) is carried out by using cells of said second microorganism or by cultivating said second microorganism.

It is a further aspect of the present invention to provide the method as described above, wherein said producing comprises: (F1) a method selected from the group consisting of: (F1a) cultivating a first of said one or more microorganisms in a culture medium containing a carbon source to generate and accumulate benzoylformate in the culture medium, wherein said first of said one or more microorganisms has amino acid deaminase, 4-hydroxymandelate synthase, and (S)-mandelate dehydrogenase and has L-phenylalanine-producing ability; and (F1b) cultivating a first of said one or more microorganism in a culture medium containing L-phenylalanine to generate and accumulate benzoylformate in the culture medium, or allowing cells of a first of said one or more microorganisms to coexist with L-phenylalanine in a reaction mixture to generate and accumulate benzoylformate in the reaction mixture, wherein said first of said one or more microorganisms has amino acid deaminase, 4-hydroxymandelate synthase, and (S)-mandelate dehydrogenase; and (F2) cultivating a second microorganism in the culture medium containing benzoylformate generated in (F1) to generate and accumulate benzaldehyde in the culture medium, or allowing cells of a second microorganism to coexist with benzoylformate generated in (F1) in a reaction mixture to generate and accumulate benzaldehyde in the reaction mixture, wherein said second microorganism has benzoylformate decarboxylase.

It is a further aspect of the present invention to provide the method as described above, wherein said producing comprises: (G1) a method selected from the group consisting of: (G1a) generating phenylpyruvate from a carbon source by using a first microorganism having amino acid deaminase and having L-phenylalanine-producing ability; and (G1b) converting L-phenylalanine into phenylpyruvate by using a first microorganism having amino acid deaminase; (G2) converting phenylpyruvate generated or converted in (G1) into (S)-mandelate by using a second microorganism having 4-hydroxymandelate synthase; (G3) converting (S)-mandelate generated in (G2) into benzoylformate by using a third microorganism having (S)-mandelate dehydrogenase; and (G4) converting benzoylformate converted in (G3) into benzaldehyde by using a fourth microorganism having benzoylformate decarboxylase.

It is further aspect of the present invention to provide the method as described above, wherein said generating of (G1a) is carried out by cultivating the first microorganism recited in (G1a), wherein said converting of (G1b) is carried out by using cells of the first microorganism recited in (G1b) or by cultivating the first microorganism recited in (G1b), wherein said converting of (G2) is carried out by using cells of the second microorganism or by cultivating the second microorganism, wherein said converting of (G3) is carried out by using cells of the third microorganism or by cultivating the third microorganism, and wherein said converting of (G4) is carried out by using cells of the fourth microorganism or by cultivating the fourth microorganism.

It is further aspect of the present invention to provide the method as described above, wherein said one or more microorganisms is present in a culture broth or a processed product of a culture broth; or is collected from a culture broth or a processed product of a culture broth.

It is further aspect of the present invention to provide the method as described above, wherein the amino acid deaminase is a protein selected from the group consisting of: (a) a protein comprising the amino acid sequence of SEQ ID NO: 12; (b) a protein comprising the amino acid sequence of SEQ ID NO: 12 but including substitution, deletion, insertion, and/or addition of 1 to 10 amino acid residues, and having amino acid deaminase activity; and (c) a protein comprising an amino acid sequence having an identity of 90% or higher to the amino acid sequence of SEQ ID NO: 12, and having amino acid deaminase activity.

It is a further aspect of the present invention to provide the method as described above, wherein the 4-hydroxymandelate synthase is a protein selected from the group consisting of:

a protein comprising the amino acid sequence of SEQ ID NO: 14, 16, 18, 20, 22, 33, 37, 41, 43, or 45; (b) a protein comprising the amino acid sequence of SEQ ID NO: 14, 16, 18, 20, 22, 33, 37, 41, 43, or 45 but including substitution, deletion, insertion, and/or addition of 1 to 10 amino acid residues, and having 4-hydroxymandelate synthase activity; (c) a protein comprising an amino acid sequence having an identity of 90% or higher to the amino acid sequence of SEQ ID NO: 14, 16, 18, 20, 22, 33, 37, 41, 43, or 45, and having 4-hydroxymandelate synthase activity, and (d) a protein of the above (a), (b), or (c) but having a specific mutation at an amino acid residue selected from the group consisting of T2, M3, G5, Y18, A27, D35, E46, E180, A187, E191, V194, A199, D201, Q206, 1217, D220, T222, G255, F319, G327, 1336, K337, V343, Q347, and combinations thereof; provided that 4-hydroxymandelate synthase cannot be a protein having only the amino acid sequence of SEQ ID NOS: 35 or 39.

It is a further aspect of the present invention to provide the method as described above, wherein the specific mutation is selected from the group consisting of T2N, M3I, G5R, Y18F, A27V, D35G, E46Q, E180K, A187V, E191K, V194G, A199 (S, V), D201N, Q206R, I217(L, V), D220(A, N), T222S, G255D, F319Y, G327(D, S), I336V, K337Q, V343M, Q347L, and combinations thereof.

It is a further aspect of the present invention to provide the method as described above, wherein the specific mutation is selected from the group consisting of M3I/A199S/G255D, Y18F/D220N, A27V/E191K, D35G/E46Q/T222S/I336V, E180K/I217V/D220N, A187V/I217V, A199V/I217V/K337Q, D201N/I217V, I217V/F319Y, and D220A/Q347L.

It is a further aspect of the present invention to provide the method as described above, wherein the (S)-mandelate dehydrogenase is a protein selected from the group consisting of: (a) a protein comprising the amino acid sequence of SEQ ID NO: 28; (b) a protein comprising the amino acid sequence of SEQ ID NO: 28 but including substitution, deletion, insertion, and/or addition of 1 to 10 amino acid residues, and having (S)-mandelate dehydrogenase activity; and (c) a protein comprising an amino acid sequence having an identity of 90% or higher to the amino acid sequence of SEQ ID NO: 28, and having (S)-mandelate dehydrogenase activity.

It is a further aspect of the present invention to provide the method as described above, wherein the benzoylformate decarboxylase is a protein selected from the group consisting of: (a) a protein comprising the amino acid sequence of SEQ ID NO: 30; (b) a protein comprising the amino acid sequence of SEQ ID NO: 30 but including substitution, deletion, insertion, and/or addition of 1 to 10 amino acid residues, and having benzoylformate decarboxylase activity; and (c) a protein comprising an amino acid sequence having an identity of 90% or higher to the amino acid sequence of SEQ ID NO: 30, and having benzoylformate decarboxylase activity.

It is a further aspect of the present invention to provide the method as described above, wherein the one or more microorganisms is a bacterium or yeast.

It is a further aspect of the present invention to provide the method as described above, wherein the one or more microorganism is a bacterium belonging to the family Enterobacteriaceae or a coryneform bacterium.

It is a further aspect of the present invention to provide the method as described above, wherein the one or more microorganism is a bacterium belonging to the genus *Escherichia*.

It is a further aspect of the present invention to provide the method as described above, wherein the one or more microorganism is *Escherichia coli*.

It is a further aspect of the present invention to provide the method as described above, the method further comprising collecting benzaldehyde.

Still other objects, features, and attendant advantages of the present invention will become apparent to those skilled in the art from a reading of the following detailed description of embodiments constructed in accordance therewith.

DETAILED DESCRIPTION OF EXEMPLARY EMBODIMENTS

The method as described herein is a method for producing benzaldehyde using a microorganism having amino acid deaminase (AAD), 4-hydroxymandelate synthase (HMAS), (S)-mandelate dehydrogenase (SMDH), and benzoylformate decarboxylase (BFDC). This microorganism can also be referred to as "microorganism as described herein". These four enzymes, that is, AAD, HMAS, SMDH, and BFDC, are also collectively referred to as "benzaldehyde generation enzymes".

<1> Microorganism of the Present Invention

<1-1> Microorganism Having Four Benzaldehyde Generation Enzymes

The microorganism as described herein can be a microorganism having (harboring) the four benzaldehyde generation enzymes, i.e. AAD, HMAS, SMDH, and BFDC.

The expression "a microorganism has a benzaldehyde generation enzyme" can mean that, specifically, the microorganism expresses and retains the functional benzaldehyde generation enzyme(s). A benzaldehyde generation enzyme is expressed from a gene encoding the benzaldehyde generation enzyme. A gene encoding a benzaldehyde generation enzyme can also be referred to as "benzaldehyde generation enzyme gene". That is, the microorganism as described herein, i.e. a microorganism having the benzaldehyde generation enzymes, has the benzaldehyde generation enzyme genes. The expression "a microorganism has a benzaldehyde generation enzyme" can also be expressed as "a microorganism has a benzaldehyde generation enzyme gene".

The microorganism as described herein may be a single microorganism, or may be a plurality of microorganisms. That is, in the present invention, the term "microorganism" as a singular form, such as "a microorganism" and "the microorganism", may be read as at least one microorganism, for example, either a single microorganism or a plurality of microorganisms, according to the context.

When the microorganism as described herein is a single microorganism, this single microorganism alone has all four benzaldehyde generation enzymes.

When the microorganism as described herein is a plurality of microorganisms, the plurality has all the four benzaldehyde generation enzymes among the plurality. In other words, when the microorganism as described herein is a plurality of microorganisms, the four benzaldehyde generation enzymes can be harbored by any one of the plurality of microorganisms. The benzaldehyde generation enzymes may be harbored by any one of the plurality of microorganisms, or by two or more of the plurality of microorganisms. The plurality of microorganisms each may have any one of the benzaldehyde generation enzymes, or two or more of the benzaldehyde generation enzymes. The kind(s) of the benzaldehyde generation enzyme(s) harbored by each of the plurality of microorganisms is/are not particularly limited, so long as production of benzaldehyde is attained. The kind(s) of the benzaldehyde generation enzyme(s) harbored by each of the plurality of microorganisms can be appropriately chosen depending on the various conditions such as the mode for carrying out the production step, e.g. configuration of substeps in the production step. For example, the microorganism as described herein may be a combination of four microorganisms having the four respective benzaldehyde generation enzymes, i.e. a combination of a microorganism having AAD, a microorganism having HMAS, a microorganism having SMDH, and a microorganism having BFDC. The plurality of microorganisms may be or may not be the same, except for the kind(s) of the benzaldehyde generation enzyme(s) harbored by each of the plurality of microorganisms. For example, the plurality of microorganisms may be or may not be microorganisms of the same genus, species, or strain.

The microorganism as described herein may have L-phenylalanine-producing ability. The term "microorganism having L-phenylalanine-producing ability" can refer to a microorganism that is able to biosynthesize L-phenylalanine upon being cultured in a culture medium, such as a culture medium containing a carbon source. Hence, specifically, the term "microorganism having L-phenylalanine-producing ability" may refer to a microorganism that is able to biosynthesize L-phenylalanine from a carbon source. The biosynthesized L-phenylalanine may be used as a raw material for production of benzaldehyde. Hence, specifically, the term "microorganism having L-phenylalanine-producing ability" may also refer to a microorganism that is able to biosynthesize L-phenylalanine in an amount required as a raw material for production of benzaldehyde. The biosynthesized L-phenylalanine may be or may not be accumulated as a product, for example, in cells of the microorganism and/or the culture medium. That is, the biosynthesized L-phenylalanine may be immediately consumed. For example, the biosynthesized L-phenylalanine may be immediately converted into benzaldehyde or an intermediate thereof. Therefore, in an embodiment, L-phenylalanine-producing ability may be measured on the basis of production of benzaldehyde or an intermediate thereof.

When the microorganism as described herein is a single microorganism, this single microorganism may have L-phenylalanine-producing ability.

When the microorganism as described herein is a plurality of microorganisms, one or more microorganisms of the plurality of microorganisms may have L-phenylalanine-producing ability. Which microorganism(s) of the plurality of microorganisms has/have L-phenylalanine-producing ability is not particularly limited, so long as production of benzaldehyde is attained. For example, a microorganism having at least AAD may have L-phenylalanine-producing ability.

Incidentally, the microorganism as described herein has benzaldehyde-producing ability. The term "microorganism having benzaldehyde-producing ability" can refer to a microorganism that is able to produce benzaldehyde. The term "microorganism having benzaldehyde-producing ability" may refer to a microorganism that is able to produce benzaldehyde by fermentation, bioconversion, or both of these methods. That is, the term "microorganism having benzaldehyde-producing ability" may refer to a microorganism that is able to produce benzaldehyde from a carbon source or L-phenylalanine. Specifically, the term "microorganism having benzaldehyde-producing ability" may refer to a microorganism that is able to, upon being cultured in a culture medium containing a carbon source, produce and accumulate benzaldehyde or an intermediate thereof in the culture medium, which intermediate can further be converted into benzaldehyde. Also, specifically, the term "microorganism having benzaldehyde-producing ability" may refer to a microorganism that is able to, upon being cultured in a culture medium containing L-phenylalanine or upon being allowed to coexist with or act on L-phenylalanine in a reaction mixture, produce and accumulate benzaldehyde or an intermediate thereof in the culture medium or reaction mixture, which intermediate can further be converted into benzaldehyde.

Benzaldehyde can be produced from L-phenylalanine by the action of the four benzaldehyde generation enzymes. Hence, the microorganism as described herein, which has the four benzaldehyde generation enzymes, may be able to produce benzaldehyde from L-phenylalanine. For example, the microorganism as described herein may be able to produce benzaldehyde from L-phenylalanine via a step of producing benzaldehyde by bioconversion, or via a combination of a substep of producing an intermediate of benzaldehyde by bioconversion and subsequent substep(s) of converting the intermediate into benzaldehyde.

When the microorganism as described herein has L-phenylalanine-producing ability, the microorganism may also be able to produce benzaldehyde from a carbon source. For example, the microorganism as described herein may be able to produce benzaldehyde from a carbon source via a step of producing benzaldehyde by fermentation, or via a combination of a substep of producing an intermediate of benzaldehyde by fermentation and subsequent substep(s) of converting the intermediate into benzaldehyde.

The microorganism as described herein may be able to accumulate benzaldehyde in the culture medium or reaction mixture to such a degree that benzaldehyde can be collected therefrom. The microorganism as described herein may be able to accumulate benzaldehyde in the culture medium or reaction mixture in an amount of, for example, 0.01 mM or more, 0.1 mM more, or 1 mM more.

When the microorganism as described herein is a single microorganism, this single microorganism has benzaldehyde-producing ability.

When the microorganism as described herein is a plurality of microorganisms, the plurality has benzaldehyde-producing ability among the plurality.

The microorganism is not particularly limited, so long as it is able to express the functional benzaldehyde generation enzymes, and is able to be used for production of benzaldehyde. Examples of the microorganism can include bacteria and yeast.

Examples of the bacteria can include bacteria belonging to the family Enterobacteriaceae, coryneform bacteria, and *Bacillus* bacteria.

Examples of bacteria belonging to the family Enterobacteriaceae can include bacteria belonging to the genus *Escherichia, Enterobacter, Pantoea, Klebsiella, Serratia, Erwinia, Photorhabdus, Providencia, Salmonella, Morganella*, or the like. Specifically, bacteria classified into the family Enterobacteriaceae according to the taxonomy used in the NCBI (National Center for Biotechnology Information) database (ncbi.nlm.nih.gov/Taxonomy/Browser/wwwtax.cgi?id=91347) can be used. The *Escherichia* bacteria are not particularly limited, and examples thereof can include those classified into the genus *Escherichia* according to the taxonomy known to those skilled in the field of microbiology. Examples of the *Escherichia* bacteria can include, for example, those described in the work of Neidhardt et al. (Backmann B. J., 1996, Derivations and Genotypes of some mutant derivatives of *Escherichia coli* K-12, pp. 2460-2488, Table 1, In F. D. Neidhardt (ed.), *Escherichia coli* and *Salmonella* Cellular and Molecular Biology/Second Edition, American Society for Microbiology Press, Washington, D.C.). Examples of the *Escherichia* bacteria can include, for example, *Escherichia coli*. Specific examples of *Escherichia coli* can include, for example, *Escherichia coli* K-12 strains such as W3110 strain (ATCC 27325) and MG1655 strain (ATCC 47076); *Escherichia coli* K5 strain (ATCC 23506); *Escherichia coli* B strains such as BL21 (DE3) strain; and derivative strains thereof. Examples the *Enterobacter* bacterium can include, for example, *Enterobacter agglomerans* and *Enterobacter aerogenes*. Examples the *Pantoea* bacteria can include, for example, *Pantoea ananatis, Pantoea stewartii, Pantoea agglomerans*, and *Pantoea citrea*. Examples of the *Erwinia* bacteria can include *Erwinia amylovora* and *Erwinia carotovora*. Examples of the *Klebsiella* bacteria can include *Klebsiella planticola*.

Examples of the coryneform bacteria can include bacteria belonging to the genus *Corynebacterium, Brevibacterium, Microbacterium*, or the like.

Specific examples of such coryneform bacteria can include the following species.

*Corynebacterium acetoacidophilum*

*Corynebacterium acetoglutamicum*

*Corynebacterium alkanolyticum*

*Corynebacterium callunae*

*Corynebacterium crenatum*

*Corynebacterium glutamicum*

*Corynebacterium ilium*

*Corynebacterium melassecola*

*Corynebacterium thermoaminogenes* (*Corynebacterium efficiens*)

*Corynebacterium herculis*

*Brevibacterium divaricatum* (*Corynebacterium glutamicum*)

*Brevibacterium flavum* (*Corynebacterium glutamicum*)

*Brevibacterium immariophilum*

*Brevibacterium lactofermentum* (*Corynebacterium glutamicum*)

*Brevibacterium roseum*

*Brevibacterium saccharolyticum*

*Brevibacterium thiogenitalis*

*Corynebacterium ammoniagenes* (*Corynebacterium stationis*)

*Brevibacterium album*

*Brevibacterium cerinum*

*Microbacterium ammoniaphilum*

Specific examples of the coryneform bacteria can include the following strains.

*Corynebacterium acetoacidophilum* ATCC 13870

*Corynebacterium acetoglutamicum* ATCC 15806

*Corynebacterium alkanolyticum* ATCC 21511

*Corynebacterium callunae* ATCC 15991

*Corynebacterium crenatum* AS 1.542

*Corynebacterium glutamicum* ATCC 13020, ATCC 13032, ATCC 13060, ATCC 13869, FERM BP-734

*Corynebacterium lilium* ATCC 15990

*Corynebacterium melassecola* ATCC 17965

*Corynebacterium efficiens* (*Corynebacterium thermoaminogenes*) AJ12340 (FERM BP-1539)

*Corynebacterium herculis* ATCC 13868

*Brevibacterium divaricatum* (*Corynebacterium glutamicum*) ATCC 14020

*Brevibacterium flavum* (*Corynebacterium glutamicum*) ATCC 13826, ATCC 14067, AJ12418 (FERM BP-2205)

*Brevibacterium immariophilum* ATCC 14068

*Brevibacterium lactofermentum* (*Corynebacterium glutamicum*) ATCC 13869

*Brevibacterium roseum* ATCC 13825

*Brevibacterium saccharolyticum* ATCC 14066

*Brevibacterium thiogenitalis* ATCC 19240

*Corynebacterium ammoniagenes* (*Corynebacterium stationis*) ATCC 6871, ATCC 6872

*Brevibacterium album* ATCC 15111

*Brevibacterium cerinum* ATCC 15112

*Microbacterium ammoniaphilum* ATCC 15354

The coryneform bacteria can include bacteria that had previously been classified into the genus *Brevibacterium*, but are presently united into the genus *Corynebacterium* (Int. J. Syst. Bacteriol., 41, 255 (1991)). Moreover, *Corynebacterium stationis* can include bacteria that had previously been classified as *Corynebacterium ammoniagenes*, but is presently re-classified into *Corynebacterium stationis* on the basis of nucleotide sequence analysis of 16S rRNA etc. (Int. J. Syst. Evol. Microbiol., 60, 874-879 (2010)).

Examples of the *Bacillus* bacteria can include, for example, *Bacillus subtilis, Bacillus amyloliquefaciens, Bacillus pumilus, Bacillus licheniformis, Bacillus megaterium, Bacillus brevis, Bacillus polymixa*, and *Bacillus stearothermophilus*. Specific examples of *Bacillus subtilis* can include, for example, the *Bacillus subtilis* 168 Marburg strain (ATCC 6051) and PY79 strain (Plasmid, 1984, 12, 1-9). Specific examples of *Bacillus amyloliquefaciens* can include, for example, the *Bacillus amyloliquefaciens* T strain (ATCC 23842) and N strain (ATCC 23845).

Examples of the yeast can include yeast belonging to the genus *Saccharomyces* such as *Saccharomyces cerevisiae*, the genus *Candida* such as *Candida utilis*, the genus *Pichia* such as *Pichiapastoris*, the genus *Hansenula* such as *Hansenulapolymorpha*, and the genus *Schizosaccharomyces* such as *Schizosaccharomyces pombe*.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. These strains can also be obtained from, for example, the depositories at which the strains were deposited.

Amino acid deaminase (AAD) is known as an enzyme that catalyzes the reaction of oxidatively deaminating an amino acid (EC 1.4.3.2). AAD uses at least L-phenylalanine as a substrate. AAD may or may not use any other amino acid as a substrate, so long as it uses L-phenylalanine as a substrate. That is, the term "AAD" can refer to a protein that has the activity of catalyzing the reaction of oxidatively deaminating L-phenylalanine to generate phenylpyruvate, i.e. the reaction of generating phenylpyruvate, $H_2O_2$, and ammonia from L-phenylalanine, $H_2O$, and oxygen. This activity can also be referred to as "AAD activity". A gene encoding AAD can also be referred to as "AAD gene". AAD can also be referred to as "amino acid oxidase" or "L-phenylalanine oxidase". Examples of AAD can include AADs of *Providencia* bacteria such as *Providencia rettgeri* (WO2009/028338), AADs of *Proteus* bacteria such as *Proteus mirabilis* (Massad G et al., *Proteus mirabilis* amino acid deaminase: cloning, nucleotide sequence, and characterization of aad. J Bacteriol. 1995 Oct.; 177(20):5878-83.), and AADs of other various organisms. Examples of *Providencia rettgeri* can include the *Providencia rettgeri* AJ2770 strain (FERM BP-941) and IFO13501 strain. The nucleotide sequence of the AAD gene of the *Providencia rettgeri* AJ2770 strain (FERM BP-941) is shown as SEQ ID NO: 11, and the amino acid sequence of AAD encoded by this gene is shown as SEQ ID NO: 12. The AAD gene of SEQ ID NO: 11 is a modified-type AAD gene that is used in Examples section. The nucleotide sequence of the wild-type AAD gene of the *Providencia rettgeri* AJ2770 strain (FERM BP-941) is shown as SEQ ID NO: 31. The amino acid sequence of AAD encoded by this wild-type AAD gene is identical to that of AAD encoded by this modified-type AAD gene, i.e. SEQ ID NO: 12. The microorganism as described herein may have one kind of AAD, or two or more kinds of AADs.

The AAD activity can be measured by, for example, incubating the enzyme with the substrate, such as L-phenylalanine, in the presence of oxygen, and measuring the enzyme- and substrate-dependent generation of the product, i.e. phenylpyruvate (Massad G et al., *Proteus mirabilis* amino acid deaminase: cloning, nucleotide sequence, and characterization of aad. J Bacteriol. 1995 Oct.; 177(20): 5878-83.). The generation of phenylpyruvate can be measured by, for example, measuring coloration due to complex formation between phenylpyruvate and ferric ion as an increase in absorbance at 614 nm.

4-hydroxymandelate synthase (HMAS) is known as an enzyme that catalyzes the reaction of oxidatively decarboxylating an alpha-keto acid such as 4-hydroxyphenylpyruvate (EC 1.13.11.46). HMAS uses at least phenylpyruvate as a substrate. HMAS may or may not use any other alpha-keto acid such as 4-hydroxyphenylpyruvate as a substrate, so long as it uses phenylpyruvate as a substrate. That is, the term "HMAS" can refer to a protein that has the activity of catalyzing the reaction of oxidatively decarboxylating phenylpyruvate to generate (S)-mandelate, i.e. the reaction of generating (S)-mandelate and $CO_2$ from phenylpyruvate and oxygen.

This activity can also be referred to as "HMAS activity". A gene encoding HMAS can also be referred to as "HMAS gene". Examples of HMAS can include HMASs of *Amycolatopsis* bacteria such as *Amycolatopsis orientalis* and *Amycolatopsis balhimycina*, HMASs of *Streptomyces* bacteria such as *Streptomyces coelicolor, Streptomyces toyocaensis*, and *Streptomyces rimosus*, HMASs of *Rhodococcus* bacteria such as *Rhodococcus rhodnii*, HMASs of *Actinoplanes* bacteria such as *Actinoplanes teichomyceticus, Actinoplanes rectilineatus*, and *Actinoplanes subtropicus*, HMASs of *Kibdelosporangium* bacteria such as *Kibdelosporangium aridum*, HMASs of *Nonomuraea* bacteria such as *Nonomuraea coxensis*, HMASs of *Herpetosiphon* bacteria such as *Herpetosiphon aurantiacus*, and HMASs of other various organisms. The nucleotide sequences of the HMAS genes (codon-optimized for expression in *E. coli*) of *Amycolatopsis orientalis, Streptomyces coelicolor, Streptomyces toyocaensis, Rhodococcus rhodnii, Actinoplanes teichomyceticus, Amycolatopsis balhimycina, Kibdelosporangium aridum, Nonomuraea coxensis, Actinoplanes rectilineatus, Actinoplanes subtropicus, Streptomyces rimosus*, and *Herpetosiphon aurantiacus* are shown as SEQ ID NOS: 13, 15, 17, 19, 21, 32, 34, 37, 38, 40, 42, and 44, respectively, and the amino acid sequences of HMASs encoded by these genes are shown as SEQ ID NOS: 14, 16, 18, 20, 22, 33, 35, 37, 39, 41, 43, and 45, respectively. The microorganism as described herein may have one kind of HMAS, or two or more kinds of HMASs. In an embodiment, HMASs having the amino acid sequences shown as 35 and 39 may be excluded from HMAS. In another embodiment, HMASs having the amino acid sequences shown as 14, 16, 35, and 39 may be excluded from HMAS. Similarly, HMAS genes encoding HMASs having the amino acid sequences shown as 35 and 39, or the amino acid sequences shown as 14, 16, 35, and 39 may be excluded from the HMAS gene.

The HMAS activity can be measured by, for example, incubating the enzyme with the substrate, such as phenylpyruvate in the presence of oxygen, and measuring the enzyme- and substrate-dependent generation of the product, i.e. (S)-mandelate (Sun Z et al., Metabolic engineering of the L-phenylalanine pathway in *Escherichia coli* for the production of S- or R-mandelic acid. Microb Cell Fact. 2011 Sep. 13; 10:71.).

The term "(S)-mandelate dehydrogenase (SMDH)" can refer to a protein that has the activity of catalyzing the reaction of oxidizing (S)-mandelate to generate benzoylformate (EC 1.1.99.31). This activity can also be referred to as "SMDH activity". A gene encoding SMDH can also be referred to as "SMDH gene". Examples of SMDH can include MdlB proteins encoded by mdlB genes of *Pseudomonas* bacteria such as *Pseudomonas putida*, and SMDHs of other various organisms. The nucleotide sequence of the mdlB gene (SMDH gene) of *Pseudomonas putida* is shown as SEQ ID NO: 27, and the amino acid sequence of MdlB protein (SMDH) encoded by this gene is shown as SEQ ID NO: 28. The microorganism as described herein may have one kind of SMDH, or two or more kinds of SMDHs.

The SMDH activity can be measured by, for example, incubating the enzyme with the substrate, such as (S)-mandelate, in the presence of NAD, and measuring the enzyme- and substrate-dependent reduction of NAD (B. S. Al-Baharna and R. Y Hamzah, Aerobic metabolism of mandelates by *Burkholderia cepacia* ATTC 29351. Arab J. Biotech., Vol. 6, No. (1) Jan. (2003): 13-28.). The SMDH activity can also be measured by, for example, incubating the enzyme with the substrate, such as (S)-mandelate, in the presence of phenazine methosulfate (PMS) and dichloroindophenol (DCIP), and measuring the enzyme- and substrate-dependent reduction of DCIP (Al-Baharna, ibid.). The SMDH activity can also be measured by, for example, incubating the enzyme with the substrate, such as (S)-mandelate, in sodium phosphate-citrate buffer in the presence of potassium ferricyanide, and measuring the enzyme- and substrate-dependent reduction of potassium ferricyanide (Peng Wang et al., Immobilization of (S)-mandelate dehydrogenase and its catalytic performance on stereoselective transformation of mandelic acid. Journal of the Taiwan Institute of Chemical Engineers Volume 45, Issue 3, May 2014, Pages 744-748.).

The term "benzoylformate decarboxylase (BFDC)" can refer to a protein that has the activity of catalyzing the reaction of decarboxylating benzoylformate to generate benzaldehyde (EC 4.1.1.7). This activity can also be referred to as "BFDC activity". A gene encoding BFDC can also be referred to as "BFDC gene". Examples of BFDC can include MdlC proteins encoded by mdlC genes of *Pseudomonas* bacteria such as *Pseudomonas putida*, and BFDCs of other various organisms. The nucleotide sequence of the mdlC gene (BFDC gene) of *Pseudomonas putida* is shown as SEQ ID NO: 29, and the amino acid sequence of MdlC protein (BFDC) encoded by this gene is shown as SEQ ID NO: 30. The microorganism as described herein may have one kind of BFDC, or two or more kinds of BFDCs.

The BFDC activity can be measured by, for example, incubating the enzyme with the substrate, such as benzoylformate, and measuring the enzyme- and substrate-dependent generation of the product, i.e. benzaldehyde (Park, J. K. and Jung, J. Y, Production of benzaldehyde by encapsulated whole-cell benzoylformate decarboxylase, Enzyme Microb Technol, 30, 726-733, 2002.).

That is, the benzaldehyde generation enzyme genes each may be, for example, a gene having any of the nucleotide sequences exemplified above. Also, the benzaldehyde generation enzymes each may be, for example, a protein having any of the amino acid sequences exemplified above. The expression "a gene or protein has a nucleotide or amino acid sequence" can mean that a gene or protein includes the nucleotide or amino acid sequence as well as other sequences, and can mean a gene or protein has only the nucleotide or amino acid sequence.

The benzaldehyde generation enzyme genes each may be a variant of any of the benzaldehyde generation enzyme genes exemplified above, so long as the original function thereof is maintained. Similarly, the benzaldehyde generation enzymes each may be a variant of any of the benzaldehyde generation enzymes exemplified above, so long as the original function thereof is maintained. A variant that maintains the original function thereof can also be referred to as "conservative variant". Examples of the conservative variants can include, for example, homologues and artificially modified versions of the benzaldehyde generation enzyme genes and benzaldehyde generation enzymes exemplified above.

The expression "the original function is maintained" can mean that a variant of a gene or protein has a function (such as activity or property) corresponding to the function (such as activity or property) of the original gene or protein. The expression "the original function is maintained" in relation to a gene can mean that a variant of the gene encodes a protein that maintains the original function. That is, the expression "the original function is maintained" used for the AAD gene, HMAS gene, SMDH gene, and BFDC gene can mean that the variant of the genes encodes a protein having AAD activity, HMAS activity, SMDH activity, and BFDC activity, respectively. The expression "the original function is maintained" used for AAD, HMAS, SMDH, and BFDC can mean that the variant of the proteins has AAD activity, HMAS activity, SMDH activity, and BFDC activity, respectively.

Hereinafter, examples of the conservative variants will be explained.

Homologues of the benzaldehyde generation enzyme genes or homologues of benzaldehyde generation enzymes can be easily obtained from public databases by, for example, BLAST search or FASTA search using any of the nucleotide sequences of the benzaldehyde generation enzyme genes exemplified above or any of the amino acid sequences of benzaldehyde generation enzymes exemplified above as a query sequence. Furthermore, homologues of the benzaldehyde generation enzyme genes can be obtained by, for example, PCR using a chromosome of an organism such as bacteria and yeast as the template, and oligonucleotides prepared on the basis of any of the nucleotide sequences of the benzaldehyde generation enzyme genes exemplified above as primers.

The benzaldehyde generation enzyme genes each may be a gene encoding a protein having any of the aforementioned amino acid sequences (e.g. the amino acid sequence shown as SEQ ID NO: 12 for AAD; the amino acid sequence shown as SEQ ID NO: 14, 16, 18, 20, 22, 33, 35, 37, 39, 41, 43, or 45 for HMAS; the amino acid sequence shown as SEQ ID NO: 28 for SMDH; and the amino acid sequence shown as SEQ ID NO: 30 for BFDC) including substitution, deletion, insertion, and/or addition of one or several amino acid residues at one or several positions, so long as the original function is maintained. For example, the encoded protein may have an extended or deleted N-terminus and/or C-terminus. Although the number meant by the term "one or several" used above may differ depending on the positions of amino acid residues in the three-dimensional structure of the protein or the types of amino acid residues, specifically, it is, for example, 1 to 50, 1 to 40, or 1 to 30, 1 to 20, 1 to 10, 1 to 5, or 1 to 3.

The aforementioned substitution, deletion, insertion, and/or addition of one or several amino acid residues each are a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions can include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gin, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, addition, or the like of amino acid residues as mentioned above can includes a naturally occurring mutation due to an individual difference, or a difference of species of the organism from which the gene is derived (mutant or variant).

Furthermore, the benzaldehyde generation enzyme genes each may be a gene encoding a protein having an amino acid sequence showing a homology of, for example, 50% or more, 65% or more, or 80% or more, 90% or more, 95% or more, 97% or more, or 99% or more, to the total amino acid sequence of any of the aforementioned amino acid sequences, so long as the original function is maintained. In addition, in this specification, "homology" means "identity". Specifically, the identity may be 95% or more for the case of SEQ ID NO: 22.

Furthermore, the benzaldehyde generation enzyme genes each may be a gene, such as a DNA, that is able to hybridize under stringent conditions with a probe that can be prepared from any of the aforementioned nucleotide sequences (e.g. the nucleotide sequence shown as SEQ ID NO: 11 for AAD gene; the nucleotide sequence shown as SEQ ID NO: 13, 15, 17, 19, 21, 32, 34, 36, 38, 40, 42, or 44 for HMAS gene; the nucleotide sequence shown as SEQ ID NO: 27 for SMDH gene; and the nucleotide sequence shown as SEQ ID NO: 29 for BFDC gene), such as a sequence complementary to the whole sequence or a partial sequence of any of the aforementioned nucleotide sequences, so long as the original function is maintained. The "stringent conditions" can refer to conditions under which a so-called specific hybrid is formed, and a non-specific hybrid is not formed. Examples of the stringent conditions can include those under which highly homologous DNAs hybridize to each other, for example, DNAs not less than 50%, 65%, or 80% homologous, not less than 90% homologous, not less than 95% homologous, not less than 97% homologous, or not less than 99% homologous, hybridize to each other, and DNAs less homologous than the above do not hybridize to each other, or conditions of washing of typical Southern hybridization, i.e., conditions of washing once, or 2 or 3 times, at a salt concentration and temperature corresponding to 1×SSC, 0.1% SDS at 60° C.; 0.1×SSC, 0.1% SDS at 60° C.; or 0.1×SSC, 0.1% SDS at 68° C.

The probe used for the aforementioned hybridization may be a part of a sequence that is complementary to the gene as described above. Such a probe can be prepared by PCR using oligonucleotides prepared on the basis of a known gene sequence as primers and a DNA fragment containing any of the aforementioned genes as a template. As the probe, for example, a DNA fragment having a length of about 300 bp can be used. When a DNA fragment having a length of about 300 bp is used as the probe, in particular, the washing conditions of the hybridization may be, for example, 50° C., 2×SSC and 0.1% SDS.

Furthermore, since properties concerning degeneracy of codons changes depending on the host, the benzaldehyde generation enzyme genes each may can include substitution of respective equivalent codons for arbitrary codons. That is, the benzaldehyde generation enzyme genes each may be a variant of any of the benzaldehyde generation enzyme genes exemplified above due to the degeneracy of the genetic code. For example, the benzaldehyde generation enzyme genes each may be a gene modified so that it has optimal codons according to codon frequencies in a chosen host.

The percentage of the sequence identity between two sequences can be determined by, for example, using a mathematical algorithm. Non-limiting examples of such a mathematical algorithm can include the algorithm of Myers and Miller (1988) CABIOS 4:11-17, the local homology algorithm of Smith et al (1981) Adv. Appl. Math. 2:482, the homology alignment algorithm of Needleman and Wunsch (1970) J. Mol. Biol. 48:443-453, the method for searching homology of Pearson and Lipman (1988) Proc. Natl. Acad. Sci. 85:2444-2448, and a modified version of the algorithm of Karlin and Altschul (1990) Proc. Natl. Acad. Sci. USA 87:2264, such as that described in Karlin and Altschul (1993) Proc. Natl. Acad. Sci. USA 90:5873-5877.

By using a program based on such a mathematical algorithm, sequence comparison (i.e. alignment) for determining the sequence identity can be performed. The program can be appropriately executed by a computer. Examples of such a program can include, but not limited to, CLUSTAL of PC/Gene program (available from Intelligenetics, Mountain View, Calif.), ALIGN program (Version 2.0), and GAP, BESTFIT, BLAST, FASTA, and TFASTA of Wisconsin Genetics Software Package, Version 8 (available from Genetics Computer Group (GCG), 575 Science Drive, Madison, Wis., USA). Alignment using these programs can be performed by using, for example, initial parameters. The CLUSTAL program is well described in Higgins et al. (1988) Gene 73:237-244 (1988), Higgins et al. (1989) CABIOS 5:151-153, Corpet et al. (1988) Nucleic Acids Res. 16:10881-90, Huang et al. (1992) CABIOS 8:155-65, and Pearson et al. (1994) Meth. Mol. Biol. 24:307-331.

In order to obtain a nucleotide sequence homologous to a target nucleotide sequence, in particular, for example, BLAST nucleotide search can be performed by using BLASTN program with score of 100 and word length of 12. In order to obtain an amino acid sequence homologous to a target protein, in particular, for example, BLAST protein search can be performed by using BLASTX program with score of 50 and word length of 3. See ncbi.nlm.nih.gov for BLAST nucleotide search and BLAST protein search. In addition, Gapped BLAST (BLAST 2.0) can be used in order to obtain an alignment including gap(s) for the purpose of comparison. In addition, PSI-BLAST can be used in order to perform repetitive search for detecting distant relationships between sequences. See Altschul et al. (1997) Nucleic Acids Res. 25:3389 for Gapped BLAST and PSI-BLAST. When using BLAST, Gapped BLAST, or PSI-BLAST, initial parameters of each program (e.g. BLASTN for nucleotide sequences, and BLASTX for amino acid sequences) can be used. Alignment can also be manually performed.

The sequence identity between two sequences is calculated as the ratio of residues matching in the two sequences when aligning the two sequences so as to fit maximally with each other.

Examples of HMAS further can include HMASs having a "specific mutation". Also, examples of the HMAS gene further can include HMAS genes encoding HMASs having the "specific mutation". HMAS having the "specific mutation" can also be referred to as "mutant HMAS". A gene encoding a mutant HMAS can also be referred to as "mutant HMAS gene".

HMAS not having the "specific mutation" can also be referred to as "wild-type HMAS". A gene encoding a wild-type HMAS can also be referred to as "wild-type HMAS gene". The term "wild-type" is used for convenience to distinguish the "wild-type" HMAS from the "mutant" HMAS, and the "wild-type" HMAS is not limited to those obtained as natural substances, and can include any HMAS not having the "specific mutation". Examples of the wild-type HMAS can include, for example, HMASs exemplified above. In addition, all conservative variants of HMASs exemplified above should be included in wild-type HMASs, provided that such conservative variants do not have the "specific mutation".

A mutant HMAS may be identical to a wild-type HMAS, such as HMASs exemplified above and conservative variants thereof, provided that the mutant HMAS has the "specific mutation". That is, a mutant HMAS may be a protein having any of the amino acid sequences of wild-type HMASs, but having the "specific mutation". Specifically, a mutant HMAS may be, for example, a protein having the amino acid sequence shown as SEQ ID NO: 22, provided that the mutant HMAS has the "specific mutation". Also, specifically, a mutant HMAS may be, for example, a protein having the amino acid sequence shown as SEQ ID NO: 22, but including substitution, deletion, insertion, and/or addition of one or several amino acid residues, provided that the mutant HMAS has the "specific mutation". Also, specifically, a mutant HMAS may be, for example, a protein having an amino acid sequence showing an identity of 50% or more, 65% or more, or 80% or more, 90% or more, 95% or more, 97% or more, or 99% or more to the amino acid sequence of SEQ ID NO: 22, provided that the mutant HMAS has the "specific mutation".

In a conservative variant to be used as a wild-type HMAS, conservative mutation(s) may occur at position(s) other than the position(s) of the "specific mutation". That is, in other words, a mutant HMAS may be a protein having any of the amino acid sequences of HMASs exemplified above, but having the "specific mutation" and further including conservative mutation(s), such as substitution, deletion, insertion, and/or addition of one or several amino acid residues, at position(s) other than the position(s) of the "specific mutation".

The "specific mutation" may be a mutation effective for production of benzaldehyde, such as a mutation resulting in an increased production of benzaldehyde in the method as described herein. Such an increased production of benzaldehyde may be due to, for example, an increased generation of (S)-mandelate by HMAS. Hence, the "specific mutation" may also be a mutation resulting in an increased generation of (S)-mandelate by HMAS.

Examples of the "specific mutation" can include mutations at amino acid residues corresponding to T2, M3, G5, Y18, A27, D35, E46, E180, A187, E191, V194, A199, D201, Q206, I217, D220, T222, G255, F319, G327, I336, K337, V343, and Q347. The "specific mutation" may be a mutation at one amino acid residue, or may be a combination of mutations at two or more amino acid residues. That is, the "specific mutation" may be, for example, one or more mutation(s) at amino acid residue(s) corresponding to one or more of the following amino acid residues: T2, M3, G5, Y18, A27, D35, E46, E180, A187, E191, V194, A199, D201, Q206, I217, D220, T222, G255, F319, G327, I336, K337, V343, and/or Q347.

In the aforementioned notation used for defining amino acid residues, the numbers represent the positions in the amino acid sequence shown as SEQ ID NO: 22, and the letters at the left side of the numbers represent the amino acid residues at the respective positions in the amino acid sequence shown as SEQ ID NO: 22 (i.e. the amino acid residues before modification at the respective positions). That is, for example, "T2" represents T (Thr) residue at position 2 in the amino acid sequence shown as SEQ ID NO: 22.

In each of the aforementioned mutations, the amino acid residue after modification may be any amino acid residue other than the amino acid residue before modification. Examples of the amino acid residue after modification can include K (Lys), R (Arg), H (His), A (Ala), V (Val), L (Leu), I (Ile), G (Gly), S (Ser), T (Thr), P (Pro), F (Phe), W (Trp), Y (Tyr), C (Cys), M (Met), D (Asp), E (Glu), N (Asn), and Q (Gln), provided that the amino acid residues after modification is other than the amino acid residue before modification. As the amino acid residues after modification, there may be selected those effective for production of benzaldehyde.

Specific examples of the "specific mutation" can include mutations corresponding to T2N, M3I, G5R, Y18F, A27V, D35G, E46Q, E180K, A187V, E191K, V194G, A199(S, V), D201N, Q206R, I217(L, V), D220(A, N), T222S, G255D, F319Y, G327(D, S), I336V, K337Q, V343M, and Q347L. That is, the mutations at amino acid residues corresponding to T2, M3, G5, Y18, A27, D35, E46, E180, A187, E191, V194, A199, D201, Q206, I217, D220, T222, G255, F319, G327, I336, K337, V343, and Q347 may be, for example, the mutations corresponding to T2N, M3I, G5R, Y18F, A27V, D35G, E46Q, E180K, A187V, E191K, V194G, A199 (S, V), D201N, Q206R, I217(L, V), D220(A, N), T222S, G255D, F319Y, G327(D, S), I336V, K337Q, V343M, and Q347L, respectively. The "specific mutation" may be, for example, one or more of the following mutation(s): T2N, M3I, G5R, Y18F, A27V, D35G, E46Q, E180K, A187V, E191K, V194G, A199(S, V), D201N, Q206R, I217(L, V), D220(A, N), T222S, G255D, F319Y, G327(D, S), I336V, K337Q, V343M, and/or Q347L.

In the aforementioned notation used for defining mutations, the numbers and the letters at the left side of the numbers represent the same as described above. In the aforementioned notation used for defining mutations, the letters at the right side of the numbers represent the amino acid residues after modification at the respective positions. That is, for example, "T2N" represents a mutation for replacing T (Thr) residue at position 2 in the amino acid sequence shown as SEQ ID NO: 22 with N (Asn) residue. Also, for example, A199(S, V) represents a mutation for replacing A (Ala) residue at position 199 in the amino acid sequence shown as SEQ ID NO: 22 with S (Ser) or V (Val) residue.

Combination of mutations is not particularly limited. Specific examples of combination of mutations can include M3I/A199S/G255D, Y18F/D220N, A27V/E191K, D35G/E46Q/T222S/I336V, E180K/I217V/D220N, A187V/I217V, A199V/I217V/K337Q, D201N/I217V, I217V/F319Y, and D220A/Q347L. That is, the "specific mutation" may be, for example, mutations corresponding to any of these combinations.

In the aforementioned notation used for defining combinations, the numbers and the letters at the left and right sides of the numbers represent the same as described above. In the aforementioned notation used for defining combinations, two or more mutations noted together and inserted with "/" represent a double or more multiple mutation. That is, for example, "M3I/A199S/G255D" represents a triple mutation of M3I, A199S, and G255D.

A "mutation corresponding to a mutation at the amino acid residue at position X in the amino acid sequence shown in SEQ ID NO: 22" should be read as a mutation at an amino acid residue corresponding to the amino acid residue at position X in the amino acid sequence shown in SEQ ID NO: 22". That is, for example, a "mutation corresponding to T2N" represents a mutation for replacing an amino acid residue corresponding to T2 with N (Asn) residue.

The "position X" in an amino acid sequence can refer to the X-th position counted from the N-terminus of the amino acid sequence, and the amino acid residue of the N-terminus is the amino acid residue at position 1. The positions defined in the aforementioned mutations represent the relative positions, and the absolute positions thereof may shift due to deletion, insertion, addition, and so forth of amino acid residue(s). For example, if one amino acid residue is deleted or inserted at a position on the N-terminus side of position X in the amino acid sequence shown as SEQ ID NO: 22, the amino acid residue originally at position X is relocated at position X−1 or X+1, however, it is still regarded as the "amino acid residue corresponding to the amino acid residue at position X of the amino acid sequence shown as SEQ ID NO: 22".

The amino acid residues before modifications defined in the above-exemplified mutations are typical ones, but may not necessarily be limited thereto. For example, the "amino acid residue corresponding to T2" may typically be T (Thr) residue, however, it may not necessarily be T (Thr) residue. That is, when a wild-type HMAS has an amino acid sequence other than that shown in SEQ ID NO: 22, the "amino acid residue corresponding to T2" may be an amino acid residue other than T (Thr) residue. Therefore, the "mutation corresponding to T2N" can include not only a mutation, when the "amino acid residue corresponding to T2" is T (Thr) residue, for replacing this T (Thr) residue with N (Asn) residue, but also can include a mutation, when the "amino acid residue corresponding to T2" is K (Lys), R (Arg), H (His), A (Ala), V (Val), L (Leu), I (Ile), G (Gly), S (Ser), P (Pro), F (Phe), W (Trp), C (Cys), M (Met), D (Asp), E (Glu), or Q (Gln) residue, for replacing this residue with N (Asn) residue. The same can be applied mutatis mutandis to the other mutations.

In the amino acid sequence of an arbitrary HMAS, which amino acid residue is an "amino acid residue corresponding to the amino acid residue at position X in the amino acid sequence shown in SEQ ID NO: 22" can be determined by aligning the amino acid sequence of the arbitrary HMAS and the amino acid sequence of SEQ ID NO: 22. The alignment can be performed by, for example, using known gene analysis software. Specific examples of such software can include DNASIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

The microorganism as described herein or each part thereof, i.e. a single microorganism or each of a plurality of microorganisms constituting the microorganism as described herein, may be a microorganism inherently having the benzaldehyde generation enzyme gene(s), or may be a microorganism modified so that it has the benzaldehyde generation enzyme gene(s). Examples of the microorganism inherently having the benzaldehyde generation enzyme gene(s) can include such microorganisms as mentioned above from which the benzaldehyde generation enzymes are derived. Examples of the microorganism modified so that it has the benzaldehyde generation enzyme gene(s) can include a microorganism into which the benzaldehyde generation enzyme gene(s) has/have been introduced. Furthermore, the microorganism as described herein or each part thereof, i.e. a single microorganism or each of a plurality of microorganisms constituting the microorganism as described herein, may have been introduced with appropriate benzaldehyde generation enzyme gene(s), instead of, or in addition to, the benzaldehyde generation enzyme gene(s) inherently possessed by the microorganism as described herein or each part thereof. A microorganism into which the benzaldehyde generation enzyme gene(s) will be introduced and a microorganism into which the benzaldehyde generation enzyme gene(s) has/have been introduced can also be collectively referred to as "host".

A benzaldehyde generation enzyme gene can be obtained by, for example, cloning from an organism having the benzaldehyde generation enzyme gene. For cloning, nucleotides containing the gene, such as genomic DNA and cDNA, can be used. Alternatively, a benzaldehyde generation enzyme gene can be obtained by, for example, chemical synthesis (Gene, 60(1), 115-127 (1987)).

The obtained benzaldehyde generation enzyme gene may be used as it is, or may be modified before use. That is, for example, the obtained benzaldehyde generation enzyme gene can be modified, to thereby obtain a variant thereof. Genes can be modified by using a known method. For example, an objective mutation can be introduced into a target site of DNA by the site-specific mutagenesis method. That is, for example, the coding region of a gene can be modified by the site-specific mutation method so that a specific site of the encoded protein can include substitution, deletion, insertion, and/or addition of amino acid residue(s). Examples of the site-specific mutagenesis method can include a method of using PCR (Higuchi, R., 61, in PCR Technology, Erlich, H. A. Eds., Stockton Press, 1989; Carter P, Meth., in Enzymol., 154, 382, 1987), and a method of using a phage (Kramer, W. and Frits, H. J., Meth., in Enzymol., 154, 350, 1987; Kunkel, T. A. et al., Meth. in Enzymol., 154, 367, 1987).

In addition, a mutant HMAS gene can be obtained by, for example, modifying a wild-type HMAS gene so that HMAS encoded thereby has the "specific mutation". Such modification can be performed by using a known method such as the site-specific mutagenesis method. Alternatively, a mutant HMAS gene can also be obtained without using a wild-type HMAS gene. For example, a mutant HMAS gene may be directly obtained by chemical synthesis. The obtained mutant HMAS gene may be used as it is, or may be further modified before use.

The method for introducing the benzaldehyde generation enzyme gene into a host is not particularly limited. It is sufficient that the benzaldehyde generation enzyme gene is expressibly harbored by a host. The benzaldehyde generation enzyme gene can be introduced into a microorganism by the same way as that for introduction of a gene described below in the "Methods for increasing activity of protein".

In addition, when a microorganism already has an HMAS gene on the chromosome thereof or the like, the microorganism can also be modified to have a mutant HMAS gene by introducing the "specific mutation" into the HMAS gene on the chromosome or the like. A mutation can be introduced into a gene on a chromosome or the like by, for example, natural mutation, mutagenesis treatment, or genetic engineering.

Furthermore, the microorganism as described herein may be a microorganism inherently having L-phenylalanine-producing ability, or may be a microorganism modified so that it has L-phenylalanine-producing ability. The microorganism having L-phenylalanine-producing ability can be obtained by imparting L-phenylalanine-producing ability to such a microorganism as mentioned above, or enhancing L-phenylalanine-producing ability of such a microorganism as mentioned above.

Hereafter, specific examples of the method for imparting or enhancing L-phenylalanine-producing ability will be explained. Such modifications as exemplified below for imparting or enhancing L-phenylalanine-producing ability may be independently used, or may be used in an appropriate combination.

Examples of the method for imparting or enhancing L-phenylalanine-producing ability can include a method of increasing the activity of an L-phenylalanine biosynthesis enzyme. That is, the microorganism as described herein may have been modified so that the activity of an L-phenylalanine biosynthesis enzyme is increased. The activity of one kind of L-phenylalanine biosynthesis enzyme may be increased, or the activities of two or more kinds of L-phenylalanine biosynthesis enzymes may be increased. The method for increasing the activity of a protein (enzyme etc.) will be described later. The activity of a protein (enzyme etc.) can be increased by, for example, increasing the expression of a gene encoding the protein.

Examples of the L-phenylalanine biosynthesis enzymes can include common biosynthesis enzymes of aromatic amino acids, such as 3-deoxy-D-arabinoheptulosonate-7-phosphate synthase (aroF, aroG, aroH), 3-dehydroquinate synthase (aroB), 3-dehydroquinate dehydratase (aroD), shikimate dehydrogenase (aroE), shikimate kinase (aroK, aroL), 5-enolpyruvylshikimate-3-phosphate synthase (aroA), and chorismate synthase (aroC); as well as chorismate mutase (pheA), prephenate dehydratase (pheA), and tyrosine amino transferase (tyrB). Shown in the parentheses after the names of the enzymes are examples of the names of the genes encoding the enzymes (the same shall apply to the same occasions hereafter). Chorismate mutase and prephenate dehydratase may be encoded by pheA gene as a bifunctional enzyme. The expression of genes encoding some L-phenylalanine biosynthesis enzymes, such as DAHP synthase, 3-dehydroquinate synthase, and 3-dehydroquinate dehydratase, can be repressed by a tyrosine repressor TyrR, which is encoded by tyrR gene. Therefore, the activity of an L-phenylalanine biosynthesis enzyme can be increased by, for example, reducing the activity of the tyrosine repressor TyrR. In addition, some L-phenylalanine biosynthesis enzymes can be subject to feedback inhibition by aromatic amino acid(s) such as L-phenylalanine. For example, the bifunctional chorismate mutase-prephenate dehydratase can be subject to feedback inhibition by L-phenylalanine. Therefore, the activity of an L-phenylalanine biosynthesis enzyme can be increased by, for example, using a gene encoding a mutant L-phenylalanine biosynthesis enzyme desensitized to such feedback inhibition.

Examples of the method for imparting or enhancing L-phenylalanine-producing ability further can include a method of reducing the activity of an enzyme that is involved in the by-production of a substance other than L-phenylalanine. Such a substance other than L-phenylalanine can also be referred to as "byproduct". Examples of the byproduct can include other aromatic amino acids such as L-tyrosine and L-tryptophan. Examples of the enzyme that is involved in the by-production of L-tyrosine can include a bifunctional enzyme chorismate mutase-prephenate dehydrogenase (tyrA).

Specific examples of L-phenylalanine-producing bacteria and parent strains for deriving them can include, for example, *E. coli* AJ12739 (tyrA::Tn10, tyrR) (VKPM B-8197), which is deficient in the chorismate mutase-prephenate dehydrogenase and the tyrosine repressor (WO003/044191), *E. coli* AJ12741, which is deficient in the chorismate mutase-prephenate dehydrogenase and the tyrosine repressor, and contains a mutant aroG gene encoding 3-deoxy-D-arabinoheptulosonate-7-phosphate synthase desensitized to feedback inhibition, a mutant pheA gene encoding chorismate mutase-prephenate dehydratase desensitized to feedback inhibition, and an aroL gene encoding shikimate kinase (JP H05-344881 A), *E. coli* HW1089 (ATCC 55371), which contains pheA34 gene encoding a chorismate mutase-prephenate dehydratase desensitized to feedback inhibition (U.S. Pat. No. 5,354,672), *E. coli* MWEC101-b (KR8903681), *E. coli* NRRL B-12141, NRRL B-12145, NRRL B-12146, and NRRL B-12147 (U.S. Pat. No. 4,407,952). Specific examples of L-phenylalanine-producing bacteria and parent strains for deriving them also can include, for example, *E. coli* K-12<W3110(tyrA)/pPHAB>(FERM BP-3566), *E. coli* K-12<W3110(tyrA)/pPHAD>(FERM BP-12659), *E. coli* K-12<W3110(tyrA)/pPHATerm> (FERM BP-12662), and *E. coli* K-12 AJ12604<W3110 (tyrA)/pBR-aroG4, pACMAB>(FERM BP-3579), which contains a gene encoding a chorismate mutase-prephenate dehydratase desensitized to feedback inhibition (EP 488424 B1). Specific examples of L-phenylalanine-producing bacteria and parent strains for deriving them further can include, for example, strains belonging to the genus *Escherichia* having an increased activity of the protein encoded by the yedA gene or the yddG gene (U.S. Patent Published Applications Nos. 2003/0148473 and 2003/0157667, WO03/044192). Specific examples of L-phenylalanine-producing bacteria and parent strains for deriving them also can include, for example, *Corynebacterium glutamicum* strains BPS-13 (FERM BP-1777), K77 (FERM BP-2062), and K78 (FERM BP-2063) (EP 331145 A, JP H02-303495 A), of which phosphoenolpyruvate carboxylase or pyruvate kinase activity is reduced, and tyrosine-auxotrophic strains of coryneform bacteria (JP H05-049489 A).

The genes and proteins used for breeding a microorganism having L-phenylalanine-producing ability may have, for example, known nucleotide sequences and amino acid sequences, respectively. Also, the genes and proteins used for breeding a microorganism having L-phenylalanine-producing ability may be conservative variants of genes and proteins having known nucleotide sequences and amino acid sequences, respectively. Specifically, for example, the genes used for breeding a microorganism having L-phenylalanine-producing ability may each be a gene encoding a protein having a known amino acid sequence of a protein, but including substitution, deletion, insertion, and/or addition of one or several some amino acid residues at one or several positions, so long as the original function thereof, i.e. enzymatic activity etc., is maintained. As for conservative variants of genes and proteins, the descriptions concerning conservative variants of the benzaldehyde generation enzyme genes and benzaldehyde generation enzymes described above can be applied mutatis mutandis.

The microorganism as described herein may further have other arbitrary modification(s), so long as production of benzaldehyde is attained.

The order of modifications for constructing the microorganism as described herein is not particularly limited.

<1-2> Methods for Increasing Activity of Protein

Hereafter, the methods for increasing the activity of a protein, including methods for introduction of a gene, will be explained.

The expression "the activity of a protein is increased" can mean that the activity of the protein is increased as compared with a non-modified strain. Specifically, the expression "the activity of a protein is increased" may mean that the activity of the protein per cell is increased as compared with that of a non-modified strain. The term "non-modified strain" used herein can refer to a control strain that has not been modified so that the activity of an objective protein is increased. Examples of the non-modified strain can include a wild-type strain and parent strain. Specific examples of the non-modified strain can include the respective type strains of the species of microorganisms. Specific examples of the non-modified strain also can include strains exemplified above in relation to the description of microorganisms. That is, in an embodiment, the activity of a protein may be increased as compared with a type strain, i.e. the type strain of the species to which a microorganism belongs. In another embodiment, the activity of a protein may also be increased as compared with the *C. glutamicum* ATCC 13869 strain. In another embodiment, the activity of a protein may also be increased as compared with the *C. glutamicum* ATCC 13032 strain. In another embodiment, the activity of a protein may also be increased as compared with the *E. coli* K-12 MG1655 strain. The state that "the activity of a protein is increased" may also be expressed as "the activity of a protein is enhanced". More specifically, the expression "the activity of a protein is increased" may mean that the number of molecules of the protein per cell is increased, and/or the function of each molecule of the protein is increased as compared with those of a non-modified strain. That is, the term "activity" in the expression "the activity of a protein is increased" is not limited to the catalytic activity of the protein, but may also mean the transcription amount of a gene (i.e. the amount of mRNA) encoding the protein, or the translation amount of the protein (i.e. the amount of the protein). Furthermore, the state that "the activity of a protein is increased" can include not only a state that the activity of an objective protein is increased in a strain inherently having the activity of the objective protein, but also a state that the activity of an objective protein is imparted to a strain not inherently having the activity of the objective protein. Furthermore, so long as the activity of the protein is eventually increased, the activity of an objective protein inherently contained in a host may be attenuated and/or eliminated, and then an appropriate type of the objective protein may be imparted to the host.

The degree of the increase in the activity of a protein is not particularly limited, so long as the activity of the protein is increased as compared with a non-modified strain. The activity of the protein may be increased to, for example, 1.2 times or more, 1.5 times or more, 2 times or more, or 3 times or more of that of a non-modified strain. Furthermore, when the non-modified strain does not have the activity of the objective protein, it is sufficient that the protein is produced as a result of introduction of the gene encoding the protein, and for example, the protein may be produced to such an extent that the activity thereof can be measured.

The modification for increasing the activity of a protein can be attained by, for example, increasing the expression of a gene encoding the protein. The expression "the expression of a gene is increased" can mean that the expression of the gene is increased as compared with a non-modified strain such as a wild-type strain and parent strain. Specifically, the expression "the expression of a gene is increased" may mean that the expression amount of the gene per cell is increased as compared with that of a non-modified strain. More specifically, the expression "the expression of a gene is increased" may mean that the transcription amount of the gene (i.e. the amount of mRNA) is increased, and/or the translation amount of the gene (i.e. the amount of the protein expressed from the gene) is increased. The state that "the expression of a gene is increased" can also be referred to as "the expression of a gene is enhanced". The expression of a gene may be increased to, for example, 1.2 times or more, 1.5 times or more, 2 times or more, or 3 times or more of that of a non-modified strain. Furthermore, the state that "the expression of a gene is increased" can include not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" may also mean, for example, that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination can include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome can include repetitive DNAs, and inverted repeats located at the both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Furthermore, the vector can have a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in Enterobacteriaceae bacteria such as *Escherichia coli* can include, for example, pUC19, pUC18, pHSG299, pHSG399, pHSG398, pBR322, pSTV29 (all of these are available from Takara Bio), pACYC 184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (TaKaRa Bio), pACYC series vectors, and the broad host spectrum vector RSF 1010. Specific examples of vector autonomously replicable in coryneform bacteria can include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 described in Japanese Patent Laid-open (Kokai) No. 3-210184; plasmids pCRY21, pCRY2KE, pCRY2KX, pCRY31, pCRY3KE, and pCRY3KX described in Japanese Patent Laid-open (Kokai) No. 2-72876 and U.S. Pat. No. 5,185,262; plasmids pCRY2 and pCRY3 described in Japanese Patent Laid-open (Kokai) No. 1-191686; pAJ655, pAJ611, and pAJ1844 described in Japanese Patent Laid-open (Kokai) No. 58-192900; pCG1 described in Japanese Patent Laid-open (Kokai) No. 57-134500; pCG2 described in Japanese Patent Laid-open (Kokai) No. 58-35197; pCG4 and pCG11 described in Japanese Patent Laid-open (Kokai) No. 57-183799; pVK7 described in Japanese Patent Laid-open (Kokai) No. 10-215883; pVK9 described in WO2007/046389; pVS7 described in WO2013/069634; and pVC7 described in Japanese Patent Laid-open (Kokai) No. 9-070291.

When a gene is introduced, it is sufficient that the gene is expressibly harbored by a host. Specifically, it is sufficient that the gene is harbored by a host so that it is expressed under control of a promoter that functions in the host. The term "a promoter that functions in a host" can refer to a promoter that shows a promoter activity in the host. The promoter may be a promoter native to the host, or a heterogenous promoter. The promoter may be the native promoter of the gene to be introduced, or a promoter of another gene. As the promoter, for example, such a stronger promoter as mentioned later may also be used.

A terminator for termination of gene transcription may be located downstream of the gene. The terminator is not particularly limited so long as it functions in a host. The terminator may be a terminator native to the host, or a heterogenous terminator. The terminator may be the native terminator of the gene to be introduced, or a terminator of another gene. Specific examples of the terminator can include, for example, T7 terminator, T4 terminator, fd phage terminator, tet terminator, and trpA terminator.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more of genes are introduced, it is sufficient that the genes each are expressibly harbored by a host. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced. The case of "introducing two or more genes" can include, for example, cases of introducing respective genes encoding two or more kinds of proteins (such as enzymes), introducing respective genes encoding two or more subunits constituting a single protein complex (such as enzyme complex), and a combination of the foregoing cases.

The gene to be introduced is not particularly limited so long as it encodes a protein that functions in the host. The gene to be introduced may be a gene native to the host, or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as a template. The gene to be introduced may also be totally synthesized, for example, on the basis of the nucleotide sequence of the gene (Gene, 60(1), 115-127 (1987)). The obtained gene can be used as it is, or after being modified as required. That is, a variant of a gene may be obtained by modifying the gene. A gene can be modified by a known technique. For example, an objective mutation can be introduced into an objective site of DNA by the site-specific mutation method. That is, the coding region of a gene can be modified by the site-specific mutation method so that a specific site of the encoded protein can include substitution, deletion, insertion, or addition of amino acid residues. Examples of the site-specific mutation method can include the method utilizing PCR (Higuchi, R., 61, in PCR Technology, Erlich, H. A. Eds., Stockton Press (1989); Carter, P, Meth. in Enzymol., 154, 382 (1987)), and the method utilizing phage (Kramer, W. and Frits, H. J., Meth. in Enzymol., 154, 350 (1987); Kunkel, T. A. et al., Meth. in Enzymol., 154, 367 (1987)). Alternatively, a variant of a gene may be totally synthesized.

In addition, when a protein functions as a complex consisting of a plurality of subunits, a part or all of the plurality of subunits may be modified, so long as the activity of the protein is eventually increased. That is, for example, when the activity of a protein is increased by increasing the expression of a gene, the expression of a part or all of the plurality of genes that encode the subunits may be enhanced. It is usually preferable to enhance the expression of all of the plurality of genes encoding the subunits. Furthermore, the subunits constituting the complex may be derived from a single kind of organism or two or more kinds of organisms, so long as the complex has a function of the objective protein. That is, for example, genes of the same organism encoding a plurality of subunits may be introduced into a host, or genes of different organisms encoding a plurality of subunits may be introduced into a host.

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively can refer to sites that affect the expression of a gene. Examples of the expression control sequence can include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, a method of using a temperature sensitive vector, or the Red driven integration method (WO2005/010175).

The transcription efficiency of a gene can be improved by, for example, replacing the promoter of the gene on a chromosome with a stronger promoter. The term "stronger promoter" can mean a promoter providing an improved transcription of a gene compared with an inherently existing wild-type promoter of the gene. Examples of stronger promoters can include, for example, the known high expression promoters such as T7 promoter, trp promoter, lac promoter, thr promoter, tac promoter, trc promoter, tet promoter, araBAD promoter, rpoH promoter, msrA promoter, Pm1 promoter (native to the genus *Bifidobacterium*), PR promoter, and PL promoter. Examples of stronger promoters usable in coryneform bacteria can include, for example, the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, and cspB, SOD, and tuf (EF-Tu) promoters, which are potent promoters capable of providing a large expression amount in coryneform bacteria (Journal of Biotechnology, 104 (2003) 311-323; Appl. Environ. Microbiol., 2005 Dec.; 71 (12): 8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO00/18935). Examples of highly active-type promoter can include various tac-like promoters (Katashkina J I et al., Russian Federation Patent Application No. 2006134574). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" can mean a SD sequence that provides an improved translation of mRNA compared with the inherently existing wild-type SD sequence of the gene. Examples of stronger SD sequences can include, for example, RBS of the gene 10 native to phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of the gene can be improved by replacing a rare codon present in the gene with a synonymous codon more frequently used. That is, the gene to be introduced may be modified, for example, so as to contain optimal codons according to the frequencies of codons observed in a host to be used. Codons can be replaced by, for example, the site-specific mutation method for introducing an objective mutation into an objective site of DNA. Alternatively, a gene fragment in which objective codons are replaced may be totally synthesized. Frequencies of codons in various organisms are disclosed in the "Codon Usage Database" (kazusa.or.jp/codon; Nakamura, Y et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

Furthermore, the modification that increases the activity of a protein can also be attained by, for example, enhancing the specific activity of the enzyme. Enhancement of the specific activity also can include desensitization to feedback inhibition. That is, when a protein is subject to feedback inhibition by a metabolite, the activity of the protein can be increased by making a host harbor a gene encoding a mutant protein that has been desensitized to the feedback inhibition. The phrase "desensitization to feedback inhibition" can include complete elimination of the feedback inhibition, and attenuation of the feedback inhibition, unless otherwise stated. Also, a state of "being desensitized to feedback inhibition", i.e. a state that feedback inhibition is eliminated or attenuated, can also be referred to as "tolerant to feedback inhibition". A protein showing an enhanced specific activity can be obtained by, for example, searching various organisms. Furthermore, a highly-active type of an existing protein may also be obtained by introducing a mutation into the existing protein. The mutation to be introduced may be, for example, substitution, deletion, insertion, or addition of one or several amino acid residues at one or several position of the protein. The mutation can be introduced by, for example, such a site-specific mutation method as mentioned above. The mutation may also be introduced by, for example, a mutagenesis treatment. Examples of the mutagenesis treatment can include irradiation of X-ray, irradiation of ultraviolet, and a treatment with a mutation agent such as N-methyl-N'-nitro-N-nitrosoguanidine (MNNG), ethyl methanesulfonate (EMS), and methyl methanesulfonate (MMS). Furthermore, a random mutation may be induced by directly treating DNA in vitro with hydroxylamine. Enhancement of the specific activity may be independently used, or may be used in an arbitrary combination with such methods for enhancing gene expression as mentioned above.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse method reported for coryneform bacteria (Japanese Patent Laid-open (Kokai) No. 2-207791) can also be used.

An increase in the activity of a protein can be confirmed by measuring the activity of the protein.

An increase in the activity of a protein can also be confirmed by confirming an increase in the expression of a gene encoding the protein. An increase in the expression of a gene can be confirmed by confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA can include Northern hybridization, RT-PCR, and so forth (Sambrook, J., et al., Molecular Cloning A Laboratory Manual/Third Edition, Cold Spring Harbor Laboratory Press, Cold Spring Harbor (USA), 2001). The amount of mRNA may increase to, for example, 1.2 times or more, 1.5 times or more, 2 times or more, or 3 times or more of that of a non-modified strain.

An increase in the amount of a protein can be confirmed by Western blotting using antibodies (Molecular Cloning, Cold Spring Harbor Laboratory Press, Cold Spring Harbor (USA), 2001). The amount of the protein may increase to, for example, 1.2 times or more, 1.5 times or more, 2 times or more, or 3 times or more of that of a non-modified strain.

The aforementioned methods for increasing the activity of a protein can be applied to enhancement of the activities of arbitrary proteins such as L-phenylalanine biosynthesis enzymes, and enhancement of the expression of arbitrary genes such as genes encoding those arbitrary proteins, besides introduction of benzaldehyde generation enzyme genes.

<1-3> Method for Reducing Activity of Protein

Hereafter, the methods for reducing the activity of a protein will be explained.

The expression "the activity of a protein is reduced" can mean that the activity of the protein is reduced as compared with a non-modified strain. Specifically, the expression "the activity of a protein is reduced" may mean that the activity of the protein per cell is reduced as compared with that of a non-modified strain. The term "non-modified strain" can refer to a control strain that has not been modified so that the activity of an objective protein is reduced. Examples of the non-modified strain can include a wild-type strain and parent strain. Specific examples of the non-modified strain can include the respective type strains of the species of microorganisms. Specific examples of the non-modified strain also can include strains exemplified above in relation to the description of microorganisms. That is, in an embodiment, the activity of a protein may be reduced as compared with a type strain, i.e. the type strain of the species to which a microorganism belongs. In another embodiment, the activity of a protein may also be reduced as compared with the *C. glutamicum* ATCC 13869 strain. In another embodiment, the activity of a protein may also be reduced as compared with the *C. glutamicum* ATCC 13032 strain. In another embodiment, the activity of a protein may also be reduced as compared with the *E. coli* K-12 MG1655 strain. The state that "the activity of a protein is reduced" also can include a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e. the amount of mRNA) encoding the protein or the translation amount of the protein (i.e. the amount of the protein). The state that "the number of molecules of the protein per cell is reduced" also can includes a state that the protein does not exist at all. The state that "the function of each molecule of the protein is reduced" also can include a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The expression "the expression of a gene is reduced" can mean that the expression of the gene is reduced as compared with a non-modified strain such as a wild-type strain and parent strain. Specifically, the expression "the expression of a gene is reduced" may mean that the expression of the gene per cell is reduced as compared with that of a non-modified strain. More specifically, the expression "the expression of a gene is reduced" may mean that the transcription amount of the gene (i.e. the amount of mRNA) is reduced, and/or the translation amount of the gene (i.e. the amount of the protein expressed from the gene) is reduced. The state that "the expression of a gene is reduced" also can include a state that the gene is not expressed at all. The state that "the expression of a gene is reduced" can also be referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, the Shine-Dalgarno (SD) sequence (also referred to as ribosome-binding site (RBS)), and a spacer region between RBS and the start codon of the gene. When an expression control sequence is modified, one or more nucleotides, two or more nucleotides, or three or more nucleotides, of the expression control sequence can be modified. For example, the transcription efficiency of a gene can be reduced by, for example, replacing the promoter of the gene on a chromosome with a weaker promoter. The term "weaker promoter" can mean a promoter providing an attenuated transcription of a gene compared with an inherently existing wild-type promoter of the gene. Examples of weaker promoters can include, for example, inducible promoters. That is, an inducible promoter may function as a weaker promoter under a non-induced condition, such as in the absence of the corresponding inducer. Furthermore, a part or the entire expression control sequence may be deleted. The expression of a gene can also be reduced by, for example, manipulating a factor responsible for expression control. Examples of the factor responsible for expression control can include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" can mean that a gene is modified so that a protein that can normally function is not produced. The state that "a protein that normally functions is not produced" can includes a state that the protein is not produced at all from the gene, and a state that the protein of which the function (such as activity or property) per molecule is reduced or eliminated is produced from the gene.

Disruption of a gene can be attained by, for example, deleting a part or the entire coding region of the gene on a chromosome. Furthermore, the entire gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof can include, for example, a marker gene such as antibiotic resistance genes, and a gene useful for production of an objective substance.

Such modification of a gene on a chromosome as described above can be attained by, for example, preparing a deficient-type gene modified so that it is unable to produce a protein that normally functions, and transforming a host with a recombinant DNA containing the deficient-type gene to cause homologous recombination between the deficient-type gene and the wild-type gene on a chromosome and thereby substitute the deficient-type gene for the wild-type gene on the chromosome. In this procedure, if a marker gene selected according to the characteristics of the host such as auxotrophy is included in the recombinant DNA, the operation becomes easier. Examples of the deficient-type gene can include a gene including deletion of all or a part of the gene, gene including a missense mutation, gene including a nonsense mutation, gene including a frame shift mutation, and gene including insertion of a transposon or marker gene. The protein encoded by the deficient-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from X phage (Cho, E. H., Gumport, R. I., Gardner, J. F., J. Bacteriol., 184:5200-5203 (2002)) (refer to WO2005/010175), a method of using a plasmid having a temperature-sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment can include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of a plurality of subunits, a part or all of the plurality of subunits may be modified, so long as the activity of the protein is eventually reduced. That is, for example, a part or all of a plurality of genes that encode the respective subunits may be disrupted or the like. Furthermore, when there is a plurality of isozymes of a protein, a part or all of the activities of the plurality of isozymes may be reduced, so long as the activity of the protein is eventually reduced. That is, for example, a part or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that observed in a non-modified strain. Examples of the method for evaluating the amount of mRNA can include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, of that observed in a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0%, of that observed in a non-modified strain.

Disruption of a gene can be confirmed by determining nucleotide sequence of a part or the entire gene, restriction enzyme map, full length, or the like of the gene depending on the method(s) used for the disruption.

The aforementioned methods for reducing the activity of a protein can be applied to reduction in the activities of arbitrary proteins such as enzymes involved in the by-production of byproducts, and reduction in the expression of arbitrary genes such as genes encoding those arbitrary proteins.

<2> Method

The method as described herein is a method for producing benzaldehyde by using the microorganism as described herein. In other words, the method as described herein is a method for producing benzaldehyde that includes a step of producing benzaldehyde by using the microorganism as described herein. This step can also be referred to as "production step".

Benzaldehyde can be produced by, for example, fermentation, bioconversion, or a combination thereof. That is, the production step may be carried out by, for example, fermentation, bioconversion, or both. Specifically, the production step may be carried out by, for example, cultivating the microorganism as described herein, using cells of the microorganism as described herein, or both. When using both methods, a portion of the plurality of microorganisms as described herein are cultivated, and then cells of the remaining part of the plurality of microorganisms are further used to produce benzaldehyde. Benzaldehyde can be produced from, for example, a carbon source or L-phenylalanine.

<2-1> Fermentation Method

Benzaldehyde can be produced by, for example, fermentation of the microorganism as described herein having L-phenylalanine-producing ability. That is, an embodiment of the method as described herein may be a method for producing benzaldehyde by fermentation of the microorganism as described herein having L-phenylalanine-producing ability. This embodiment can also be referred to as "fermentation method". Also, the step of producing benzaldehyde by fermentation of the microorganism as described herein having L-phenylalanine-producing ability can also be referred to as "fermentation step".

The fermentation step can be performed by cultivating the microorganism as described herein. Specifically, in the fermentation method, benzaldehyde can be produced from a carbon source. That is, the fermentation step may be, for example, a step of cultivating the microorganism as described herein in a culture medium, such as a culture medium containing a carbon source, to produce and accumulate benzaldehyde in the culture medium. That is, the fermentation method may be a method for producing benzaldehyde by cultivating the microorganism as described herein in a culture medium, such as a culture medium containing a carbon source, to produce and accumulate benzaldehyde in the culture medium. Also, in other words, the fermentation step may be, for example, a step of producing benzaldehyde from a carbon source by using the microorganism as described herein.

When the microorganism as described herein is a plurality of microorganisms, the plurality of microorganisms may be or may not be cultivated simultaneously. For example, the plurality of microorganisms may be inoculated simultaneously and cultivated, or may be inoculated at different times individually or as arbitrary combinations and cultivated. The order and timings for cultivating such a plurality of microorganisms are not particularly limited, so long as production of benzaldehyde from the carbon source is attained. For example, a microorganism having AAD, a microorganism having HMAS, a microorganism having SMDH, and a microorganism having BFDC may be inoculated in this order. The phrase "cultivating the microorganism as described herein in a culture medium containing a carbon source" relative to when the microorganism as described herein is a plurality of microorganisms can mean that at least one microorganism of the plurality of microorganisms is cultured in a culture medium containing the carbon source so that production of benzaldehyde from the carbon source is attained, and does not necessarily mean that all of the plurality of microorganisms are cultured in a culture medium containing the carbon source. That is, the phrase "cultivating the microorganism as described herein in a culture medium containing a carbon source" relative to when the microorganism as described herein is a plurality of microorganisms may mean that, for example, at least a microorganism having L-phenylalanine-producing ability, which may be a microorganism having AAD, is cultured in a culture medium containing the carbon source. That is, for example, after cultivation of a microorganism having AAD in a culture medium containing the carbon source to thereby completely consume the carbon source to generate such an intermediate as described later, cultivation of other microorganism(s) may be initiated. For cultivation of microorganism(s) after consumption of the carbon source, any additional carbon source that may be or may not be used as a raw material for production of benzaldehyde can be used as required.

The culture medium to be used is not particularly limited, so long as the microorganism as described herein can proliferate in it and produce benzaldehyde. As the culture medium, for example, a usual culture medium used for culture of microorganisms such as bacteria and yeast can be used. The culture medium may contain carbon source, nitrogen source, phosphate source, and sulfur source, as well as other medium components such as various organic components and inorganic components as required. The types and concentrations of the medium components can be appropriately determined according to various conditions such as the type of the microorganism to be used.

The carbon source is not particularly limited, so long as the microorganism as described herein can utilize it and produce benzaldehyde. Specific examples of the carbon source can include, for example, saccharides such as glucose, fructose, sucrose, lactose, galactose, xylose, arabinose, blackstrap molasses, hydrolysates of starches, and hydrolysates of biomass; organic acids such as acetic acid, citric acid, succinic acid, and gluconic acid; alcohols such as ethanol, glycerol, and crude glycerol; and fatty acids. As the carbon source, plant-derived materials can be used. Examples of the plant can include, for example, corn, rice, wheat, soybean, sugarcane, beet, and cotton. Examples of the plant-derived materials can include, for example, organs such as root, stem, trunk, branch, leaf, flower, and seed, plant bodies including them, and decomposition products of these plant organs. The forms of the plant-derived materials at the time of use thereof are not particularly limited, and they can be used in any form such as unprocessed product, juice, ground product, and purified product. Pentoses such as xylose, hexoses such as glucose, or mixtures of them can be obtained from, for example, plant biomass, and used. Specifically, these saccharides can be obtained by subjecting a plant biomass to such a treatment as steam treatment, hydrolysis with concentrated acid, hydrolysis with diluted acid, hydrolysis with an enzyme such as cellulase, and alkaline treatment. Since hemicellulose is generally more easily hydrolyzed compared with cellulose, hemicellulose in a plant biomass may be hydrolyzed beforehand to liberate pentoses, and then cellulose may be hydrolyzed to generate hexoses. Furthermore, xylose may be supplied by conversion from hexoses by, for example, imparting a pathway for converting hexose such as glucose to xylose to the microorganism as described herein. As the carbon source, one kind of carbon source may be used, or two or more kinds of carbon sources may be used in combination.

The concentration of the carbon source in the medium is not particularly limited, so long as the microorganism as described herein can proliferate and produce benzaldehyde. The concentration of the carbon source in the medium may be as high as possible within such a range that production of benzaldehyde is not inhibited. Initial concentration of the carbon source in the medium may be, for example, usually 5 to 30% (w/v), preferably 10 to 20% (w/v). Furthermore, the carbon source may be additionally supplied to the medium as required. For example, the carbon source may be additionally supplied to the medium in proportion to decrease or deplete the carbon source accompanying progress of the fermentation. While the carbon source may be temporarily depleted so long as benzaldehyde can be eventually produced, it may be preferable to perform the culture so that the carbon source is not depleted or the carbon source does not continue to be depleted.

Specific examples of the nitrogen source can include, for example, ammonium salts such as ammonium sulfate, ammonium chloride, and ammonium phosphate, organic nitrogen sources such as peptone, yeast extract, meat extract, and soybean protein decomposition products, ammonia, and urea. Ammonia gas and aqueous ammonia used for pH adjustment may also be used as a nitrogen source. As the nitrogen source, one kind of nitrogen source may be used, or two or more kinds of nitrogen sources may be used in combination.

Specific examples of the phosphate source can include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source can include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of other various organic and inorganic components can include, for example, inorganic salts such as sodium chloride and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

Furthermore, when an auxotrophic mutant strain that requires a nutrient such as amino acids for growth thereof is used, it is preferable to supplement such a required nutrient to the culture medium.

Culture conditions are not particularly limited, so long as the microorganism as described herein can proliferate, and benzaldehyde is produced. The culture can be performed with, for example, usual conditions used for culture of microorganisms such as bacteria and yeast. The culture conditions may be appropriately determined according to various conditions such as the type of the microorganism to be used. In addition, expression of the benzaldehyde generation enzyme gene(s) may be induced, as required.

The culture can be performed by using a liquid medium. At the time of the culture, for example, the microorganism as described herein cultured on a solid medium such as agar medium may be directly inoculated into a liquid medium, or the microorganism as described herein cultured in a liquid medium as seed culture may be inoculated into a liquid medium for main culture. That is, the culture may be performed separately as seed culture and main culture. In such a case, the culture conditions of the seed culture and the main culture may be or may not be the same. It is sufficient that benzaldehyde is produced at least during the main culture. The amount of the microorganism as described herein contained in the culture medium at the time of the start of the culture is not particularly limited. For example, a seed culture broth showing an OD660 of 4 to 100 may be added to a culture medium for main culture in an amount of 0.1 to 100 mass %, or 1 to 50 mass %, at the time of the start of the culture.

The culture can be performed as batch culture, fed-batch culture, continuous culture, or a combination of these. The culture medium used at the start of the culture can also be referred to as "starting medium". The culture medium supplied to the culture system (e.g. fermentation tank) in the fed-batch culture or the continuous culture can also be referred to as "feed medium". To supply a feed medium to the culture system in the fed-batch culture or the continuous culture can also be referred to as "feed". Furthermore, when the culture is performed separately as seed culture and main culture, the culture schemes of the seed culture and the main culture may be or may not be the same. For example, both the seed culture and the main culture may be performed as batch culture. Alternatively, for example, the seed culture may be performed as batch culture, and the main culture may be performed as fed-batch culture or continuous culture.

The various components such as the carbon source may be contained in the starting medium, feed medium, or both. That is, the various components such as the carbon source may be additionally supplied to the culture medium independently or in an arbitrary combination during the culture. These components may be supplied once or a plurality of times, or may be continuously supplied. The types of the components contained in the starting medium may be or may not be the same as those of the components contained in the feed medium. Furthermore, the concentrations of the components contained in the starting medium may be or may not be the same as the concentrations of the components contained in the feed medium. Furthermore, two or more kinds of feed media containing components of different types and/or different concentrations may be used. For example, when feeding is intermittently performed two or more times, the types and/or concentrations of components contained in the feed medium may be or may not be the same for each feeding.

The culture can be performed, for example, under an aerobic condition. The term "aerobic condition" may refer to a condition where the dissolved oxygen concentration in the culture medium is 0.33 ppm or higher, or 1.5 ppm or higher. The oxygen concentration can be controlled to be, for example, 1 to 50%, or about 5%, of the saturated oxygen concentration. The culture can be performed, for example, with aeration or shaking. The pH of the culture medium may be, for example, 3 to 10, or 4.0 to 9.5. The pH of the culture medium can be adjusted during the culture as required. The pH of the culture medium can be adjusted by using various alkaline and acidic substances such as ammonia gas, aqueous ammonia, sodium carbonate, sodium bicarbonate, potassium carbonate, potassium bicarbonate, magnesium carbonate, sodium hydroxide, calcium hydroxide, and magnesium hydroxide. The culture temperature may be, for example, 20 to 45° C., or 25 to 37° C. The culture time may be, for example, 10 to 120 hours. The culture may be continued, for example, until the carbon source contained in the culture medium is consumed, or until the activity of the microorganism as described herein is lost.

By cultivating the microorganism as described herein under such conditions as described above, benzaldehyde is accumulated in the culture medium.

Production of benzaldehyde can be confirmed by known methods used for detection or identification of compounds. Examples of such methods can include, for example, HPLC, UPLC, LC/MS, GC/MS, and NMR. These methods may be independently used, or may be used in an appropriate combination. These methods can also be used for determining the concentrations of various components present in the culture medium.

The produced benzaldehyde can be appropriately collected. That is, the method as described herein may further include a step of collecting benzaldehyde. This step can also be referred to as "collection step". The collection step may be a step of collecting benzaldehyde from the culture broth, specifically from the culture medium. The produced benzaldehyde can be collected by known methods used for separation and purification of compounds. Examples of such methods can include, for example, ion-exchange resin method, membrane treatment, precipitation, extraction, distillation, and crystallization. Benzaldehyde can be collected specifically by extraction with an organic solvent such as ethyl acetate or by steam distillation. These methods may be independently used, or may be used in an appropriate combination.

Furthermore, when benzaldehyde deposits in the culture medium, it can be collected by, for example, centrifugation or filtration. Benzaldehyde deposited in the culture medium and benzaldehyde dissolving in the culture medium may also be isolated together after benzaldehyde dissolving in the culture medium is crystallized.

The collected benzaldehyde may contain, for example, microbial cells, medium components, moisture, and by-product metabolites of the microorganism, in addition to benzaldehyde. The purity of the collected benzaldehyde may be, for example, 30% (w/w) or higher, 50% (w/w) or higher, 70% (w/w) or higher, 80% (w/w) or higher, 90% (w/w) or higher, or 95% (w/w) or higher.

<2-2> Bioconversion Method

Benzaldehyde can also be produced by, for example, bioconversion using the microorganism as described herein. That is, another embodiment of the method as described herein may be a method for producing benzaldehyde by bioconversion using the microorganism as described herein. This embodiment can also be referred to as "bioconversion method". Also, the step of producing benzaldehyde by bioconversion using the microorganism as described herein can also be referred to as "bioconversion step".

Specifically, in the bioconversion method, benzaldehyde can be produced from L-phenylalanine. More specifically, in the bioconversion method, benzaldehyde can be produced by converting L-phenylalanine into benzaldehyde by using the microorganism as described herein. That is, the bioconversion step may be a step of converting L-phenylalanine into benzaldehyde by using the microorganism as described herein. In the bioconversion step, L-phenylalanine, which is the substance before conversion, can also be referred to as "substrate", and benzaldehyde, which is the substance after conversion, can also be referred to as "product".

L-phenylalanine may be used as a free compound, a salt thereof, or a mixture thereof. That is, the term "L-phenylalanine" used in the present invention can refer to L-phenylalanine in a free form, a salt thereof, or a mixture thereof, unless otherwise stated. Examples of the salt can include, for example, sulfate salt, hydrochloride salt, carbonate salt, ammonium salt, sodium salt, and potassium salt. As the salt, one kind of salt may be employed, or two or more kinds of salts may be employed in combination.

As L-phenylalanine, a commercial product may be used, or one appropriately prepared and obtained may be used. The method for producing L-phenylalanine is not particularly limited, and for example, known methods can be used. L-phenylalanine can be produced by, for example, a chemical synthesis method, enzymatic method, bioconversion method, fermentation method, extraction method, or a combination of these. That is, L-phenylalanine can be produced by, for example, cultivating a microorganism having L-phenylalanine-producing ability (L-phenylalanine-producing microorganism), and collecting L-phenylalanine from the culture broth. The produced L-phenylalanine can be used for the method as described herein as it is, or after being subjected to an appropriate treatment such as concentration, dilution, drying, dissolution, fractionation, extraction, and purification, as required. That is, as L-phenylalanine, for example, a product purified to a desired extent may be used, or a material containing L-phenylalanine may be used. The material containing L-phenylalanine is not particularly limited so long as the microorganism as described herein can use L-phenylalanine. Specific examples of the material containing L-phenylalanine can include culture broth obtained by cultivating a L-phenylalanine-producing microorganism, culture supernatant separated from the culture broth, and processed products thereof such as concentrated products (such as concentrated liquid) thereof and dried products thereof.

In an embodiment, the bioconversion step can be performed by, for example, cultivating the microorganism as described herein. This embodiment can also be referred to as "first embodiment of the bioconversion method". That is, the bioconversion step may be, for example, a step of cultivating the microorganism as described herein in a culture medium containing L-phenylalanine to convert L-phenylalanine into benzaldehyde. The bioconversion step may be, specifically, a step of cultivating the microorganism as described herein in a culture medium containing L-phenylalanine to generate and accumulate benzaldehyde in the culture medium.

When the microorganism as described herein is a plurality of microorganisms, the plurality of microorganisms may be or may not be cultivated simultaneously. For example, the plurality of microorganisms may be inoculated simultaneously and cultivated, or may be inoculated at different times individually or as arbitrary combinations and cultivated. The order and timings for cultivating such a plurality of microorganisms are not particularly limited, so long as conversion of L-phenylalanine into benzaldehyde is attained. For example, a microorganism having AAD, a microorganism having HMAS, a microorganism having SMDH, and a microorganism having BFDC may be inoculated in this order. The phrase "cultivating the microorganism as described herein in a culture medium containing L-phenylalanine" relative to when the microorganism as described herein is a plurality of microorganisms can mean that at least one microorganism of the plurality of microorganisms is cultured in a culture medium containing L-phenylalanine so that conversion of L-phenylalanine into benzaldehyde is attained, and does not necessarily mean that all of the plurality of microorganisms are cultured in a culture medium containing L-phenylalanine. That is, the phrase "cultivating the microorganism as described herein in a culture medium containing L-phenylalanine" relative to when the microorganism as described herein is a plurality of microorganisms may mean that, for example, at least a microorganism having AAD is cultured in a culture medium containing L-phenylalanine. That is, for example, after cultivation of a microorganism having AAD in a culture medium containing L-phenylalanine to thereby completely convert L-phenylalanine into such an intermediate as described later, cultivation of other microorganism(s) may be initiated.

The culture medium to be used is not particularly limited, so long as the culture medium contains L-phenylalanine, and the microorganism as described herein can proliferate in it and produce benzaldehyde. Culture conditions are not particularly limited, so long as the microorganism as described herein can proliferate, and benzaldehyde is produced. The descriptions concerning the culture mentioned for the fermentation method, such as those concerning the culture medium and culture conditions, can be applied mutatis mutandis to the culture in the first embodiment of the bioconversion method, except that the culture medium contains L-phenylalanine in this embodiment.

L-phenylalanine may be present in the culture medium over the whole period of the culture, or may be present in the culture medium during only a partial period of the culture. That is, the phrase "cultivating a microorganism in a culture medium containing L-phenylalanine" does not necessarily mean that L-phenylalanine is present in the culture medium over the entire period of the culture. For example, L-phenylalanine may be or may not be present in the culture medium from the start of the culture. When L-phenylalanine is not present in the culture medium at the time of the start of the culture, L-phenylalanine is supplied to the culture medium after the start of the culture. Timing of the supply can be appropriately determined according to various conditions such as the length of the culture period. For example, after the microorganism as described herein sufficiently grows, L-phenylalanine may be supplied to the culture medium. Furthermore, in any case, L-phenylalanine may be additionally supplied to the culture medium as required. For example, L-phenylalanine may be additionally supplied to the culture medium in proportion to decrease or deplete L-phenylalanine accompanying generation of benzaldehyde. Methods for supplying L-phenylalanine to the culture medium is not particularly limited. For example, L-phenylalanine can be supplied to the culture medium by feeding a feed medium containing L-phenylalanine to the culture medium. Furthermore, for example, the microorganism as described herein and an L-phenylalanine-producing microorganism can be co-cultured to allow the L-phenylalanine-producing microorganism to produce L-phenylalanine in the culture medium, and thereby supply L-phenylalanine to the culture medium. These supply methods may be independently used, or may be used in an appropriate combination. The concentration of L-phenylalanine in the culture medium is not particularly limited so long as the microorganism as described herein can use L-phenylalanine as a raw material of benzaldehyde. The concentration of L-phenylalanine in the culture medium, for example, may be 1 mM or higher, 10 mM or higher, or 30 mM or higher, or may be 5 M or lower, 2 M or lower, or 1 M or lower, or may be within a range defined with a combination thereof. L-phenylalanine may be or may not be contained in the culture medium at a concentration within the range exemplified above over the whole period of the culture. For example, L-phenylalanine may be contained in the culture medium at a concentration within the range exemplified above at the time of the start of the culture, or it may be supplied to the culture medium so that a concentration within the range exemplified above is attained after the start of the culture. In cases where the culture is performed separately as seed culture and main culture, it is sufficient that benzaldehyde is produced at least during the main culture. Hence, it is sufficient that L-phenylalanine is contained in the culture medium at least during the main culture, i.e. over the whole period of the main culture or during a partial period of the main culture, and that is, L-phenylalanine may be or may not be contained in the culture medium during the seed culture. In such cases, terms regarding the culture, such as “culture period (period of culture)” and “start of culture”, can be read as those regarding the main culture.

In another embodiment, the bioconversion step can also be performed by, for example, using cells of the microorganism as described herein. This embodiment can also be referred to as “second embodiment of the bioconversion method”. That is, the bioconversion step may be, for example, a step of converting L-phenylalanine in a reaction mixture into benzaldehyde by using cells of the microorganism as described herein. The bioconversion step may be, specifically, a step of allowing cells of the microorganism as described herein to coexist with L-phenylalanine in a reaction mixture to generate and accumulate benzaldehyde in the reaction mixture. The bioconversion step may be, more specifically, a step of allowing cells of the microorganism as described herein to act on L-phenylalanine in a reaction mixture to generate and accumulate benzaldehyde in the reaction mixture. The bioconversion step performed by using such cells can also be referred to as “conversion reaction”.

When the microorganism as described herein is a plurality of microorganisms, the plurality of microorganisms may be or may not be supplied to the reaction mixture simultaneously. For example, the plurality of microorganisms may be supplied to the reaction mixture at different times individually or as arbitrary combinations. The order and timing for supplying such a plurality of microorganisms to the reaction mixture are not particularly limited, so long as conversion of L-phenylalanine into benzaldehyde is attained. For example, cells of a microorganism having AAD, cells of a microorganism having HMAS, cells of a microorganism having SMDH, and cells of a microorganism having BFDC may be supplied to the reaction mixture in this order. The phrase “allowing cells of the microorganism as described herein to coexist with or act on L-phenylalanine in a reaction mixture” relative to when the microorganism as described herein is a plurality of microorganisms can mean that cells of at least one microorganism of the plurality of microorganisms are allowed to coexist with or act on L-phenylalanine in a reaction mixture so that conversion of L-phenylalanine into benzaldehyde is attained, and does not necessarily mean that cells of all the plurality of microorganisms are allowed to coexist with or act on L-phenylalanine in a reaction mixture. That is, the phrase “allowing cells of the microorganism as described herein to coexist with or act on L-phenylalanine in a reaction mixture” relative to when the microorganism as described herein is a plurality of microorganisms may mean that, for example, cells of at least a microorganism having AAD are allowed to coexist with or act on L-phenylalanine in a reaction mixture. That is, for example, after allowing cells of a microorganism having AAD to coexist with or act on L-phenylalanine in a reaction mixture to thereby completely convert L-phenylalanine into such an intermediate as described later, cells of other microorganism(s) may be supplied to the reaction mixture.

Cells of the microorganism as described herein can be obtained by cultivating the microorganism as described herein. The culture method for obtaining the cells is not particularly limited so long as the microorganism as described herein can proliferate. At the time of the culture for obtaining the cells, L-phenylalanine may be or may not be contained in the culture medium. Also, at the time of the culture for obtaining the cells, benzaldehyde may be or may not be produced in the culture medium. The descriptions concerning the culture mentioned for the fermentation method, such as those concerning the culture medium and culture conditions, can be applied mutatis mutandis to the culture for obtaining the cells used for the second embodiment of the bioconversion method.

The cells may be used for the conversion reaction while being present in the culture medium (culture broth), or after being collected from the culture medium (culture broth). The cells may also be used for the conversion reaction after being subjected to a treatment as required. That is, examples of the cells can include a culture broth containing the cells, the cells collected from the culture broth, or a processed product thereof. Examples of the processed product can include products obtained by subjecting the cells (such as a culture broth containing the cells, or the cells collected from the culture broth) to a treatment. Cells in these forms may be independently used, or may be used in an appropriate combination.

The method for collecting the cells from the culture medium is not particularly limited, and for example, known methods can be used. Examples of such methods can include, for example, spontaneous precipitation, centrifugation, and filtration. A flocculant may also be used. These methods may be independently used, or may be used in an appropriate combination. The collected cells can be washed as required by using an appropriate medium. The collected cells can be re-suspended as required by using an appropriate medium. Examples of the medium usable for washing or suspending the cells can include, for example, aqueous media (aqueous solvents) such as water and aqueous buffer.

Examples of the treatment of the cells can include, for example, dilution, condensation, immobilization on a carrier such as acrylamide and carrageenan, freezing and thawing treatment, and treatment for increasing permeability of cell membranes. Permeability of cell membranes can be increased by, for example, using a surfactant or organic solvent. These treatments may be independently used, or may be used in an appropriate combination.

The cells used for the conversion reaction are not particularly limited so long as the cells have the benzaldehyde-producing ability. The cells may have or may not have proliferation ability.

The conversion reaction can be carried out in an appropriate reaction mixture. Specifically, the conversion reaction can be carried out by allowing the cells and L-phenylalanine to coexist in an appropriate reaction mixture. The conversion reaction may be carried out by the batch method or may be carried out by the column method. In the case of the batch method, the conversion reaction can be carried out by, for example, mixing the cells of the microorganism as described herein and L-phenylalanine in a reaction mixture contained in a reaction vessel. The conversion reaction may be carried out statically, or may be carried out with stirring or shaking the reaction mixture. In the case of the column method, the conversion reaction can be carried out by, for example, passing a reaction mixture containing L-phenylalanine through a column filled with immobilized cells. Examples of the reaction mixture can include those based on an aqueous medium (aqueous solvent) such as water and aqueous buffer.

The reaction mixture may contain components other than L-phenylalanine as required, in addition to L-phenylalanine. Examples of the components other than L-phenylalanine can include oxygen, metal ions such as ferric ion, buffering agents, and other various medium components. The types and concentrations of the components contained in the reaction mixture may be determined according to various conditions such as the type of microorganism to be used.

Conditions of the conversion reaction, such as dissolved oxygen concentration, pH of the reaction mixture, reaction temperature, reaction time, concentrations of various components, etc., are not particularly limited so long as benzaldehyde is generated. The conversion reaction can be performed with, for example, usual conditions used for substance conversion using microbial cells such as resting cells. The conditions of the conversion reaction may be determined according to various conditions such as the type of microorganism to be used. The conversion reaction can be performed, for example, under aerobic conditions. The term "aerobic conditions" may refer to a condition where the dissolved oxygen concentration in the reaction mixture is 0.33 ppm or higher, or preferably 1.5 ppm or higher. The oxygen concentration can be controlled to be, for example, 1 to 50%, or about 5%, of the saturated oxygen concentration. The pH of the reaction mixture may be, for example, usually 6.0 to 10.0, or 6.5 to 9.0. The reaction temperature may be, for example, usually 15 to 50° C., 15 to 45° C., or 20 to 40° C. The reaction time may be, for example, 5 minutes to 200 hours. In the case of the column method, the loading rate of the reaction mixture may be, for example, such a rate that the reaction time falls within the range of the reaction time exemplified above. Furthermore, the conversion reaction can also be performed with, for example, a culture condition, such as usual conditions used for culture of microorganisms such as bacteria and yeast. During the conversion reaction, the cells may or may not proliferate. That is, the descriptions concerning the culture conditions mentioned for the first embodiment of the bioconversion method may also be applied mutatis mutandis to the conditions of the conversion reaction in the second embodiment of the bioconversion method, except that the cells may or may not proliferate in the second embodiment. In such a case, the culture conditions for obtaining the cells and the conditions of the conversion reaction may be or may not be the same. The concentration of L-phenylalanine in the reaction mixture, for example, may be 1 mM or higher, 10 mM or higher, or 30 mM or higher, or may be 5 M or lower, 2 M or lower, or 1 M or lower, or may be within a range defined with a combination thereof. The density of the cells in the reaction mixture, for example, may be 1 or higher, or may be 300 or lower, or may be within a range defined with a combination thereof.

During the conversion reaction, the cells, L-phenylalanine, and the other components may be additionally supplied to the reaction mixture independently or in any arbitrary combination thereof. For example, L-phenylalanine may be additionally supplied to the reaction mixture in proportion to decrease or depletion of L-phenylalanine accompanying generation of benzaldehyde. These components may be supplied once or a plurality of times, or may be continuously supplied.

Methods for supplying the various components such as L-phenylalanine to the reaction mixture is not particularly limited. These components each can be supplied to the reaction mixture by, for example, directly adding them to the reaction mixture. Furthermore, for example, the microorganism as described herein and an L-phenylalanine-producing microorganism can be co-cultured to allow the L-phenylalanine-producing microorganism to produce L-phenylalanine in the reaction mixture, and thereby supply L-phenylalanine to the reaction mixture.

Furthermore, the reaction conditions may be constant from the start to the end of the conversion reaction, or they may be changed during the conversion reaction. The expression "the reaction conditions are changed during the conversion reaction" can include not only cases where the reaction conditions are temporally changed, but also can include cases where the reaction conditions are spatially changed. The expression "the reaction conditions are spatially changed" can mean that, for example, when the conversion reaction is performed by the column method, the reaction conditions such as reaction temperature and cell density differ depending on position in the flow.

A culture medium (i.e. culture broth) or reaction mixture containing benzaldehyde is obtained by carrying out the bioconversion step as described above. Confirmation of the production of benzaldehyde and collection of benzaldehyde can be carried out in the same manners as those for the fermentation method described above. That is, the bioconversion method may further include the collection step, e.g. a step of collecting benzaldehyde from the culture broth (or culture medium) or reaction mixture. The collected benzaldehyde may contain, for example, microbial cells, medium components, reaction mixture components, moisture, and by-product metabolites of the microorganism, in addition to benzaldehyde. Purity of the collected benzaldehyde may be, for example, 30% (w/w) or higher, 50% (w/w) or higher, 70% (w/w) or higher, 80% (w/w) or higher, 90% (w/w) or higher, or 95% (w/w) or higher.

<2-3> Combination of Substeps

The production step, such as the fermentation step and bioconversion step, may be performed, but is not limited to, via generation of an intermediate. Examples of the intermediate can include phenylpyruvate, (S)-mandelate, and benzoylformate, which are the products of reactions catalyzed by AAD, HMAS, and SMDH, respectively. In the array of phenylpyruvate, (S)-mandelate, and benzoylformate, the side of phenylpyruvate can also be referred to as "upstream", and the side of benzoylformate can also be referred to as "downstream". That is, the production step may include a plurality of steps, wherein the plurality of steps is accompanied by generation of one or more intermediates. Each of the plurality of steps that make up the production step can also be referred to as "substep". The production step may include, for example, 2, 3, or 4 substeps. Examples of the substeps of the production step can include a fermentation substep and a bioconversion substep. Examples of the fermentation substep can include a step of producing an intermediate from a carbon source. Examples of the bioconversion substep can include a step of converting L-phenylalanine into an intermediate, a step of converting an intermediate into another downstream intermediate, and a step of converting an intermediate into benzaldehyde. The combination of the substeps of the production step is not particularly limited, so long as production of benzaldehyde is attained.

The production step may include, for example, a step of producing an intermediate from a carbon source, and a step of converting the intermediate into benzaldehyde. That is, the production step may include, for example, a step of producing phenylpyruvate, (S)-mandelate, or benzoylformate from a carbon source, and a step of converting phenylpyruvate, (S)-mandelate, or benzoylformate into benzaldehyde. Specifically, the production step may include, for example, a step of producing benzoylformate from a carbon source, and a step of converting benzoylformate into benzaldehyde. Furthermore, the production step may include, for example, a step of producing an intermediate A from a carbon source, a step of converting the intermediate A into another downstream intermediate B, and a step of converting the intermediate B into benzaldehyde. Furthermore, the production step may include, for example, a step of producing phenylpyruvate from a carbon source, a step of converting phenylpyruvate into (S)-mandelate, a step of converting (S)-mandelate into benzoylformate, and a step of converting benzoylformate into benzaldehyde.

The production step may also include, for example, a step of converting L-phenylalanine into an intermediate, and a step of converting the intermediate into benzaldehyde. That is, the production step may include, for example, a step of converting L-phenylalanine into phenylpyruvate, (S)-mandelate, or benzoylformate, and a step of converting phenylpyruvate, (S)-mandelate, or benzoylformate into benzaldehyde. Specifically, the production step may include, for example, a step of converting L-phenylalanine into benzoylformate, and a step of converting benzoylformate into benzaldehyde. Furthermore, the production step may include, for example, a step of converting L-phenylalanine into an intermediate A, a step of converting the intermediate A into another downstream intermediate B, and a step of converting the intermediate B into benzaldehyde. Furthermore, the production step may include, for example, a step of converting L-phenylalanine into phenylpyruvate, a step of converting phenylpyruvate into (S)-mandelate, a step of converting (S)-mandelate into benzoylformate, and a step of converting benzoylformate into benzaldehyde.

Furthermore, each substep of the production step may include further substeps, as with the production step. The descriptions concerning the production step and substeps thereof can be applied mutatis mutandis to each substep of the production step and further substeps thereof. That is, for example, a step of converting L-phenylalanine into benzoylformate may include a step of converting L-phenylalanine into phenylpyruvate, a step of converting phenylpyruvate into (S)-mandelate, and a step of converting (S)-mandelate into benzoylformate. In each fermentation substep, the intermediate to be produced can also be referred to as "product". In each bioconversion substep, the substance before conversion can also be referred to as "substrate", and the substance after conversion can also be referred to as "product". That is, for example, in a step of converting L-phenylalanine into an intermediate, L-phenylalanine is considered as the substrate, and the intermediate is considered as the product.

The descriptions concerning the methods for carrying out the fermentation step can be applied mutatis mutandis to the methods for carrying out each fermentation substep of the production step. The descriptions concerning the methods for carrying out the bioconversion step can be applied mutatis mutandis to the methods for carrying out each bioconversion substep of the production step. In this case, "the microorganism as described herein" used in the production step can be read as a microorganism having benzaldehyde generation enzyme(s) corresponding to each substep. Furthermore, "benzaldehyde", which is the product of the fermentation step, can be read as the corresponding product of each fermentation substep. Also, "L-phenylalanine" and "benzaldehyde", which are the substrate and product of the bioconversion step, can be read as the corresponding substrate and product of each bioconversion substep, respectively. In each bioconversion substep, the product generated in the immediately preceding substep is used as the substrate, except for L-phenylalanine. The substrate of each bioconversion substep may be used as a free compound, a salt thereof, or a mixture thereof. The descriptions concerning the salt of L-phenylalanine can be applied mutatis mutandis to the salt of other substrates.

Each substep of the production step is performed by using a microorganism having benzaldehyde generation enzyme (s) corresponding to the substep. The term "benzaldehyde generation enzyme(s) corresponding to a substep of the production step" used for each fermentation substep can refer to a single enzyme or sequential enzymes that catalyze the conversion of L-phenylalanine into the product of the substep. Also, the term "benzaldehyde generation enzyme(s) corresponding to a substep of the production step" used for each bioconversion substep can refer to a single enzyme or sequential enzymes that catalyze the conversion of the substrate of the substep into the product of the substep. That is, for example, a step of producing phenylpyruvate from a carbon source or converting L-phenylalanine into phenylpyruvate, a step of converting phenylpyruvate into (S)-mandelate, a step of converting (S)-mandelate into benzoylformate, and a step of converting benzoylformate into benzaldehyde are performed by using a microorganism having AAD, a microorganism having HMAS, a microorganism having SMDH, and a microorganism having BFDC, respectively. Furthermore, for example, a step of producing phenylpyruvate, (S)-mandelate, or benzoylformate from a carbon source or converting L-phenylalanine into phenylpyruvate, (S)-mandelate, or benzoylformate is performed by using a microorganism having AAD, a microorganism having AAD and HMAS, or a microorganism having AAD, HMAS, and SMDH, respectively. Furthermore, for example, step of converting phenylpyruvate, (S)-mandelate, or benzoylformate into benzaldehyde is performed by using a microorganism having HMAS, SMDH, and BFDC, a microorganism having SMDH and BFDC, or a microorganism having BFDC, respectively. For any other substep, microorganism having the benzaldehyde generation enzyme(s) required for the substep can be appropriately employed.

When a microorganism having a plurality of benzaldehyde generation enzymes is used for a substep of the production step, the microorganism may be a single microorganism, or may be a plurality of microorganisms. The descriptions concerning the microorganism as described herein (i.e. the microorganism having the four benzaldehyde generation enzymes) can be applied mutatis mutandis to the microorganism having a plurality of benzaldehyde generation enzymes. That is, for example, the microorganism having AAD, HMAS, and SMDH may be a single microorganism solely having AAD, HMAS, and SMDH, or may be a plurality of microorganisms having AAD, HMAS, and SMDH as a whole.

A microorganism used for a certain substep of the production step may be different from or the same as a microorganism used for another substep of the production step. That is, when a single microorganism solely has benzaldehyde generation enzyme(s) corresponding to a certain substep and benzaldehyde generation enzyme(s) corresponding to another substep, the microorganism can be used commonly for these substeps.

Each substep of the production step may be performed by, for example, cultivating the microorganism having benzaldehyde generation enzyme(s) corresponding to the substep, or using cells of the microorganism having benzaldehyde generation enzyme(s) corresponding to the substep. That is, each fermentation substep of the production step may also be a step of cultivating the microorganism having benzaldehyde generation enzyme(s) corresponding to the substep and having L-phenylalanine-producing ability in a culture medium containing a carbon source to generate and accumulate the corresponding product in the culture medium. Furthermore, each bioconversion substep of the production step may be a step of cultivating the microorganism having benzaldehyde generation enzyme(s) corresponding to the substep in a culture medium containing the corresponding substrate to generate and accumulate the corresponding product in the culture medium. Each bioconversion substep of the production step may also be a step of allowing cells of the microorganism having benzaldehyde generation enzyme(s) corresponding to the substep to coexist with the corresponding substrate in a reaction mixture to generate and accumulate the corresponding product in the reaction mixture. All the substeps of the production step may be performed by cultivation or by using the cells. Alternatively, a part of the substeps may be performed by cultivation, while the remaining part of the substeps may be performed by using the cells. Conditions for carrying out each substep of the production step may be appropriately chosen depending on the various conditions such as type(s) of benzaldehyde generation enzyme(s) corresponding to the substep and type(s) of microorganism(s) used in the substep.

That is, specifically, for example, the production step may include the steps (1) and (2) mentioned below:

(1) the step (1a) or (1b) mentioned below:

(1a) cultivating at least one microorganism in a culture medium containing the carbon source to generate and accumulate benzoylformate in the culture medium, which at least one microorganism has amino acid deaminase, 4-hydroxymandelate synthase, and (S)-mandelate dehydrogenase and has L-phenylalanine-producing ability;

(1b) cultivating at least one microorganism in a culture medium containing L-phenylalanine to generate and accumulate benzoylformate in the culture medium, or allowing cells of the at least one microorganism to coexist with L-phenylalanine in a reaction mixture to generate and accumulate benzoylformate in the reaction mixture, which at least one microorganism has amino acid deaminase, 4-hydroxymandelate synthase, and (S)-mandelate dehydrogenase;

(2) cultivating a microorganism in a culture medium containing benzoylformate generated in the step (1) to generate and accumulate benzaldehyde in the culture medium, or allowing cells of the microorganism to coexist with benzoylformate generated in the step (1) in a reaction mixture to generate and accumulate benzaldehyde in the reaction mixture, which microorganism has benzoylformate decarboxylase.

The substeps of the production step may be or may not be performed individually. That is, a part or all of the substeps of the production step may be performed simultaneously during a partial period or over the whole period. For example, a substep A that generates a product and a substep B that uses the product as a substrate may be performed individually, or may be performed simultaneously during a partial period or over the whole period. That is, for example, the substeps A and B may be initiated simultaneously, or the substep B may be initiated during progress of or after completion of the substep A. For example, the substeps A and B can be initiated simultaneously by allowing a microorganism having the benzaldehyde generation enzymes corresponding to the substeps A and B to coexist with the substrate of the substep A in the reaction system (e.g. reaction mixture or culture medium) at start of the substep A. Alternatively, for example, the substep A can be initiated under conditions where a microorganism having the benzaldehyde generation enzyme(s) corresponding to the substep B does not present in the reaction system, and then the substep B can be initiated by allowing the microorganism having the benzaldehyde generation enzyme(s) corresponding to the substep B to present in the reaction system during progress of or after completion of the substep A. Furthermore, the product of the substep A may be or may not be collected before use. That is, for example, the product of the substep A may be collected, and the substep B may be performed by using the thus-collected product. The product of the substep A may be used for the substep B as it is, or after being subjected to an appropriate treatment such as concentration, dilution, drying, dissolution, fractionation, extraction, and purification, as required. These descriptions concerning the substeps A and B can be applied to any combination of successive substeps.

EXAMPLES

Hereinafter, the present invention will be more specifically explained with reference to the following non-limiting examples.

Example 1: Expression of Amino Acid Deaminase (AAD) Native to *Providencia rettgeri* AJ2770

<1> Construction of Plasmid pSFN-AAD for Expression of Amino Acid Deaminase Native to *Providencia rettgeri* AJ2770

A plasmid harboring the amino acid deaminase gene native to *Providencia rettgeri* AJ2770 was extracted from *E. coli* pTB2 (WO2009/028338, Example 2). By using the plasmid as the template, a DNA fragment containing the amino acid deaminase gene was PCR-amplified. As primers, NdeI-aad-5R6R8L-F (5'-GGGAATTCCATATGAAAATCTCGcGtcGtAAGCTgTTATTAGGGGTTGGT-3'; SEQ ID NO: 1) and aad-HindIII-R (5'-CCCAAGCTTTTAGCTAAAACGGGAAAGTTTATA-3'; SEQ ID NO: 2)

were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 55° C., 10 sec |
| | 68° C., 90 sec |
| 1 cycle | 68° C., 90 sec |
| | 4° C. |

The obtained DNA fragment of about 1400 bp was treated with restriction enzymes NdeI and HindIII, and ligated with pSFN Sm_Aet (WO2006/075486, Examples 1, 6, and 12) similarly treated with NdeI and HindIII. *E. coli* JM109 was transformed with this ligation mixture, an objective plasmid was extracted from an ampicillin resistant strain, and the plasmid was designated as pSFN-AAD. The nucleotide sequence of the AAD gene harbored by pSFN-AAD is shown as SEQ ID NO: 11, and the amino acid sequence of AAD encoded by this gene is shown as SEQ ID NO: 12.

<2> Preparation for Culture Broth of Strain Expressing Amino Acid Deaminase Native to *Providencia rettgeri* AJ2770

*E. coli* JM109 introduced with the amino acid deaminase expression plasmid pSFN-AAD was cultured overnight at 25° C. on LB-amp (100 mg/L) plate, i.e. LB plate containing 100 mg/L of ampicillin. The obtained cells were inoculated into 100 mL of TB-amp (100 mg/L), i.e. TB medium containing 100 mg/L of ampicillin, contained in a Sakaguchi flask, and cultured at 25° C. with shaking for 16 hr. The obtained culture broth was hereinafter used as AAD culture broth.

Example 2: Expression of 4-Hydroxymandelate Synthase (HMAS)

<1> Construction of Expression Plasmids for 4-Hydroxymandelate Synthase

Expression plasmids for 4-hydroxymandelate synthase (HMAS), pET22-hmaS Ao, pET22-hmaS Sc, pET22-hmaS Rr, pET22-hmaS St, pET22-hmaS At, pET22-hmaS Ab, pET22-hmaS Ka, pET22-hmaS Nc, pET22-hmaS Ar, pET22-hmaS As, pET22-hmaS Sr, and pET22-hmaS Ha, were constructed via the following procedures. In addition, for comparison, expression plasmids for 4-hydroxyphenylpyruvate dioxygenase (HPPD), pET22-HPPD Sa and pET22-HPPD Pp, were constructed via the following procedures. HPPD is one of the alpha-keto acid oxygenase, as with HMAS. HPPD acts on the same substrate as that of HMAS, while HPPD generates a product different from that of HMAS.

<1-1> Construction of Plasmid pET22-hmaS Ao for Expression of 4-Hydroxymandelate Synthase Native to *Amycolatopsis orientalis*

Synthesis of a gene encoding 4-hydroxymandelate synthase native to *Amycolatopsis orientalis* (GenBank Accession Number: WP_037311069) was outsourced to Life Technologies, and a plasmid inserted with a DNA fragment containing the gene was obtained. The gene had been codon-optimized for expression in *E. coli*. By using the plasmid as the template, a DNA fragment containing the 4-hydroxymandelate synthase gene was PCR-amplified. As primers, NdeI-hmaS Ao-F (5'-ggaattccatATGCAGAACTTTGAAATCGA-3'; SEQ ID NO: 3) and hmaS Ao-XhoI-R (5'-accgctcgagTCAACGACCGGCAACTTCGC-3'; SEQ ID NO: 4) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1000 bp was treated with restriction enzymes NdeI and XhoI, and ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Ao. The nucleotide sequence of the HMAS gene harbored by pET22-hmaS Ao is shown as SEQ ID NO: 13, and the amino acid sequence of HMAS encoded by this gene is shown as SEQ ID NO: 14.

<1-2> Construction of Plasmid pET22-hmaS Sc for Expression of 4-Hydroxymandelate Synthase Native to *Streptomyces coelicolor*

Synthesis of a gene encoding 4-hydroxymandelate synthase native to *Streptomyces coelicolor* (GenBank Accession Number: WP_011028841) was outsourced to Life Technologies, and a plasmid inserted with a DNA fragment containing the gene was obtained. The gene had been codon-optimized for expression in *E. coli*. By using the plasmid as the template, a DNA fragment containing the 4-hydroxymandelate synthase gene was PCR-amplified. As primers, AseI-hmaS Sc-F (5'-ggaattcattaATGCTGCCTCCGTTTCCGT-3'; SEQ ID NO: 5) and hmaS Sc-XhoI-R (5'-accgctcgagTCAACGACGTGCCGGACCCA-3'; SEQ ID NO: 6) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1100 bp was treated with restriction enzymes AseI and XhoI, and ligated with pET22b (Novagen) treated with NdeI and XhoI. *E. coli* JM109 was transformed with this ligation mixture, an objective plasmid was extracted from an ampicillin resistant strain, and the plasmid was designated as pET22-hmaS Sc. The nucleotide sequence of the HMAS gene harbored by pET22-hmaS Sc is shown as SEQ ID NO: 15, and the amino acid sequence of HMAS encoded by this gene is shown as SEQ ID NO: 16.

<1-3> Construction of Plasmid pET22-hmaS Rr for Expression of 4-Hydroxymandelate Synthase Native to *Rhodococcus rhodnii*

Synthesis of a gene encoding 4-hydroxymandelate synthase native to *Rhodococcus rhodnii* (GenBank Accession Number: WP_037255771) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Rr. The nucleotide sequence of the HMAS gene harbored by pET22-hmaS Rr is shown as SEQ ID NO: 19, and the amino acid sequence of HMAS encoded by this gene is shown as SEQ ID NO: 20.

<1-4> Construction of Plasmid pET22-hmaS St for Expression of 4-Hydroxymandelate Synthase Native to *Streptomyces* Toyocaensis Synthesis of a gene encoding 4-hydroxymandelate synthase native to *Streptomyces* toyocaensis (GenBank Accession Number: AAM80551) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS St. The nucleotide sequence of the HMAS gene harbored by pET22-hmaS St is shown as SEQ ID NO: 17, and the amino acid sequence of HMAS encoded by this gene is shown as SEQ ID NO: 18.

<1-5> Construction of Plasmid pET22-hmaS at for Expression of 4-Hydroxymandelate Synthase Native to *Actinoplanes teichomyceticus*

Synthesis of a gene encoding 4-hydroxymandelate synthase native to *Actinoplanes teichomyceticus* (GenBank Accession Number: CAG15040) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS At. The nucleotide sequence of the HMAS gene harbored by pET22-hmaS At is shown as SEQ ID NO: 21, and the amino acid sequence of HMAS encoded by this gene is shown as SEQ ID NO: 22.

<1-6> Construction of Plasmid pET22-hmaS Ab for Expression of 4-Hydroxymandelate Synthase Native to *Amycolatopsis balhimycina*

Synthesis of a gene encoding 4-hydroxymandelate synthase native to *Amycolatopsis balhimycina* (GenBank Accession Number: CAC48371) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Ab. The nucleotide sequence of the HMAS gene harbored by pET22-hmaS Ab is shown as SEQ ID NO: 32, and the amino acid sequence of HMAS encoded by this gene is shown as SEQ ID NO: 33.

<1-7> Construction of Plasmid pET22-hmaS Ka for Expression of 4-Hydroxymandelate Synthase Native to *Kibdelosporangium Aridum*

Synthesis of a gene encoding 4-hydroxymandelate synthase native to *Kibdelosporangium aridum* (GenBank Accession Number: WP_051895522) was outsourced to Eurofins Genomics, and a plasmid inserted with a DNA fragment containing the gene was obtained. The gene had been codon-optimized for expression in *E. coli*. A DNA fragment of about 1000 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Ka. The nucleotide sequence of the HMAS gene harbored by pET22-hmaS Ka is shown as SEQ ID NO: 34, and the amino acid sequence of HMAS encoded by this gene is shown as SEQ ID NO: 35.

<1-8> Construction of Plasmid pET22-hmaS Nc for Expression of 4-Hydroxymandelate Synthase Native to *Nonomuraea coxensis*

Synthesis of a gene encoding 4-hydroxymandelate synthase native to *Nonomuraea coxensis* (GenBank Accession Number: WP_026214630) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Nc. The nucleotide sequence of the HMAS gene harbored by pET22-hmaS Nc is shown as SEQ ID NO: 36, and the amino acid sequence of HMAS encoded by this gene is shown as SEQ ID NO: 37.

<1-9> Construction of Plasmid pET22-hmaS Ar for Expression of 4-Hydroxymandelate Synthase Native to *Actinoplanes rectilineatus*

Synthesis of a gene encoding 4-hydroxymandelate synthase native to *Actinoplanes rectilineatus* (GenBank Accession Number: WP_045739980) was outsourced to Eurofins Genomics, and a plasmid inserted with a DNA fragment containing the gene was obtained. The gene had been codon-optimized for expression in *E. coli*. A DNA fragment of about 1000 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Ar. The nucleotide sequence of the HMAS gene harbored by pET22-hmaS Ar is shown as SEQ ID NO: 38, and the amino acid sequence of HMAS encoded by this gene is shown as SEQ ID NO: 39.

<1-10> Construction of Plasmid pET22-hmaS as for Expression of 4-Hydroxymandelate Synthase Native to *Actinoplanes subtropicus*

Synthesis of a gene encoding 4-hydroxymandelate synthase native to *Actinoplanes subtropicus* (GenBank Accession Number: WP_030437841) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS As. The nucleotide sequence of the HMAS gene harbored by pET22-hmaS As is shown as SEQ ID NO: 40, and the amino acid sequence of HMAS encoded by this gene is shown as SEQ ID NO: 41.

<1-11> Construction of Plasmid pET22-hmaS Sr for Expression of 4-Hydroxymandelate Synthase Native to *Streptomyces rimosus*

Synthesis of a gene encoding 4-hydroxymandelate synthase native to *Streptomyces rimosus* (GenBank Accession Number: WP_050515337) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Sr. The nucleotide sequence of the HMAS gene harbored by pET22-hmaS Sr is shown as SEQ ID NO: 42, and the amino acid sequence of HMAS encoded by this gene is shown as SEQ ID NO: 43.

<1-12> Construction of Plasmid pET22-hmaS Ha for Expression of 4-Hydroxymandelate Synthase Native to *Herpetosiphon aurantiacus*

Synthesis of a gene encoding 4-hydroxymandelate synthase native to *Herpetosiphon aurantiacus* (GenBank Accession Number: ABX04531) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS Ha. The nucleotide sequence of the HMAS gene harbored by pET22-hmaS Ha is shown as SEQ ID NO: 44, and the amino acid sequence of HMAS encoded by this gene is shown as SEQ ID NO: 45.

<1-13> Construction of Plasmid pET22-HPPD Sa for Expression of 4-Hydroxyphenylpyruvate Dioxygenase Native to *Streptomyces avermitilis*

Synthesis of a gene encoding 4-hydroxyphenylpyruvate dioxygenase native to *Streptomyces avermitilis* (GenBank Accession Number: WP_010986553) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-HPPD Sa. The nucleotide sequence of the HPPD gene harbored by pET22-HPPD Sa is shown as SEQ ID NO: 23, and the amino acid sequence of HPPD encoded by this gene is shown as SEQ ID NO: 24.

<1-14> Construction of Plasmid pET22-HPPD Pp for Expression of 4-Hydroxyphenylpyruvate Dioxygenase Native to *Pseudomonas putida*

Synthesis of a gene encoding 4-hydroxyphenylpyruvate dioxygenase native to *Pseudomonas putida* (GenBank Accession Number: WP_046820065) was outsourced to Eurofins Genomics, and a plasmid inserted with a DNA fragment containing the gene was obtained. The gene had been codon-optimized for expression in *E. coli*. A DNA fragment of about 1100 bp obtained by treating the plasmid with restriction enzymes NdeI and XhoI was ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-HPPD Pp. The nucleotide sequence of the HPPD gene harbored by pET22-HPPD Pp is shown as SEQ ID NO: 25, and the amino acid sequence of HPPD encoded by this gene is shown as SEQ ID NO: 26.

<2> Preparation for Culture Broth of Strains Expressing 4-Hydroxymandelate Synthase

*E. coli* BL21(DE3) was introduced with the expression plasmid pET22-hmaS Ao for 4-hydroxymandelate synthase native to *Amycolatopsis orientalis*, and a transformant strain harboring this plasmid was obtained from ampicillin resistant strains. The transformant strain was cultured overnight at 30° C. on LB-amp (100 mg/L) plate. The obtained cells were inoculated into 100 mL of Overnight Express Instant TB Medium (Novagen) containing 100 mg/L of ampicillin contained in a Sakaguchi flask, and cultured at 30° C. with shaking for 16 hr. The obtained culture broth was hereinafter used as HMAS Ao culture broth. Similarly, HMAS Sc culture broth, HMAS Rr culture broth, HMAS St culture broth, HMAS At culture broth, HMAS Ab culture broth, HMAS Ka culture broth, HMAS Nc culture broth, HMAS Ar culture broth, HMAS As culture broth, HMAS Sr culture broth, HMAS Ha culture broth, HPPD Sa culture broth, and HPPD Pp culture broth were obtained.

Example 3: Expression of (S)-Mandelate Dehydrogenase (MdlB, SMDH) Native to *Pseudomonas putida*

<1> Construction of Plasmid for Expression of (S)-Mandelate Dehydrogenase Native to *Pseudomonas putida*

Synthesis of a gene encoding (S)-mandelate dehydrogenase native to *Pseudomonas putida* (GenBank Accession Number: BAM38408) and a gene encoding benzoylformate decarboxylase native to *Pseudomonas putida* (GenBank Accession Number: BAM38407) was outsourced to Life Technologies, and a plasmid inserted with a DNA fragment containing these genes ligated to each other was obtained. These genes had been codon-optimized for expression in *E. coli*. By using the plasmid as the template, a DNA fragment containing the (S)-mandelate dehydrogenase gene was PCR-amplified. As primers, NdeI-mdlB-F (5'-ggaattccatATGAGCCGCAACCTGTTTAA-3'; SEQ ID NO: 7) and mdlB-XhoI-R (5'-accgctcgagTCATGCATGGGTGCCTTTAC-3'; SEQ ID NO: 8) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1200 bp was treated with restriction enzymes NdeI and XhoI, and ligated with pET22b (Novagen) similarly treated with NdeI and XhoI. *E.*

*coli* JM109 was transformed with this ligation mixture, an objective plasmid was extracted from an ampicillin resistant strain, and the plasmid was designated as pET22-mdlB. The nucleotide sequence of the mdlB gene (SMDH gene) harbored by pET22-mdlB is shown as SEQ ID NO: 27, and the amino acid sequence of MdlB (SMDH) encoded by this gene is shown as SEQ ID NO: 28.

<2> Preparation for Culture Broth of Strain Expressing (S)-Mandelate Dehydrogenase

*E. coli* BL21(DE3) was introduced with the expression plasmid pET22-mdlB for (S)-mandelate dehydrogenase native to *Pseudomonas putida*, and a transformant strain harboring this plasmid was obtained from ampicillin resistant strains. The transformant strain was cultured overnight at 30° C. on LB-amp (100 mg/L) plate. The obtained cells were inoculated into 100 mL of Overnight Express Instant TB Medium (Novagen) containing 100 mg/L of ampicillin contained in a Sakaguchi flask, and cultured at 37° C. with shaking for 16 hr. The obtained culture broth was hereinafter used as MdlB culture broth.

Example 4: Expression of Benzoylformate Decarboxylase (MdlC, BFDC) Native to *Pseudomonas putida*

<1> Construction of Plasmid for Expression of Benzoylformate Decarboxylase Native to *Pseudomonas putida*

By using the plasmid inserted with the gene encoding (S)-mandelate dehydrogenase native to *Pseudomonas putida* (GenBank Accession Number: BAM38408) and the gene encoding benzoylformate decarboxylase native to *Pseudomonas putida* (GenBank Accession Number: BAM38407) described in Example 3 as the template, a DNA fragment containing the benzoylformate decarboxylase gene was PCR-amplified. As primers, AseI-mdlC-F (5'-ggaattcat-taATGGCAAGCGTTCATGGCA-3'; SEQ ID NO: 9) and mdlC-XhoI-R (5'-accgctcgagTCATTTAACCG-GACTAACGG-3'; SEQ ID NO: 10) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1600 bp was treated with restriction enzymes AseI and XhoI, and ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-mdlC. The nucleotide sequence of the mdlC gene (BFDC gene) harbored by pET22-mdlC is shown as SEQ ID NO: 29, and the amino acid sequence of MdlC (BFDC) encoded by this gene is shown as SEQ ID NO: 30.

<2> Preparation for Culture Broth of Strain Expressing Benzoylformate Decarboxylase

*E. coli* BL21(DE3) was introduced with the expression plasmid pET22-mdlC for benzoylformate decarboxylase native to *Pseudomonas putida*, and a transformant strain harboring this plasmid was obtained from ampicillin resistant strains. The transformant strain was cultured overnight at 30° C. on LB-amp (100 mg/L) plate. The obtained cells were inoculated into 100 mL of Overnight Express Instant TB Medium (Novagen) containing 100 mg/L of ampicillin contained in a Sakaguchi flask, and cultured at 37° C. with shaking for 16 hr. The obtained culture broth was hereinafter used as MdlC culture broth.

Example 5: Synthesis of Benzaldehyde from L-Phe

By using the culture broths obtained in Examples 1 to 4, benzaldehyde was synthesized from L-phenylalanine (L-Phe) via the procedures described below. Benzaldehyde was quantified by HPLC analysis. The analysis conditions were as follows:

Mobile phase A: 10 mM $KH_2PO_4$/10 mM $K_2HPO_4$

Mobile phase B: acetonitrile

Flow rate: 1.0 mL/min

Column temperature: 40° C.

Detection: UV 210 nm

Column: CAPCELL PAK MGII, 4.6×150 mm, 3 m (Shiseido)

Gradient: 0-2 min (B: 2%), 2-16 min (B: 2-50%), 16.1-20 min (B: 2%)

A 10 mL aliquot of the AAD culture broth obtained in Example 1 was centrifuged, 8 mL of the supernatant was removed, and the cells were suspended in the remaining culture supernatant, to obtain a 5-fold concentrate. This concentrate was used for the following reactions as AAD concentrate. Similarly, 5-fold concentrates were prepared from the HMAS culture broths, HPPD culture broths, MdlB culture broth, and MdlC culture broth, and used for the following reactions as HMAS concentrates, HPPD concentrates, MdlB concentrate, and MdlC concentrate.

<1> Reaction in 1 Step

A reaction mixture (1 mL) containing 50 mM of L-Phe, 0.01 mM of iron sulfate, 10 mM of trisodium citrate, 30 mM of sodium ascorbate, 10 mM of thiamine pyrophosphate chloride, 1 mM of magnesium sulfate, 100 mM of potassium phosphate buffer (pH 7.0), 0.02 mL of AAD concentrate, 0.1 mL of HMAS or HPPD concentrate, 0.04 mL of MdlB concentrate, and 0.02 mL of MdlC concentrate was put into a test tube, and shaken at 15° C. for 20 hr. A 0.01 mL aliquot of the reaction mixture was mixed with 1 mL of a reaction stop solution (1% phosphoric acid, 50% ethanol), and a centrifugal supernatant thereof was subjected to HPLC analysis. Results are shown in Table 1.

TABLE 1

| Culture broth added | Benzaldehyde (mM) |
|---|---|
| AAD, HMAS Ao, MdlB, and MdlC | N.D. |
| AAD, HMAS Sc, MdlB, and MdlC | N.D. |
| AAD, HMAS Rr, MdlB, and MdlC | 0.10 |
| AAD, HMAS St, MdlB, and MdlC | 0.45 |
| AAD, HMAS At, MdlB, and MdlC | 4.47 |
| AAD, HMAS Ab, MdlB, and MdlC | 0.04 |
| AAD, HMAS Ka, MdlB, and MdlC | N.D. |
| AAD, HMAS Nc, MdlB, and MdlC | 0.15 |
| AAD, HMAS Ar, MdlB, and MdlC | N.D. |
| AAD, HMAS As, MdlB, and MdlC | 0.14 |
| AAD, HMAS Sr, MdlB, and MdlC | 2.19 |
| AAD, HMAS Ha, MdlB, and MdlC | N.D. |
| AAD, HPPD Sa, MdlB, and MdlC | N.D. |
| AAD, HPPD Pp, MdlB, and MdlC | N.D. |

N.D.: Not detected.

<2> Reaction in 2 Steps

A reaction mixture (1 mL) containing 50 mM of L-Phe, 0.01 mM of iron sulfate, 10 mM of trisodium citrate, 30 mM of sodium ascorbate, 10 mM of thiamine pyrophosphate chloride, 1 mM of magnesium sulfate, 100 mM of potassium phosphate buffer (pH 7.0), 0.02 mL of AAD concentrate, 0.1 mL of HMAS or HPPD concentrate, and 0.02 mL of MdlB concentrate was put into a test tube, and shaken at 15° C. for 20 hr. The reaction mixture was centrifuged, a 0.49 mL aliquot of the supernatant was mixed with 0.01 mL of MdlC concentrate, and the resultant mixture was put into a test tube and shaken at 15° C. for 4 hr. A 0.1 mL aliquot of the reaction mixture was mixed with 1 mL of a reaction stop solution (1% phosphoric acid, 50% ethanol), and a centrifugal supernatant thereof was subjected to HPLC analysis. Results are shown in Table 2.

Table 2

| Culture broth added | Benzaldehyde (mM) |
|---|---|
| AAD, HMAS Ao, MdlB, and MdlC | 1.30 |
| AAD, HMAS Sc, MdlB, and MdlC | 0.57 |
| AAD, HMAS Rr, MdlB, and MdlC | 1.11 |
| AAD, HMAS St, MdlB, and MdlC | 0.97 |
| AAD, HMAS At, MdlB, and MdlC | 7.07 |
| AAD, HMAS Ab, MdlB, and MdlC | 0.28 |
| AAD, HMAS Ka, MdlB, and MdlC | N.D. |
| AAD, HMAS Nc, MdlB, and MdlC | 4.31 |
| AAD, HMAS Ar, MdlB, and MdlC | N.D. |
| AAD, HMAS As, MdlB, and MdlC | 0.29 |
| AAD, HMAS Sr, MdlB, and MdlC | 5.23 |
| AAD, HMAS Ha, MdlB, and MdlC | N.D. |
| AAD, HPPD Sa, MdlB, and MdlC | N.D. |
| AAD, HPPD Pp, MdlB, and MdlC | N.D. |

N.D.: Not detected.

Example 6: Construction of Plasmid pHSG-AHB for Co-Expression of AAD, HMAS at, and MdlB (SMDH)

<1> Preparation of DNA Fragment Containing AAD Gene

As the first step, by using the expression plasmid pSFN-AAD for amino acid deaminase native to *Providencia rettgeri* AJ2770 described in Example 1 as the template, a DNA fragment A containing an SD sequence and an upstream part of the AAD gene and a DNA fragment B containing a downstream part of the AAD gene were each PCR-amplified. As primers, EcoRI-SD-aad-F (5'-ACCGgaattctaaggaggaatgcatATGAA-3'; SEQ ID NO: 46) and aad-delEcoRI-R (5'-CTCTTTAAATACTGGaAATTCTTTTCTCAG-3'; SEQ ID NO: 49) were used for amplification of the DNA fragment A, and aad-delEcoRI-F (5'-CTGAGAAAAGAATTtCCAGTATTTAAAGAG-3'; SEQ ID NO: 48) and aad-SacI-R (5'-ACCGgagctcTTAGCTAAAACGGGAAAGTT-3'; SEQ ID NO: 47) were used for amplification of the DNA fragment B. As the second step, by using the DNA fragments A and B as the template, a DNA fragment C containing the SD sequence and the full-length AAD gene of which an EcoRI-recognition site was eliminated was PCR-amplified. As primers, EcoRI-SD-aad-F (SEQ ID NO: 46) and aad-SacI-R (SEQ ID NO: 47) were used for amplification of the DNA fragment C. PCR was carried out for amplification of each DNA fragment by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 90 sec |
| 1 cycle | 68° C., 90 sec |
| | 4° C. |

The obtained DNA fragment C of about 1400 bp was treated with restriction enzymes EcoRI and SacI, and hereinafter used as a DNA fragment containing the AAD gene.

<2> Preparation of DNA Fragment Containing HMAS at Gene

By using the expression plasmid pSFN-AAD for amino acid deaminase native to *Providencia rettgeri* AJ2770 described in Example 1 as the template, a DNA fragment containing the phoC promoter sequence was PCR-amplified. As primers, PphoC up-F (5'-AAGCGGCAGGGTCGGAACAGGAGAG-3'; SEQ ID NO: 50) and PphoC NdeI-R (5'-CATATGcattcctccttacggtgttatatg-3'; SEQ ID NO: 51) were used. Separately, by using the expression plasmid pET22-hmaS At for 4-hydroxymandelate synthase native to *Actinoplanes teichomyceticus* described in Example 2<1-5> as the template, a DNA fragment containing the HMAS At gene was PCR-amplified. As primers, PphoC-NdeI-hmaS At-F (5'-ccgtaaggaggaatgCATATGACCATGACGGGCCACTTTC-3'; SEQ ID NO: 52) and T7 terminator (5'-GCTAGTTATTGCTCAGCGG-3'; SEQ ID NO: 53) were used. By using the thus-obtained two DNA fragments as the template, a DNA fragment containing the phoC promoter and the HMAS At gene ligated to each other was PCR-amplified. As primers, SacI-PphoC-F (5'-accgGAGCTCatttttcaatgtgatttta-3'; SEQ ID NO: 54) and T7 terminator (SEQ ID NO: 53) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1200 bp was treated with restriction enzymes SacI and XhoI, and hereinafter used as a DNA fragment containing the HMAS At gene.

<3> Preparation of DNA Fragment Containing mdlB (SMDH) Gene

A DNA fragment containing the phoC promoter sequence was PCR-amplified in the same manner as described in <2>. Separately, by using the expression plasmid pET22-mdlB for (S)-mandelate dehydrogenase native to *Pseudomonas putida* described in Example 3 as the template, a DNA fragment containing the mdlB (SMDH) gene was PCR-amplified. As primers, PphoC-NdeI-mdlB-F (5'-ccgtaaggaggaatgCATATGAGCCGCAACCTGTTTAACG-3'; SEQ ID NO: 55) and mdlB-BamHI-R (5'-ACCGggatccTCATGCATGGGTGCCTTTAC-3'; SEQ ID NO: 56) were used. By using the thus-obtained two DNA fragments as the template, a DNA fragment containing the phoC promoter and the mdlB (SMDH) gene ligated to each other was PCR-amplified. As primers, XhoI-PphoC-F (5'-accgCTCGAGatttttcaatgtgatttta-3'; SEQ ID NO: 57) and mdlB-BamHI-R (SEQ ID NO: 56) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1300 bp was treated with restriction enzymes XhoI and BamHI, and hereinafter used as a DNA fragment containing the mdlB (SMDH) gene.

<4> Construction of Plasmid Harboring AAD, HMAS at, and mdlB (SMDH) Genes

All the DNA fragments containing the AAD, HMAS At, and mdlB (SMDH) genes obtained above were ligated with pHSG298 (Takara Bio) treated with EcoRI and BamHI. *E. coli* JM109 was transformed with this ligation mixture, an objective plasmid harboring all the AAD, HMAS At, and mdlB (SMDH) genes was extracted from a kanamycin resistant strain, and the plasmid was designated as pHSG-AHB.

Example 7: Synthesis of Benzaldehyde from Glucose

An *E. coli* L-phenylalanine-producing strain AJ12741 (JP H05-344881 A) was introduced with the plasmid pHSG-AHB for co-expression of AAD, HMAS At, and MdlB (SMDH) constructed in Example 6, and a transformant strain harboring this plasmid was obtained as a kanamycin and ampicillin resistant strain. The obtained strain was designated as pHSG-AHB/AJ12741. Similarly, the AJ12741 strain was introduced with a control vector pHSG298 not expressing AAD, HMAS At, or MdlB (SMDH), and an obtained transformant strain was designated as pHSG/AJ12741. By using the constructed strains, benzaldehyde was synthesized from glucose via the procedures described below. Benzaldehyde was quantified by HPLC analysis. The analysis conditions were as described in Example 5.

The constructed strains, pHSG-AHB/AJ12741 and pHSG/AJ12741, were each cultured for 3 days at 25° C. on LB-km (25 mg/L)-amp (100 mg/L) plate, i.e. LB plate containing 25 mg/L of kanamycin and 100 mg/L of ampicillin. The obtained cells were inoculated into 4 mL of a benzoylformate production medium (20 g/L of glucose, 1 g/L of $MgSO_4$-$7H_2O$, 2 g/L of Yeast Extract, 16 g/L of $(NH_4)_2SO_4$, 1 g/L of $KH_2PO_4$, 10 mg/L of $FeSO_4$-$7H_2O$, 10 mg/L of $MnSO_4$-$5H_2O$, 0.1 g/L of L-tyrosine, 30 g/L of $CaCO_3$, 25 mg/L of kanamycin, and 100 mg/L of ampicillin, adjusted to pH 7.0) and cultured at 30° C. with shaking for 48 hr. The culture broth was centrifuged, a 0.49 mL aliquot of the supernatant was mixed with 0.01 mL of MdlC concentrate prepared in Example 5, and the resultant mixture was put into a test tube and shaken at 15° C. for 4 hr. A 0.1 mL aliquot of the reaction mixture was mixed with 1 mL of a reaction stop solution (1% phosphoric acid, 50% ethanol), and a centrifugal supernatant thereof was subjected to HPLC analysis. As a result, 2.92 mM of benzaldehyde was detected for the pHSG-AHB/AJ12741 strain, while benzaldehyde was not detected for the pHSG/AJ12741 strain.

As described above, it was revealed that benzaldehyde can be produced from L-phenylalanine or glucose by using microorganism(s) expressing AAD, HMAS, MdlB (SMDH), and MdlC (BFDC).

Example 8: Improvement of Benzaldehyde Production Via Modification of HMAS

In order to improve benzaldehyde production, various mutations were introduced into 4-hydroxymandelate synthase native to *Actinoplanes teichomyceticus* (HMAS At).

<1> Construction of Plasmid for Expression of HMAS At-His (1)

By using the plasmid inserted with the gene encoding 4-hydroxymandelate synthase native to *Actinoplanes teichomyceticus* described in Example 2<1-5> as the template, a DNA fragment containing the HMAS At gene was PCR-amplified. As primers, T7 promoter (5'-TAATACGACTCACTATAGGG-3'; SEQ ID NO: 58) and hmaS At-Xho-His-R (5'-accgctcgagACGGCCATCCGCGGCAGCCT-3'; SEQ ID NO: 59) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1100 bp was treated with restriction enzymes NdeI and XhoI, and ligated with pET22b (Novagen) similarly treated with NdeI and XhoI. *E. coli* JM109 was transformed with this ligation mixture, an objective plasmid was extracted from an ampicillin resistant strain, and the plasmid was designated as pET22-hmaS At-His. When using this plasmid, HMAS At is expressed with His-tag fused at C-terminus. This His-tag-fused HMAS At was designated as HMAS At-His.

<2> Construction of Plasmid for Expression of Mutant HMAS At-His (1)

By using pET22-hmaS At-His as the template, mutations shown in Table 3 were each introduced into HMAS At-His. Introduction of mutation was carried out by using PrimeSTAR Max (Takara Bio) and primers shown in Table 3 under the following conditions:

| | |
|---|---|
| 30 cycles | 98° C., 10 sec |
| | 60° C., 15 sec |
| | 72° C., 40 sec |
| 1 cycle | 4° C. |

TABLE 3

| Mutant No | Mutation | Nucleotide Sequence of Primer (5'→3') | SEQ ID NO |
|---|---|---|---|
| 1 | I217L | ACGGTCttaGCGCCGGATACCACACGC | 60 |
| | | CGGCGCtaaGACCGTTAAGGTCACAGC | 61 |
| 2 | I336V | GGCAACgttAAAGCGCTGTATGAAGCG | 62 |
| | | CGCTTTaacGTTGCCTGAACCGAAAGT | 63 |

*E. coli* JM109 was transformed with each PCR solution, and an objective plasmid was extracted from an ampicillin resistant strain. The obtained plasmids were hereinafter used as expression plasmids for mutant HMAS At-His.

<3> Purification of Mutant HMAS At-His (1)

The expression plasmids for mutant HMAS At-His obtained in Example 8<2> were each introduced into *E. coli* BL21(DE3), a transformant strain harboring each plasmid was obtained from ampicillin resistant strains. The transformant strain was cultured overnight at 30° C. on LB-amp (100 mg/L) plate. The obtained cells were inoculated into 10 mL of Overnight Express Instant TB Medium (Novagen)

containing 100 mg/L of ampicillin contained in a test tube, and cultured at 30° C. with shaking for 16 hr. Cells were obtained from the culture broth by centrifugation, suspended with 2 mL of xTractor Buffer (Takara Bio), and incubated statically at the room temperature for 20 min, to thereby disrupt the cells. The cell disruption product was centrifuged to thereby remove cell debris, and the supernatant was hereinafter used as a soluble fraction. The soluble fraction was applied to a purification column for His-tag-fused proteins, HisTALON Superflow Cartridges (Takara Bio, CV=1 mL), equilibrated beforehand with a buffer (20 mM of Tris-HCl (pH 8.0), 300 mM of NaCl, and 10 mM of imidazole), so that proteins were absorbed to the column. Proteins not absorbed to the column were washed out with the same buffer. The proteins absorbed to the column were eluted by passing an elution buffer (20 mM of Tris-HCl (pH 8.0), 300 mM of NaCl, and 150 mM of imidazole) through the column at a flow rate of 1.5 mL/min. The eluted fractions were collected and concentrated by using Amicon Ultra-15 30K (Millipore). The concentrate was diluted with 20 mM of Tris-HCl (pH7.6), and hereinafter used as a purified enzyme of the mutant HMAS At-His.

<4> Construction of Plasmid for Expression of HMAS At-His (2)

By using the expression plasmid pSFN-AAD for amino acid deaminase native to *Providencia rettgeri* AJ2770 described in Example 1 as the template, a DNA fragment containing the phoC promoter sequence was PCR-amplified. As primers, PphoC up-F (SEQ ID NO: 50) and PphoC NdeI-R (SEQ ID NO: 51) were used. Separately, by using the expression plasmid pET22-hmaS At-His for 4-hydroxymandelate synthase native to *Actinoplanes teichomyceticus* described in Example 8<1> as the template, a DNA fragment containing the HMAS At-His gene was PCR-amplified. As primers, PphoC-NdeI-hmaS At-F (SEQ ID NO: 52) and His6 SacI-R (5'-ACCGgagctcagtggtggtggtggtggtg-3'; SEQ ID NO: 64) were used. By using the thus-obtained two DNA fragments as the template, a DNA fragment containing the phoC promoter and the HMAS At-His gene ligated to each other was PCR-amplified. As primers, EcoRI-PphoC-F (5'-gaaccgGAATTCattttttcaatgtgatttta-3'; SEQ ID NO: 65) and His6 SacI-R (SEQ ID NO: 64) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment of about 1200 bp was treated with restriction enzymes EcoRI and SacI, and ligated with pUC18 (Takara Bio) similarly treated with EcoRI and SacI. *E. coli* JM109 was transformed with this ligation mixture, an objective plasmid was extracted from an ampicillin resistant strain, and the plasmid was designated as pPC-hmaS At-His.

By using pPC-hmaS At-His as the template, a DNA fragment containing the phoC promoter sequence was PCR-amplified. As primers, PphoC up-F (SEQ ID NO: 50) and PphoC SDact NdeI-R (5'-ATGGTCATatggattcctccttacggtgtt-3'; SEQ ID NO: 66) were used. PCR was carried out by using KOD-plus-ver.2 (TOYOBO) under the following conditions:

| | |
|---|---|
| 1 cycle | 94° C., 2 min |
| 25 cycles | 98° C., 10 sec |
| | 60° C., 10 sec |
| | 68° C., 60 sec |
| 1 cycle | 68° C., 60 sec |
| | 4° C. |

The obtained DNA fragment was treated with restriction enzymes EcoRI and NdeI, and ligated with pPC-hmaS At-His similarly treated with EcoRI and NdeI. *E. coli* JM109 was transformed with this ligation mixture, an objective plasmid was extracted from an ampicillin resistant strain, and the plasmid was designated as pPC-hmaS At-His (SDatc). When using this plasmid, HMAS At is expressed with His-tag fused at C-terminus, i.e. as HMAS At-His.

<5> Construction of Plasmid for Expression of Mutant HMAS At-His (2)

By using pPC-hmaS At-His(SDatc) as the template, mutations were each introduced into HMAS At-His. Introduction of mutation was carried out by using GeneMorph II Random Mutagenesis kit (Agilent Technologies) under the following conditions. As primers, M13 Primer M4 (5'-GTTTTCCCAGTCACGAC-3'; SEQ ID NO: 67) and M13 Primer RV (5'-CAGGAAACAGCTATGAC-3'; SEQ ID NO: 68) were used.

| | |
|---|---|
| 1 cycle | 95° C., 2 min |
| 30 cycles | 95° C., 30 sec |
| | 60° C., 30 sec |
| | 72° C., 60 sec |
| 1 cycle | 72° C., 10 min |
| | 4° C. |

The obtained DNA fragment was treated with restriction enzymes NdeI and XhoI, and ligated with pPC-hmaS At-His similarly treated with NdeI and XhoI. *E. coli* JM109 was transformed with this ligation mixture, and plasmids were extracted from ampicillin resistant strains, to thereby obtain a library of expression plasmids for mutant HMAS At-His. *E. coli* JM109 was transformed with the plasmid library, and transformant strains harboring the expression plasmids for mutant HMAS At-His were obtained. The plasmids were extracted from the respective transformant strains, and the nucleotide sequences of the mutant HMAS At-His genes were determined. The obtained mutants have the mutations shown in Table 4.

TABLE 4

| Mutant No | Mutation |
|---|---|
| 3 | G327D |
| 4 | G327S |
| 5 | Y18F/D220N |
| 6 | D35G/E46Q/T222S/I336V |
| 7 | D220A/Q347L |
| 8 | M3I/A199S/G255D |
| 9 | T2N |
| 10 | V194G |
| 11 | Q206R |
| 12 | A27V/E191K |
| 13 | I217V |

<6> Purification of Mutant HMAS At-His (2)

The transformant strains harboring the expression plasmids for mutant HMAS At-His of Nos. 10-13 were each cultured overnight at 30° C. on LB-amp (100 mg/L) plate. The obtained cells were inoculated into 10 mL of TB-amp (100 mg/L) contained in a test tube, and cultured at 37° C. with shaking for 16 hr. Treatment of cells and purification of enzymes were performed in the same manner as described in Example 8<3>, to thereby obtain purified enzymes of the mutant HMAS At-His. Similarly, the transformant strain harboring pPC-hmaS At-His(SDatc) was cultured, and the wild-type (WT) HMAS At-His was purified, to thereby obtain a purified enzyme of the wild-type HMAS At-His.

<7> Synthesis of Benzaldehyde from L-Phe by Using Purified Enzyme of Mutant HMAS At-His By using the purified mutant and wild-type enzymes of HMAS At-His, benzaldehyde was synthesized from L-phenylalanine (L-Phe) in 2 step via the procedures described below. Benzaldehyde was quantified by HPLC analysis. The analysis conditions were the same as those described in Example 5.

A reaction mixture (1 mL) containing 50 mM of L-Phe, 0.01 mM of iron sulfate, 10 mM of trisodium citrate, 30 mM of sodium ascorbate, 10 mM of thiamine pyrophosphate chloride, 1 mM of magnesium sulfate, 100 mM of potassium phosphate buffer (pH 7.0), 0.02 mL of AAD concentrate, 0.25 mg/mL of purified enzyme of HMAS At-His, and 0.02 mL of MdlB concentrate was put into a test tube, and shaken at 15° C. for 20 hr. The reaction mixture was centrifuged, a 0.49 mL aliquot of the supernatant was mixed with 0.01 mL of MdlC concentrate, and the resultant mixture was put into a test tube and shaken at 15° C. for 4 hr. A 0.1 mL aliquot of the reaction mixture was mixed with 1 mL of a reaction stop solution (1% phosphoric acid, 50% ethanol), and a centrifugal supernatant thereof was subjected to HPLC analysis. Results are shown in Table 5.

TABLE 5

| Mutant No | Mutation | Benzaldehyde (mM) |
|---|---|---|
| 1 | I217L | 1.26 |
| 2 | I336V | 1.47 |
| 10 | V194G | 1.07 |
| 11 | Q206R | 1.74 |
| 12 | A27V/E191K | 2.05 |
| 13 | I217V | 1.26 |
| WT | — | 1.03 |

<8> Construction of Plasmid for Expression of Mutant HMAS At-His (3)

By using pPC-hmaS At-His I217V (SDatc), which encodes the mutant HMAS At-His having I217V mutation, as the template, mutations were each further introduced thereinto. Introduction of mutation and construction of a plasmid library were performed in the same manner as described in Example 8<5>. *E. coli* JM109 was transformed with the plasmid library, and transformant strains harboring the expression plasmids for mutant HMAS At-His were obtained. The plasmids were extracted from the respective transformant strains, and the nucleotide sequences of the mutant HMAS At-His genes were determined. The obtained mutants have the mutations shown in Table 6.

TABLE 6

| Mutant No | Mutation |
|---|---|
| 14 | E180K/I217V/D220N |
| 15 | G5R/I217V |
| 16 | I217V/V343M |
| 17 | Q206R/I217V |
| 18 | A199V/I217V/K337Q |
| 19 | I217V/F319Y |
| 20 | A187V/I217V |
| 21 | D201N/I217V |

<9> Preparation for Culture Broth of Strains Expressing Mutant HMAS At-His

The transformant strains harboring the expression plasmids for mutant HMAS At-His of Nos. 3-12 and 14-21 were each cultured overnight at 30° C. on LB-amp (100 mg/L) plate. The obtained cells were inoculated into 10 mL of TB-amp (100 mg/L) contained in a test tube, and cultured at 37° C. with shaking for 16 hr. The obtained culture broth was concentrated by centrifugation, to obtain a 5-fold concentrate. Similarly, the transformant strain harboring pPC-hmaS At-His(SDatc) was cultured, and a 5-fold concentrate of the culture broth of the wild-type (WT) HMAS At-His was prepared. These concentrates were used for the following reaction as HMAS At-His concentrates.

<7> Synthesis of Benzaldehyde from L-Phe by Using Mutant HMAS At-His

By using the HMAS At-His concentrates, benzaldehyde was synthesized from L-phenylalanine (L-Phe) in 2 step via the procedures described below. Benzaldehyde was quantified by HPLC analysis. The analysis conditions were the same as those described in Example 5.

A reaction mixture (1 mL) containing 50 mM of L-Phe, 0.01 mM of iron sulfate, 10 mM of trisodium citrate, 30 mM of sodium ascorbate, 10 mM of thiamine pyrophosphate chloride, 1 mM of magnesium sulfate, 100 mM of potassium phosphate buffer (pH 7.0), 0.02 mL of AAD concentrate, 0.1 mL of HMAS At-His concentrate, and 0.02 mL of MdlB concentrate was put into a test tube, and shaken at 15° C. for 20 hr. The reaction mixture was centrifuged, a 0.49 mL aliquot of the supernatant was mixed with 0.01 mL of MdlC concentrate, and the resultant mixture was put into a test tube and shaken at 15° C. for 4 hr. A 0.1 mL aliquot of the reaction mixture was mixed with 1 mL of a reaction stop solution (1% phosphoric acid, 50% ethanol), and a centrifugal supernatant thereof was subjected to HPLC analysis. Results are shown in Table 7.

TABLE 7

| Mutant No | Mutation | Benzaldehyde (mM) |
|---|---|---|
| 3 | G327D | 3.51 |
| 4 | G327S | 4.76 |
| 5 | Y18F/D220N | 4.07 |
| 6 | D35G/E46Q/T222S/I336V | 3.03 |
| 7 | D220A/Q347L | 2.71 |
| 8 | M3I/A199S/G255D | 3.04 |
| 9 | T2N | 4.38 |
| 10 | V194G | 4.78 |
| 11 | Q206R | 3.31 |
| 12 | A27V/E191K | 3.14 |
| 14 | E180K/I217V/D220N | 3.43 |
| 15 | G5R/I217V | 3.37 |
| 16 | I217V/V343M | 3.62 |
| 17 | Q206R/I217V | 3.34 |
| 18 | A199V/I217V/K337Q | 3.24 |
| 19 | I217V/F319Y | 3.14 |
| 20 | A187V/I217V | 3.26 |
| 21 | D201N/I217V | 3.44 |
| WT | — | 2.69 |

According to the present invention, benzaldehyde can be efficiently produced from L-phenylalanine or a carbon source.

EXPLANATION OF SEQUENCE LISTING

SEQ ID NOS:

1-10: Primers

11: Nucleotide sequence of AAD gene of *Providencia rettgeri* AJ2770

12: Amino acid sequence of AAD of *Providencia rettgeri* AJ2770

13: Nucleotide sequence of HMAS gene of *Amycolatopsis orientalis*

14: Amino acid sequence of HMAS of *Amycolatopsis orientalis*

15: Nucleotide sequence of HMAS gene of *Streptomyces coelicolor*

16: Amino acid sequence of HMAS of *Streptomyces coelicolor*

17: Nucleotide sequence of HMAS gene of *Streptomyces toyocaensis*

18: Amino acid sequence of HMAS of *Streptomyces toyocaensis*

19: Nucleotide sequence of HMAS gene of *Rhodococcus rhodnii*

20: Amino acid sequence of HMAS of *Rhodococcus rhodnii*

21: Nucleotide sequence of HMAS gene of *Actinoplanes teichomyceticus*

22: Amino acid sequence of HMAS of *Actinoplanes teichomyceticus*

23: Nucleotide sequence of HPPD gene of *Streptomyces avermitilis*

24: Amino acid sequence of HPPD of *Streptomyces avermitilis*

25: Nucleotide sequence of HPPD gene of *Pseudomonas putida*

26: Amino acid sequence of HPPD of *Pseudomonas putida*

27: Nucleotide sequence of SMDH gene of *Pseudomonas putida*

28: Amino acid sequence of SMDH of *Pseudomonas putida*

29: Nucleotide sequence of BFDC gene of *Pseudomonas* putida

30: Amino acid sequence of BFDC of *Pseudomonas* putida

31: Nucleotide sequence of wild-type AAD gene of *Providencia rettgeri* AJ2770

32: Nucleotide sequence of HMAS gene of *Amycolatopsis balhimycina*

33: Amino acid sequence of HMAS of *Amycolatopsis balhimycina*

34: Nucleotide sequence of HMAS gene of *Kibdelosporangium aridum*

35: Amino acid sequence of HMAS of *Kibdelosporangium aridum*

36: Nucleotide sequence of HMAS gene of *Nonomuraea coxensis*

37: Amino acid sequence of HMAS of *Nonomuraea coxensis*

38: Nucleotide sequence of HMAS gene of *Actinoplanes rectilineatus*

39: Amino acid sequence of HMAS of *Actinoplanes rectilineatus*

40: Nucleotide sequence of HMAS gene of *Actinoplanes subtropicus*

41: Amino acid sequence of HMAS of *Actinoplanes subtropicus*

42: Nucleotide sequence of HMAS gene of *Streptomyces rimosus*

43: Amino acid sequence of HMAS of *Streptomyces rimosus*

44: Nucleotide sequence of HMAS gene of *Herpetosiphon aurantiacus*

45: Amino acid sequence of HMAS of *Herpetosiphon aurantiacus*

46-68: Primers

We claim:

1. A method for producing benzaldehyde, the method comprising:

(A) producing benzaldehyde by using one or more microorganisms having one or more benzaldehyde generation enzymes, wherein said benzaldehyde generation enzymes consist of amino acid deaminase, 4-hydroxymandelate synthase, (S)-mandelate dehydrogenase, and benzoylformate decarboxylase, and wherein said one or more microorganisms is:

1) one microorganism which has all four of said benzaldehyde generation enzymes, or 2) a plurality of microorganisms comprising all four of said benzaldehyde generation enzymes among said plurality of microorganisms.

2. The method according to claim 1, wherein said producing is carried out by a method selected from the group consisting of:

(a) cultivating the one or more microorganisms so that benzaldehyde is produced from a carbon source via fermentation;

(b) producing an intermediate of benzaldehyde from a carbon source and then converting said intermediate into benzaldehyde using the cells of the one or more microorganisms; and (c) combinations thereof.

3. The method according to claim 1, wherein said benzaldehyde is produced from a carbon source.

4. The method according to claim 1, wherein said benzaldehyde is produced from L-phenylalanine.

5. The method according to claim 1, wherein said producing comprises:

(B) producing benzaldehyde from a carbon source by using the one or more microorganisms, wherein the one or more microorganisms have L-phenylalanine-producing ability; or (C) converting L-phenylalanine into benzaldehyde by using the one or more microorganisms.

6. The method according to claim 1, wherein said producing comprises:

(B1) cultivating the one or more microorganisms in a culture medium containing a carbon source to generate and accumulate benzaldehyde in the culture medium, wherein the one or more microorganisms have L-phenylalanine-producing ability;

(C1) cultivating the one or more microorganisms in a culture medium containing L-phenylalanine to generate and accumulate benzaldehyde in the culture medium; or (C2) allowing cells of the one or more microorganisms to coexist with L-phenylalanine in a reaction mixture to generate and accumulate benzaldehyde in the reaction mixture.

7. The method according to claim 1, wherein said producing comprises:

(D1) a method selected from the group consisting of:

(D1a) generating phenylpyruvate, (S)-mandelate, and/or benzoylformate from a carbon source by using a first of said one or more microorganisms, wherein said first of said one or more microorganisms is able to catalyze the conversion of L-phenylalanine into phenylpyruvate, (S)-mandelate, and/or benzoylformate, and has L-phenylalanine-producing ability; and (D1b) converting L-phenylalanine into phenylpyruvate, (S)-mandelate, and/or benzoylformate by using a first of said one or more microorganisms, wherein said first of said one or more microorganisms is able to catalyze the conversion of L-phenylalanine into phenylpyruvate, (S)-mandelate, and/or benzoylformate; and (D2) converting said phenylpyruvate, (S)-mandelate, and/or benzoylformate generated or converted in (D1) into benzaldehyde by using a second of said one or more microorganisms, wherein said second of said one or more microorganisms is able to catalyze the conversion of phenylpyruvate, (S)-mandelate, and/or benzoylformate into benzaldehyde.

8. The method according to claim 7, wherein said generating of (D1a) is carried out by cultivating said first of said one or more microorganisms recited in (D1a), wherein said converting of (D1b) is carried out by using cells of said first of said one or more microorganisms recited in (D1b) or by cultivating said first of said one or more microorganisms recited in (D1b), and wherein said converting of (D2) is carried out by using cells of said second of said one or more microorganisms or by cultivating said second of said one or more microorganisms.

9. The method according to claim 1, wherein said producing comprises:

(E1) a method selected from the group consisting of:

(E1a) generating benzoylformate from a carbon source by using a first of said one or more microorganisms having amino acid deaminase, 4-hydroxymandelate synthase, and (S)-mandelate dehydrogenase, and having L-phenylalanine-producing ability; and (E1b) converting L-phenylalanine into benzoylformate by using a first of said one or more microorganisms having amino acid deaminase, 4-hydroxymandelate synthase, and (S)-mandelate dehydrogenase; and (E2) converting benzoylformate generated or converted in (E1) into benzaldehyde by using a second microorganism having benzoylformate decarboxylase.

10. The method according to claim 9, wherein said generating of (E1a) is carried out by cultivating said first of said one or more microorganisms recited in (E1a), wherein said converting of (E1b) is carried out by using cells of said first of said one or more microorganisms recited in (E1b) or by cultivating said first of said one or more microorganisms recited in (E1b), and wherein said converting of (E2) is carried out by using cells of said second microorganism or by cultivating said second microorganism.

11. The method according to claim 1, wherein said producing comprises:

(F1) a method selected from the group consisting of:

(F1a) cultivating a first of said one or more microorganisms in a culture medium containing a carbon source to generate and accumulate benzoylformate in the culture medium, wherein said first of said one or more microorganisms has amino acid deaminase, 4-hydroxymandelate synthase, and (S)-mandelate dehydrogenase, and has L-phenylalanine-producing ability; and (F1b) cultivating a first of said one or more microorganisms in a culture medium containing L-phenylalanine to generate and accumulate benzoylformate in the culture medium, or allowing cells of a first of said one or more microorganisms to coexist with L-phenylalanine in a reaction mixture to generate and accumulate benzoylformate in the reaction mixture, wherein said first one or more microorganisms has amino acid deaminase, 4-hydroxymandelate synthase, and (S)-mandelate dehydrogenase; and (F2) cultivating a second microorganism in the culture medium containing said benzoylformate generated in (F1) to generate and accumulate benzaldehyde in the culture medium, or allowing cells of a second microorganism to coexist with said benzoylformate generated in (F1) in a reaction mixture to generate and accumulate benzaldehyde in the reaction mixture, wherein said second microorganism has benzoylformate decarboxylase.

12. The method according to claim 1, wherein said producing comprises:

(G1) a method selected from the group consisting of:

(G1a) generating phenylpyruvate from a carbon source by using a first microorganism having amino acid deaminase and having L-phenylalanine-producing ability; and (G1b) converting L-phenylalanine into phenylpyruvate by using a first microorganism having amino acid deaminase;

(G2) converting phenylpyruvate generated or converted in (G1) into (S)-mandelate by using a second microorganism having 4-hydroxymandelate synthase;

(G3) converting (S)-mandelate converted in (G2) into benzoylformate by using a third microorganism having (S)-mandelate dehydrogenase; and (G4) converting benzoylformate converted in (G3) into benzaldehyde by using a fourth microorganism having benzoylformate decarboxylase.

13. The method according to claim 12, wherein said generating of (G1a) is carried out by cultivating the first microorganism recited in (G1a), wherein said converting of (G1b) is carried out by using cells of the first microorganism recited in (G1b) or by cultivating the first microorganism recited in (G1b), wherein said converting of (G2) is carried out by using cells of the second microorganism or by cultivating the second microorganism, wherein said converting of (G3) is carried out by using cells of the third microorganism or by cultivating the third microorganism, and wherein said converting of (G4) is carried out by using cells of the fourth microorganism or by cultivating the fourth microorganism.

14. The method according to claim 2, wherein said one or more microorganisms is present in a culture broth or a processed product of a culture broth;

or is collected from a culture broth or processed product of a culture broth.

15. The method according to claim 1, wherein the amino acid deaminase is a protein selected from the group consisting of:

(a) a protein comprising the amino acid sequence of SEQ ID NO: 12;

(b) a protein comprising the amino acid sequence of SEQ ID NO: 12 but including substitution, deletion, insertion, and/or addition of 1 to 10 amino acid residues, and having amino acid deaminase activity; and (c) a protein comprising an amino acid sequence having an identity of 90% or higher to the amino acid sequence of SEQ ID NO: 12, and having amino acid deaminase activity.

16. The method according to claim 1, wherein the 4-hydroxymandelate synthase is a protein selected from the group consisting of:

(a) a protein comprising the amino acid sequence of SEQ ID NO: 22;

(b) a protein comprising the amino acid sequence of SEQ ID NO: 22 but including substitution, deletion, insertion, and/or addition of 1 to 10 amino acid residues, and having 4-hydroxymandelate synthase activity;

(c) a protein comprising an amino acid sequence having an identity of 90% or higher to the amino acid sequence of SEQ ID NO: 22 and having 4-hydroxymandelate synthase activity; and (d) a protein of the above (a), (b), or (c), but having a specific mutation at an amino acid residue selected from the group consisting of T2, M3, G5, Y18, A27, D35, E46, E180, A187, E191, V194, A199, D201, Q206, I217, D270, T222, G255, F319, G327, I336, K337, V343, Q347, and combinations thereof;

(e) a protein comprising the amino acid sequence of SEQ ID NO: 14, 16, 18, 20, 33, 37, 41, 43, or 45;

(f) a protein comprising the amino acid sequence of SEQ ID NO: 14, 16, 18, 20, 33, 37, 41, 43, or 45 but including substitution, deletion, insertion, and/or addition of 1 to 10 amino acid residues, and having 4-hydroxymandelate synthase activity; and (g) a protein comprising an amino acid sequence having an identity of 90% or higher to the amino acid sequence of SEQ ID NO: 14, 16, 18, 20, 33, 37, 41, 43, or 45, and having 4-hydroxymandelate synthase activity;

provided that 4-hydroxymandelate synthase cannot be a protein having only the amino acid sequence of SEQ ID NOS: 35 or 39.

17. The method according to claim 16, wherein the specific mutation is selected from the group consisting of T2N, M3I, G5R, Y18F, A27V, D35G, E46Q E180K, A187V, E191K, V194G, A199(S, V), D201N, Q206R, I217(L, V), D220(A, N), T222S, G255D, F319Y, G327(D, S), I336V, K337Q, V343M, Q347L, and combinations thereof.

18. The method according to claim 16, wherein the specific mutation is selected from the group consisting of M3I/A199S/G255D, Y18F/D220N, A27V/E191K, D35G/E46Q/T2225/I336V, E180K/I217V/D720N, A187V/I217V, A199V/I217V/K337Q, D201N/I217V, I217V/F319Y, and D220A/Q347L.

19. The method according to claim 1, wherein the (5)-mandelate dehydrogenase is a protein selected from the group consisting of:

(a) a protein comprising the amino acid sequence of SEQ ID NO: 28;

(b) a protein comprising the amino acid sequence of SEQ ID NO: 28 but including substitution, deletion, insertion, and/or addition of 1 to 10 amino acid residues, and having (S)-mandelate dehydrogenase activity; and (c) a protein comprising an amino acid sequence having an identity of 90% or higher to the amino acid sequence of SEQ ID NO: 28, and having (S)-mandelate dehydrogenase activity.

20. The method according to claim 1, wherein the benzoylformate decarboxylase is a protein selected from the group consisting of:

(a) a protein comprising the amino acid sequence of SEQ ID NO: 30;

(b) a protein comprising the amino acid sequence of SEQ ID NO: 30 but including substitution, deletion, insertion, and/or addition of 1 to 10 amino acid residues, and having benzoylformate decarboxylase activity; and (c) a protein comprising an amino acid sequence having an identity of 90% or higher to the amino acid sequence of SEQ ID NO: 30, and having benzoylformate decarboxylase activity.

21. The method according to claim 1, wherein the one or more microorganisms is a bacterium or yeast.

22. The method according to claim 1, wherein the one or more microorganisms is a bacterium belonging to the family Enterobacteriaceae or a coryneform bacterium.

23. The method according to claim 1, wherein the one or more microorganisms is a bacterium belonging to the genus *Escherichia.*

24. The method according to claim 1, wherein the one or more microorganisms is *Escherichia coli.*

25. The method according to claim 1, the method further comprising collecting the benzaldehyde.

26. The method according to claim 1, wherein the amino acid deaminase comprises the amino acid sequence of SEQ ID NO: 12.

* * * * *